(12) United States Patent
Schwartz et al.

(10) Patent No.: US 7,470,660 B2
(45) Date of Patent: Dec. 30, 2008

(54) TREATMENT FOR DARK ADAPTATION

(75) Inventors: Daniel M. Schwartz, San Francisco, CA (US); Keith G. Duncan, San Francisco, CA (US); Kathy Bailey, San Francisco, CA (US); John P. Kane, Hillsborough, CA (US); Brian Y. Ishida, Walnut Creek, CA (US)

(73) Assignee: The Regents of the University of California, Oakland, CA (US)

( * ) Notice: Subject to any disclaimer, the term of this patent is extended or adjusted under 35 U.S.C. 154(b) by 390 days.

(21) Appl. No.: 11/055,309

(22) Filed: Feb. 10, 2005

(65) Prior Publication Data

US 2005/0282750 A1 Dec. 22, 2005

Related U.S. Application Data

(60) Division of application No. 10/794,198, filed on Mar. 5, 2004, which is a continuation-in-part of application No. 10/428,551, filed on May 2, 2003, which is a continuation-in-part of application No. 10/313,641, filed on Dec. 6, 2002, now abandoned.

(60) Provisional application No. 60/340,498, filed on Dec. 7, 2001, provisional application No. 60/415,864, filed on Oct. 3, 2002.

(51) Int. Cl.
| | |
|---|---|
| A61K 31/685 | (2006.01) |
| A61K 31/7088 | (2006.01) |
| A61K 38/02 | (2006.01) |
| A61K 38/10 | (2006.01) |
| A61K 38/17 | (2006.01) |

(52) U.S. Cl. ............... 514/2; 514/12; 514/13; 514/21; 514/44; 514/78

(58) Field of Classification Search ............ None
See application file for complete search history.

(56) References Cited

U.S. PATENT DOCUMENTS

| | | | | |
|---|---|---|---|---|
| 5,080,478 | A * | 1/1992 | O'Brien et al. ............. 351/224 |
| 5,721,114 | A | 2/1998 | Abrahamsen et al. |
| 5,733,761 | A | 3/1998 | Treco et al. |
| 5,780,592 | A | 7/1998 | Mullner et al. |
| 5,824,685 | A | 10/1998 | Campochiaro et al. |
| 5,866,551 | A | 2/1999 | Benoit et al. |
| 5,990,081 | A | 11/1999 | Ageland et al. |
| 6,033,885 | A | 3/2000 | Latta et al. |
| 6,071,924 | A | 6/2000 | Campochiaro et al. |
| 6,075,032 | A | 6/2000 | Campochiaro et al. |
| 6,090,921 | A | 7/2000 | Winge et al. |
| 6,258,596 | B1 | 7/2001 | Benoit et al. |
| 6,287,590 | B1 | 9/2001 | Dasseux |
| 6,320,074 | B1 * | 11/2001 | Boehm et al. ............... 562/490 |
| 6,329,341 | B1 | 12/2001 | Dasseux et al. |
| 6,367,479 | B1 | 4/2002 | Williams |
| 6,369,098 | B1 | 4/2002 | Pershadsingh et al. |
| 6,372,753 | B1 | 4/2002 | Campochiaro et al. |
| 6,376,464 | B1 | 4/2002 | Dasseux et al. |
| 6,423,830 | B1 | 7/2002 | Winge et al. |
| 6,506,879 | B1 | 1/2003 | Ageland et al. |
| 6,555,582 | B1 | 4/2003 | Schwartz et al. |
| 6,559,284 | B1 | 5/2003 | Ageland et al. |
| 6,617,134 | B1 | 9/2003 | Sirtori et al. |
| RE38,556 | E | 7/2004 | Benoit et al. |
| 6,844,327 | B2 * | 1/2005 | Dasseux et al. ............... 514/44 |
| 7,250,407 | B2 * | 7/2007 | Dasseux et al. ............... 514/44 |
| 2001/0006656 | A1 * | 7/2001 | Harlan et al. ............... 424/400 |
| 2002/0102581 | A1 | 8/2002 | Hageman et al. |
| 2003/0032078 | A1 * | 2/2003 | Travis ............... 435/26 |
| 2003/0065020 | A1 * | 4/2003 | Gale et al. ............... 514/423 |
| 2003/0114515 | A1 * | 6/2003 | Kaesemeyer ............... 514/423 |
| 2003/0149997 | A1 * | 8/2003 | Hageman ............... 800/8 |
| 2003/0162758 | A1 | 8/2003 | Schwartz et al. |
| 2003/0229062 | A1 | 12/2003 | Schwartz et al. |
| 2004/0266663 | A1 | 12/2004 | Schwartz et al. |

FOREIGN PATENT DOCUMENTS

| | | |
|---|---|---|
| WO | WO-00/52479 A2 | 9/2000 |
| WO | WO-00/52479 A3 | 9/2000 |
| WO | WO-01/06262 A1 | 1/2001 |
| WO | WO-01/58494 A2 | 8/2001 |
| WO | WO-01/58494 A3 | 8/2001 |

(Continued)

OTHER PUBLICATIONS

Blankenhorn, David H., et al.; Reversal of Atherosis and Sclerosis; Circulation 79(1):1-7, Jan. 1989.

(Continued)

*Primary Examiner*—Jeffrey E Russel
(74) *Attorney, Agent, or Firm*—Fulbright & Jaworski LLP

(57) ABSTRACT

The present invention addresses the treatment of age-related macular degeneration, and treatment of individuals with impaired visual function such as impaired dark adaptation, using regulation of pathogenic mechanisms similar to atherosclerosis. In further specific embodiments, compositions that increase reverse cholesterol transport are utilized as therapeutic targets for age-related macular degeneration and improving impaired dark adaptation. In a specific embodiment, the lipid content of the retinal pigment epithelium, and/or Bruch's membrane is reduced by delivering Apolipoprotein A1, particularly a mimetic peptide.

12 Claims, 19 Drawing Sheets

FOREIGN PATENT DOCUMENTS

WO    WO-02/13812 A1    2/2002

OTHER PUBLICATIONS

Mullins, Robert F., et al. ; Drusen associated with aging and age-related macular degeneration contain proteins common to extracellular deposits associated with atheroclerosis, elastosis, amyloidosis, and dense deposit disease; FASEB J, 14:835-846,2000.

Simonelli, Francesca, et al.; Apolipoprotein E Polymorphisms in Ae-Related Macular Degeneration in an Italian Population; Ophthalmic Res 33:325-328, 2001.

Milam, Ann H., et al. ; Dominant Late-onset Retinal degeneration with Regional Variation of Sub-Retinal Pigment Epithelium Deposits, Retinal Function and Photoreceptor Degeneration; Ophthalmology 107:2256-2266,2000.

Johnson, Lincoln V. et al., Complement Activation and Inflammatory Processes in Drusen Formation and Age Related Macular Degeneration; Exp. Eye Res. 73:887-896, 2001.

Friedman, Ephraim; The Role of the Atherosclerotic Process in the Pathogenesis of Age-relat4ed Macular Degeneration; American Journal of Ophthalmology 130(5):658-663, 2000.

Schmidt, Silke, et al.; Association of the Apolipoprotein E gene with age-related macular degeneration: Possible effect modification by family history, age, and gender; Molecular Vision 6;287-293, 2000.

Klaver, Caroline C.W. et al.; Genetic Association of Apolipoprotein E with Age-Related Macular Degeneration; Am.J. Hum. Genet. 63:200-206, 1998.

Anderson, Don H., et al..; Local Cellular Sources of Apolipoprotein E in the Human Retina and Retinal Pigmented Epithelium: Implications for the Process of Drusen Formation; Am J. Ophthalmol 131:767-781.2001.

Database NCBI Online, "Homo sapiens preapolipoprotein E (APOE) mRNA, complete cds.", K00396, (2002).

Database NCBI Online, "Human apolipoprotein E (epsilon-4 allele) gene, complete cds", M10065, (1994).

Database NCBI Online, "Human apolipoprotein E mRNA, complete cds", M12529, (1995) .

Database NCBI Online, "Preapolipoprotein E [Homo sapiens]", AAB59546, (2002).

Database NCBI Online, "Apolipoprotein E", AAB59397, (1994).

Database NCBI Online, "Apolipoprotein E", AAB59518, (1995).

Database NCBI Online, "Homo sapiens ATP-binding cassette, sub-family A (ABC1), member 1 (ANCA1), mRNA", NM_005502, (2008).

Database NCBI Online, "Homo sapiens mRNA for ABCA1, complete cds", AB055982, (2008).

Database NCBI Online, "ATP-binding cassette, sub-family A member 1 [Homo sapiens]", NP_005493, (2008).

Database NCBI Online, "ABCA1 [Homo sapiens]", BAB63210, (2001).

Database NCBI Online, "Homo sapiens scavenger receptor class B, member 1 (SCARB1), transcript variant 1, mRNA", NM_005505, (2008).

Database NCBI Online, "Sscavenger receptor class B, member 1 isoform 1 [Homo sapiens]", NP_005496, (2008).

Leeuwen et al. Risk of macular degeneration with station use should be interpreted with caution, British Medical Medical Journal, 323:1308-1308, 2001.

Melnikova I., Raising HDL cholesterol, Nature Reviews Drug Discovery 4, 185-186 (Mar. 2005).

Miller M., Raising an isolated low HDL-C level: Why, how, and when? Cleveland Clinic Journal Of Medicine 70(6) 53-560 (Jun. 2003).

* cited by examiner

PL

HDL

LDL

```
                        SEQUENCE LISTING

<160> NUMBER OF SEQ ID NOS: 17

<210> SEQ ID NO 1
<211> LENGTH: 1156
<212> TYPE: DNA
<213> ORGANISM: HUMAN

<400> SEQUENCE: 1
cgcagcggag gtgaaggacg tccttcccca ggagccgact ggccaatcac aggcaggaag      60
atgaaggttc tgtgggctgc gttgctggtc acattcctgg caggatgcca ggccaaggtg     120
gagcaagcgg tggagacaga gccggagccc gagctgcgcc agcagaccga gtggcagagc     180
ggccagcgct gggaactggc actgggtcgc ttttgggatt acctgcgctg ggtgcagaca     240
ctgtctgagc aggtgcagga ggagctgctc agctcccagg tcacccagga actgagggcg     300
ctgatggacg agaccatgaa ggagttgaag gcctacaaat cggaactgga ggaacaactg     360
accccggtgg cggaggagac gcgggcacgg ctgtccaagg agctgcaggc ggcgcaggcc     420
cggctgggcg cggacatgga ggacgtgtgc ggccgcctgg tgcagtaccg cggcgaggtg     480
caggccatgc tcggccagag caccgaggag ctgcgggtgc gcctcgcctc ccacctgcgc     540
aagctgcgta agcggctcct ccgcgatgcc gatgacctgc agaagcgcct ggcagtgtac     600
caggccgggg cccgcgaggg cgccgagcgc ggcctcagcg ccatccgcga gcgcctgggg     660
```

-continued

```
cccctggtgg aacagggccg cgtgcgggcc gccactgtgg gctccctggc cggccagccg    720
ctacaggagc gggcccaggc ctggggcgag cggctgcgcg cgcggatgga ggagatgggc    780
agccggaccc gcgaccgcct ggacgaggtg aaggagcagg tggcggaggt gcgcgccaag    840
ctggaggagc aggcccagca gatacgcctg caggccgagg ccttccaggc ccgcctcaag    900
agctggttcg agcccctggt ggaagacatg cagcgccagt gggccgggct ggtggagaag    960
gtgcaggctg ccgtgggcac cagcgccgcc cctgtgccca gcgacaatca ctgaacgccg   1020
aagcctgcag ccatgcgacc ccacgccacc ccgtgcctcc tgcctccgcg cagcctgcag   1080
cgggagaccc tgtccccgcc ccagccgtcc tcctggggtg gaccctagtt taataaagat   1140
tcaccaagtt tcacgc                                                   1156
```

<210> SEQ ID NO 2
<211> LENGTH: 5515
<212> TYPE: DNA
<213> ORGANISM: HUMAN

<400> SEQUENCE: 2

```
ggaacttgat gctcagagag gacaagtcat ttgcccaagg tcacacagct ggcaactggc     60
agacgagatt cacgccctgg caatttgact ccagaatcct aaccttaacc cagaagcacg    120
gcttcaagcc ctggaaacca caatacctgt ggcagccagg gggaggtgct ggaatctcat    180
ttcacatgtg gggagggggc tcctgtgctc aaggtcacaa ccaaagagga agctgtgatt    240
aaaacccagg tcccatttgc aaagcctcga cttttagcag gtgcatcata ctgttcccac    300
ccctcccatc ccacttctgt ccagccgcct agccccactt tctttttttt cttttttga    360 gacagtctcc ctcttgctga ggctggagtg cagtggcgca atctcggctc actgtaacct    420
ccgcctcccg ggttcaagcg attctcctgc ctcagcctcc caagtagcta ggattacagg    480
cgcccgccac cacgcctggc taactttttgt atttttagta gagatggggt ttcaccatgt    540
tggccaggct ggtctcaaac tcctgacctt aagtgattcg cccactgtgg cctcccaaag    600
tgctgggatt acaggcgtga gctaccgccc cagcccctc ccatcccact tctgtccagc      660
cccctagccc tactttcttt ctgggatcca ggagtccaga tccccagccc cctctccaga    720
ttacattcat ccaggcacag gaaaggacag ggtcaggaaa ggaggactct gggcggcagc    780
ctccacattc cccttccacg cttggccccc agaatggagg agggtgtctg tattactggg    840
cgaggtgtcc tcccttcctg gggactgtgg gggtggtca aaagacctct atgccccacc     900
tccttcctcc ctctgccctg ctgtgcctgg ggcaggggga aacagccca cctcgtgact     960 gggctgccca gccgccccta tccctggggg aggggcggg acaggggag ccctataatt     1020 ggacaagtct gggatccttg agtcctactc agcccagcg gaggtgaagg acgtccttcc    1080
ccaggagccg gtgagaagcg cagtcggggg cacgggatg agctcagggg cctctagaaa    1140
gagctgggac cctgggaagc cctggcctcc aggtagtctc aggagagcta ctcggggtcg   1200
ggcttgggga gaggaggagc gggggtgagg caagcagcag gggactggac ctgggaaggg   1260
ctgggcagca gagacgaccc gacccgctag aaggtggggt ggggagagca gctggactgg   1320
gatgtaagcc atagcaggac tccacgagtt gtcactatca ttatcgagca cctactgggt   1380
gtccccagtg tcctcagatc tccataactg gggagccagg ggcagcgaca cggtagctag   1440
ccgtcgattg gagaactta aaatgaggac tgaattagct cataaatgga acacggcgct    1500
taactgtgag gttggagctt agaatgtgaa gggagaatga ggaatgcgag actgggactg   1560
```

```
agatggaacc ggcggtgggg aggggggtggg gggatggaat ttgaacccccg ggagaggaag    1620
atggaatttt ctatggaggc cgacctgggg atggggagat aagagaagac caggaggggag    1680
ttaaataggg aatgggttgg gggcggcttg gtaaatgtgc tgggattagg ctgttgcaga    1740
taatgcaaca aggcttggaa ggctaacctg gggtgaggcc gggttggggg cgctgggggt    1800
gggaggagtc ctcactggcg gttgattgac agtttctcct tccccagact ggccaatcac    1860
aggcaggaag atgaaggttc tgtgggctgc gttgctggtc acattcctgg caggtatggg    1920
ggcggggctt gctcggttcc ccccgctcct ccccctctca tcctcacctc aacctcctgg    1980
ccccattcag acagaccctg gccccctct tctgaggctt ctgtgctgct tcctggctct    2040
gaacagcgat ttgacgctct ctgggcctcg gtttccccca tccttgagat aggagttaga    2100
agttgttttg ttgttgttgt tgttgttgt tgttttgttt ttttgagatg aagtctcgct    2160
ctgtcgccca ggctggagtg cagtggcggg atctcggctc actgcaagct ccgcctccca    2220
ggtccacgcc attctcctgc ctcagcctcc caagtagctg ggactacagg cacatgccac    2280
cacacccgac taactttttt gtattttcag tagagacggg gtttcaccat gttggccagg    2340
ctggtctgga actcctgacc tcaggtgatc tgcccgtttc gatctcccaa agtgctggga    2400
ttacaggcgt gagccaccgc acctggctgg gagttagagg tttctaatgc attgcaggca    2460
gatagtgaat accagacacg gggcagctgt gatctttatt ctccatcacc cccacacagc    2520
cctgcctggg gcacacaagg acactcaata catgcttttc cgctgggccg gtggctcacc    2580
cctgtaatcc cagcactttg ggaggccaag gtgggaggat cacttgagcc caggagttca    2640
acaccagcct gggcaacata gtgagaccct gtctctacta aaaatacaaa aattagccag    2700
gcatggtgcc acacacctgt gctctcagct actcaggagg ctgaggcagg aggatcgctt    2760
gagcccagaa ggtcaaggtt gcagtgaacc atgttcaggc cgctgcactc cagcctgggt    2820
gacagagcaa gaccctgttt ataaatacat aatgctttcc aagtgattaa accgactccc    2880
ccctcacccct gcccaccatg gctccaaaga agcatttgtg gagcaccttc tgtgtgcccc    2940
taggtagcta gatgcctgga cggggtcaga aggaccctga cccgaccttg aacttgttcc    3000
acacaggatg ccaggccaag gtggagcaag cggtggagac agagccggag cccgagctgc    3060
gccagcagac cgagtggcag agcggccagc gctgggaact ggcactgggt cgcttttggg    3120
attacctgcg ctgggtgcag acactgtctg agcaggtgca ggaggagctg ctcagctccc    3180
aggtcaccca ggaactgagg tgagtgtccc catcctggcc cttgaccctc ctggtgggcg    3240
gctatacctc cccaggtcca ggtttcattc tgccccgtgtc gctaagtctt gggggggcctg    3300
ggtctctgct ggttctagct tcctcttccc atttctgact cctggcttta gctctctgga    3360
attctctctc tcagctttgt ctctctctct tcccttctga ctcagtctct cacactcgtc    3420
ctggctctgt ctctgtcctt ccctagctct tttatataga gacagagaga tggggtctca    3480
ctgtgttgcc caggctggtc ttgaacttct gggctcaagc gatcctcccg cctcggcctc    3540
ccaaagtgct gggattagag gcatgagcac cttgcccggc ctcctagctc cttcttcgtc    3600
tctgcctctg ccctctgcat ctgctctctg catctgtctc tgtctccttc tctcggcctc    3660
tgccccgttc cttctctccc tcttgggtct ctctggctca tccccatctc gcccgcccca    3720
tcccagccct tctcccccgc ctccccactg tgcgacaccc tcccgccctc tcggccgcag    3780
ggcgctgatg gacgagacca tgaaggagtt gaaggcctac aaatcggaac tggaggaaca    3840
actgaccccg gtgcggagg agacgcgggc acgctgtcc aaggagctgc aggcggcgca    3900
ggccccggctg ggcgcggaca tggaggacgt gcgcggccgc ctggtgcagt accgcggcga    3960
```

-continued

```
ggtgcaggcc atgctcggcc agagcaccga ggagctgcgg gtgcgcctcg cctcccacct    4020
gcgcaagctg cgtaagcggc tcctccgcga tgccgatgac ctgcagaagc gcctggcagt    4080
gtaccaggcc ggggcccgcg agggcgccga gcgcggcctc agcgccatcc gcgagcgcct    4140
ggggcccctg gtggaacagg gccgcgtgcg ggccgccact gtgggctccc tggccggcca    4200
gccgctacag gagcgggccc aggcctgggg cgagcggctg cgcgcgcgga tggaggagat    4260
gggcagccgg acccgcgacc gcctggacga ggtgaaggag caggtggcgg aggtgcgcgc    4320
caagctggag gagcaggccc agcagatacg cctgcaggcc gaggccttcc aggcccgcct    4380
caagagctgg ttcgagcccc tggtggaaga catgcagcgc cagtgggccg ggctggtgga    4440
gaaggtgcag gctgccgtgg gcaccagcgc cgcccctgtg cccagcgaca atcactgaac    4500
gccgaagcct gcagccatgc gaccccacgc caccccgtgc ctcctgcctc cgcgcagcct    4560
gcagcgggag accctgtccc cgccccagcc gtcctcctgg ggtggaccct agtttaataa    4620
agattcacca agtttcacgc atctgctggc ctcccctgt gatttcctct aagccccagc    4680 ctcagttct ctttctgccc acatactgcc acacaattct cagcccctc ctctccatct    4740 gtgtctgtgt gtatctttct ctctgccctt ttttttttt tagacggagt ctggctctgt    4800
cacccaggct agagtgcagt ggcacgatct tggctcactg caacctctgc ctcttgggtt    4860
caagcgattc tgctgcctca gtagctggga ttacaggctc acaccaccac acccggctaa    4920
tttttgtatt tttagtagag acgagctttc accatgttgg ccaggcaggt ctcaaactcc    4980
tgaccaagtg atccacccgc cggcctccca agtgctgag attacaggcc tgagccacca    5040
tgcccggcct ctgcccctct ttcttttta gggggcaggg aaaggtctca ccctgtcacc    5100
cgccatcaca gctcactgca gcctccacct cctggactca agtgataagt gatcctcccg    5160
cctcagcctt tccagtagct gagactacag gcgcatacca ctaggattaa tttgggggg    5220 ggtggtgtgt gtggagatgg ggtctggctt tgttggccag gctgatgtgg aattcctggg    5280
ctcaagcgat actcccacct tggcctcctg agtagctgag actactggct agcaccacca    5340
cacccagctt tttattatta tttgtagaga caaggtctca atatgttgcc caggctagtc    5400
tcaaacccct ggctcaagag atcctccgcc atcggcctcc caaagtgctg ggattccagg    5460
catgggctcc gagcggcctg cccaacttaa taatattgtt cctagagttg cactc         5515
```

<210> SEQ ID NO 3
<211> LENGTH: 1157
<212> TYPE: DNA
<213> ORGANISM: HUMAN

<400> SEQUENCE: 3

```
ccccagcgga ggtgaaggac gtccttcccc aggagccgac tggccaatca caggcaggaa      60
gatgaaggtt ctgtgggctg cgttgctggt cacattcctg gcaggatgcc aggccaaggt     120
ggagcaagcg gtggagacag agccggagcc cgagctgcgc cagcagaccg agtggcagag     180
cggccagcgc tggaactgg cactgggtcg cttttgggat tacctgcgct gggtgcagac     240
actgtctgag caggtgcagg aggagctgct cagctcccaa gtcacccaag aactgagggc     300
gctgatggac gagaccatga aggagttgaa ggcctacaaa tcggaactgg aggaacaact     360
gaccccggta gcggaggaga cgcgggcacg gctgtccaag gagctgcaga cggcgcaggc     420
ccggctgggc gcggacatgg aggacgtgtg cggccgcctg gtgcagtacc gcggcgaggt     480
gcaggccatg ctcggccaga gcaccgagga gctgcgggtg cgcctcgcct ccacctgcg     540
```

-continued

```
caagctgcgt aagcggctcc tccgcgatcc cgatgacctg cagaagcgcc tggcagtgta    600
ccaggccggg gcccgcgagg gcgccgagcg cggcctcagc gccatccgcg agcgcctggg    660 gccccctggtg aacagggcc gcgtgcgggc cgccactgtg ggctccctgg ccggccagcc    720
gctacaggag cgggcccagg cctggggcga gcggctgcgc gcgcggatgg aggagatggg    780
cagtcggacc cgcgaccgcc tggacgaggt gaaggagcag gtggcggagg tgcgcgccaa    840
gctggaggag caggcccagc agatacgcct gcaggccgag gccttccagg cccgcctcaa    900
gagctggttc gagcccctgg tggaagacat gcagcgccag tgggccgggc tggtggagaa    960
ggtgcaggct gccgtgggca ccagcgccgc cctgtgccc agcgacaatc actgaacgcc   1020
gaagcctgca gccatgcgac cccacgccac cccgtgcctc ctgcctccgc gcagcctgca   1080 gcggagacc ctgtccccgc ccagccgtc ctcctggggt ggaccctagt ttaataaga    1140 ttcaccaagt ttcacgc                                                  1157
```

<210> SEQ ID NO 4
<211> LENGTH: 317
<212> TYPE: PRT
<213> ORGANISM: HUMAN

<400> SEQUENCE: 4

```
Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
```

-continued

```
                260                 265                 270
Glu Ala Phe Gln Ala Arg Leu Lys Ser Trp Phe Glu Pro Leu Val Glu
            275                 280                 285
Asp Met Gln Arg Gln Trp Ala Gly Leu Val Glu Lys Val Gln Ala Ala
        290                 295                 300
Val Gly Thr Ser Ala Ala Pro Val Pro Ser Asp Asn His
305                 310                 315

<210> SEQ ID NO 5
<211> LENGTH: 317
<212> TYPE: PRT
<213> ORGANISM: HUMAN

<400> SEQUENCE: 5

Met Lys Val Leu Trp Ala Ala Leu Leu Val Thr Phe Leu Ala Gly Cys
1               5                   10                  15
Gln Ala Lys Val Glu Gln Ala Val Glu Thr Glu Pro Glu Pro Glu Leu
                20                  25                  30
Arg Gln Gln Thr Glu Trp Gln Ser Gly Gln Arg Trp Glu Leu Ala Leu
            35                  40                  45
Gly Arg Phe Trp Asp Tyr Leu Arg Trp Val Gln Thr Leu Ser Glu Gln
        50                  55                  60
Val Gln Glu Glu Leu Leu Ser Ser Gln Val Thr Gln Glu Leu Arg Ala
65                  70                  75                  80
Leu Met Asp Glu Thr Met Lys Glu Leu Lys Ala Tyr Lys Ser Glu Leu
                85                  90                  95
Glu Glu Gln Leu Thr Pro Val Ala Glu Glu Thr Arg Ala Arg Leu Ser
            100                 105                 110
Lys Glu Leu Gln Ala Ala Gln Ala Arg Leu Gly Ala Asp Met Glu Asp
        115                 120                 125
Val Arg Gly Arg Leu Val Gln Tyr Arg Gly Glu Val Gln Ala Met Leu
    130                 135                 140
Gly Gln Ser Thr Glu Glu Leu Arg Val Arg Leu Ala Ser His Leu Arg
145                 150                 155                 160
Lys Leu Arg Lys Arg Leu Leu Arg Asp Ala Asp Asp Leu Gln Lys Arg
                165                 170                 175
Leu Ala Val Tyr Gln Ala Gly Ala Arg Glu Gly Ala Glu Arg Gly Leu
            180                 185                 190
Ser Ala Ile Arg Glu Arg Leu Gly Pro Leu Val Glu Gln Gly Arg Val
        195                 200                 205
Arg Ala Ala Thr Val Gly Ser Leu Ala Gly Gln Pro Leu Gln Glu Arg
    210                 215                 220
Ala Gln Ala Trp Gly Glu Arg Leu Arg Ala Arg Met Glu Glu Met Gly
225                 230                 235                 240
Ser Arg Thr Arg Asp Arg Leu Asp Glu Val Lys Glu Gln Val Ala Glu
                245                 250                 255
Val Arg Ala Lys Leu Glu Glu Gln Ala Gln Gln Ile Arg Leu Gln Ala
            260                 265                 270
Glu Ala Phe Gln Ala Arg Leu Lys Ser Trp Phe Glu Pro Leu Val Glu
        275                 280                 285
Asp Met Gln Arg Gln Trp Ala Gly Leu Val Glu Lys Val Gln Ala Ala
    290                 295                 300
Val Gly Thr Ser Ala Ala Pro Val Pro Ser Asp Asn His
305                 310                 315
```

<210> SEQ ID NO 6
<211> LENGTH: 317
<212> TYPE: PRT
<213> ORGANISM: HUMAN

<400> SEQUENCE: 6

```
Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Thr Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Pro Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His
305                 310                 315
```

<210> SEQ ID NO 7
<211> LENGTH: 10412
<212> TYPE: DNA
<213> ORGANISM: HUMAN

<400> SEQUENCE: 7

```
gtaattgcga gcgagagtga gtggggccgg gacccgcaga gccgagccga cccttctctc     60
ccgggctgcg gcagggcagg gcggggagct ccgcgcacca acagagccgg ttctcagggc    120
```

```
gctttgctcc ttgttttttc cccggttctg ttttctcccc ttctccggaa ggcttgtcaa    180
ggggtaggag aaagagacgc aaacacaaaa gtggaaaaca gttaatgacc agccacggcg    240
tccctgctgt gagctctggc cgctgccttc cagggctccc gagccacacg ctggggtgc     300 tggctgaggg aacatggctt gttggcctca gctgaggttg ctgctgtgga agaacctcac    360
tttcagaaga agacaaacat gtcagctgct gctggaagtg gcctggcctc tatttatctt    420
cctgatcctg atctctgttc ggctgagcta cccaccctat gaacaacatg aatgccattt    480
tccaaataaa gccatgccct ctgcaggaac acttccttgg gttcagggga ttatctgtaa    540
tgccaacaac ccctgtttcc gttacccgac tcctggggag gctcccggag ttgttggaaa    600
ctttaacaaa tccattgtgg ctcgcctgtt ctcagatgct cggaggcttc ttttatacag    660
ccagaaagac accagcatga aggacatgcg caaagttctg agaacattac agcagatcaa    720
gaaatccagc tcaaacttga agcttcaaga tttcctggtg acaatgaaa  ccttctctgg    780 gttcctgtat cacaacctct ctctcccaaa gtctactgtg acaagatgc  tgagggctga    840 tgtcattctc cacaaggtat ttttgcaagg ctaccagtta catttgacaa gtctgtgcaa    900
tggatcaaaa tcagaagaga tgattcaact tggtgaccaa aagtttctg  agctttgtgg    960 cctaccaagg gagaaactgg ctgcagcaga gcgagtactt cgttccaaca tggacatcct   1020
gaagccaatc ctgagaacac taaactctac atctcccttc ccgagcaagg agctggctga   1080
agccacaaaa acattgctgc atagtcttgg gactctggcc caggagctgt tcagcatgag   1140
aagctggagt gacatgcgac aggaggtgat gtttctgacc aatgtgaaca gctccagctc   1200
ctccacccaa atctaccagg ctgtgtctcg tattgtctgc gggcatcccg agggaggggg   1260
gctgaagatc aagtctctca actggtatga ggacaacaac tacaaagccc tctttggagg   1320
caatggcact gaggaagatg ctgaaacctt ctatgacaac tctacaactc cttactgcaa   1380
tgatttgatg aagaatttgg agtctagtcc tcttttcccgc attatctgga aagctctgaa   1440
gccgctgctc gttgggaaga tcctgtatac acctgacact ccagccacaa ggcaggtcat   1500
ggctgaggtg aacaagacct tccaggaact ggctgtgttc catgatctgg aaggcatgtg   1560
ggaggaactc agccccaaga tctggacctt catggagaac agccagaaa tggaccttgt    1620 ccggatgctg ttgacagca gggacaatga ccacttttgg gaacagcagt ggatggctt     1680 agattggaca gcccaagaca tcgtggcgtt tttggccaag cacccagagg atgtccagtc   1740
cagtaatggt tctgtgtaca cctggagaga agctttcaac gagactaacc aggcaatccg   1800
gaccatatct cgcttcatgg agtgtgtcaa cctgaacaag ctagaaccca tagcaacaga   1860
agtctggctc atcaacaagt ccatggagct gctggatgag aggaagttct gggctggtat   1920
tgtgttcact ggaattactc aggcagcat  tgagctgccc catcatgtca agtacaagat   1980
ccgaatggac attgacaatg tggagaggac aaataaaatc aaggatgggt actgggaccc   2040
tggtcctcga gctgaccct  ttgaggacat gcggtacgtc tgggggggct tcgcctactt   2100
gcaggatgtg gtggagcagg caatcatcag ggtgctgacg ggcaccgaga agaaaactgg   2160
tgtctatatg caacagatgc cctatccctg ttacgttgat gacatctttc tgcgggtgat   2220
gagccggtca atgcccctct tcatgacgct ggcctggatt tactcagtgg ctgtgatcat   2280
caagggcatc gtgtatgaga aggaggcacg gctgaaagag accatgcgga tcatgggcct   2340
ggacaacagc atcctctggt ttagctggtt cattagtagc ctcattcctc ttcttgtgag   2400
cgctggcctg ctagtggtca tcctgaagtt aggaaacctg ctgccctaca gtgatcccag   2460
```

```
cgtggtgttt gtcttcctgt ccgtgtttgc tgtggtgaca atcctgcagt gcttcctgat    2520
tagcacactc ttctccagag ccaacctggc agcagcctgt gggggcatca tctacttcac    2580
gctgtacctg ccctacgtcc tgtgtgtggc atggcaggac tacgtgggct tcacactcaa    2640
gatcttcgct agcctgctgt ctcctgtggc ttttgggttt ggctgtgagt actttgccct    2700
ttttgaggag cagggcattg gagtgcagtg ggacaacctg tttgagagtc ctgtggagga    2760
agatggcttc aatctcacca cttcggtctc catgatgctg tttgacacct tcctctatgg    2820
ggtgatgacc tggtacattg aggctgtctt tccaggccag tacggaattc ccaggccctg    2880
gtattttcct tgcaccaagt cctactggtt tggcgaggaa agtgatgaga gagccaccc    2940 tggttccaac cagaagagaa tatcagaaat ctgcatggag gaggaaccca cccacttgaa    3000
gctgggcgtg tccattcaga acctggtaaa agtctaccga gatgggatga aggtggctgt    3060
cgatggcctg gcactgaatt tttatgaggg ccagatcacc tccttcctgg ccacaatgg    3120 agcggggaag acgaccacca tgtcaatcct gaccgggttg ttcccccga cctcgggcac    3180 cgcctacatc ctgggaaaag acattcgctc tgagatgagc accatccggc agaacctggg    3240
ggtctgtccc cagcataacg tgctgtttga catgctgact gtcgaagaac acatctggtt    3300
ctatgcccgc ttgaaagggc tctctgagaa gcacgtgaag gcggagatgg agcagatggc    3360
cctggatgtt ggttttgccat caagcaagct gaaaagcaaa acaagccagc tgtcaggtgg    3420
aatgcagaga aagctatctg tggccttggc ctttgtcggg ggatctaagg ttgtcattct    3480
ggatgaaccc acagctggtg tggacccta ctcccgcagg gaatatggg agctgctgct    3540 gaaataccga caaggccgca ccattattct ctctacacac cacatggatg aagcggacgt    3600
cctgggggac aggattgcca tcatctccca tgggaagctg tgctgtgtgg gctcctccct    3660
gtttctgaag aaccagctgg gaacaggcta ctacctgacc ttggtcaaga agatgtgga    3720 atcctccctc agttcctgca gaaacagtag tagcactgtg tcatacctga aaaaggagga    3780
cagtgtttct cagagcagtt ctgatgctgg cctgggcagc gaccatgaga gtgacacgct    3840
gaccatcgat gtctctgcta tctccaacct catcaggaag catgtgtctg aagcccggct    3900
ggtggaagac atagggcatg agctgaccta tgtgctgcca tatgaagctg ctaaggaggg    3960
agcctttgtg gaactctttc atgagattga tgaccggctc tcagacctgg gcatttctag    4020
ttatggcatc tcagagacga ccctggaaga aatattcctc aaggtggccg aagagagtgg    4080
ggtggatgct gagacctcag atggtacctt gccagcaaga cgaaacaggc gggccttcgg    4140
ggacaagcag agctgtcttc gcccgttcac tgaagatgat gctgctgatc caaatgattc    4200
tgacatagac ccagaatcca gagagacaga cttgctcagt gggatggatg caaagggtc    4260 ctaccaggtg aaaggctgga aacttacaca gcaacagtttt gtggcccttt tgtggaagag    4320
actgctaatt gccagacgga gtcggaaagg atttttgct cagattgtct tgccagctgt    4380
gtttgtctgc attgccttg tgttcagcct gatcgtgcca cccttggca agtaccccag    4440 cctggaactt cagccctgga tgtacaacga acagtacaca tttgtcagca atgatgctcc    4500
tgaggacacg gaaccctgg aactcttaaa cgccctcacc aaagaccctg gcttcgggac    4560
ccgctgtatg gaaggaaacc caatcccaga cacgccctgc caggcagggg aggaagagtg    4620
gaccactgcc ccagttcccc agaccatcat ggacctcttc cagaatggga actggacaat    4680
gcagaaccct tcacctgcat gccagtgtag cagcgacaaa atcaagaaga tgctgcctgt    4740
gtgtccccca ggggcagggg ggctgcctcc tccacaaaga aaacaaaaca ctgcagatat    4800
ccttcaggac ctgacaggaa gaaacatttc ggattatctg gtgaagacgt atgtgcagat    4860
```

```
catagccaaa agcttaaaga acaagatctg ggtgaatgag tttaggtatg gcggcttttc    4920
cctgggtgtc agtaatactc aagcacttcc tccgagtcaa gaagttaatg atgccatcaa    4980
acaaatgaag aaacacctaa agctggccaa ggacagttct gcagatcgat ttctcaacag    5040
cttgggaaga tttatgacag gactggacac caaaaataat gtcaaggtgt ggttcaataa    5100
caagggctgg catgcaatca gctctttcct gaatgtcatc aacaatgcca ttctccgggc    5160
caacctgcaa aagggagaga accctagcca ttatggaatt actgctttca atcatcccct    5220
gaatctcacc aagcagcagc tctcagaggt ggctctgatg accacatcag tggatgtcct    5280
tgtgtccatc tgtgtcatct ttgcaatgtc cttcgtccca gccagctttg tcgtattcct    5340
gatccaggag cgggtcagca agcaaaaaca cctgcagttc atcagtggag tgaagcctgt    5400
catctactgg ctctctaatt ttgtctggga tatgtgcaat tacgttgtcc ctgccacact    5460
ggtcattatc atcttcatct gcttccagca gaagtcctat gtgtcctcca ccaatctgcc    5520
tgtgctagcc cttctacttt tgctgtatgg gtggtcaatc acacctctca tgtacccagc    5580
ctcctttgtg ttcaagatcc ccagcacagc ctatgtggtg ctcaccagcg tgaacctctt    5640
cattggcatt aatggcagcg tggccacctt tgtgctggag ctgttcaccg acaataagct    5700
gaataatatc aatgatatcc tgaagtccgt gttcttgatc ttcccacatt tttgcctggg    5760
acgagggctc atcgacatgg tgaaaaacca ggcaatggct gatgccctgg aaaggtttgg    5820
ggagaatcgc tttgtgtcac cattatcttg gacttggtg ggacgaaacc tcttcgccat    5880
ggccgtggaa ggggtggtgt tcttcctcat tactgttctg atccagtaca gattcttcat    5940
caggcccaga cctgtaaatg caaagctatc tcctctgaat gatgaagatg aagatgtgag    6000
gcgggaaaga cagagaattc ttgatggtgg aggccagaat gacatcttag aaatcaagga    6060
gttgacgaag atatatagaa ggaagcggaa gcctgctgtt gacaggattt gcgtgggcat    6120
tcctcctggt gagtgctttg ggctcctggg agttaatggg gctggaaaat catcaacttt    6180
caagatgtta acaggagata ccactgttac cagaggagat gctttcctta caaaaatag    6240
tatcttatca aacatccatg aagtacatca gaacatgggc tactgccctc agtttgatgc    6300
catcacagag ctgttgactg ggagagaaca cgtggagttc tttgcccttt tgagaggagt    6360
cccagagaaa gaagttggca aggttggtga gtgggcgatt cggaaactgg gcctcgtgaa    6420
gtatggagaa aaatatgctg gtaactatag tggaggcaac aaacgcaagc tctctacagc    6480
catggctttg atcggcgggc ctcctgtggt gttctggat gaacccacca caggcatgga    6540
tcccaaagcc cggcggttct tgtggaattg tgccctaagt gttgtcaagg agggagatc    6600
agtagtgctt acatctcata gtatggaaga atgtgaagct cttttgcacta ggatggcaat    6660
catggtcaat ggaaggttca ggtgccttgg cagtgtccag catctaaaaa ataggtttgg    6720
agatggttat acaatagttg tacgaatagc agggtccaac ccggacctga gcctgtcca    6780
ggatttcttt ggacttgcat ttcctggaag tgttctaaaa gagaaacacc ggaacatgct    6840
acaataccag cttccatctt cattatcttc tctggccagg atattcagca tcctctccca    6900
gagcaaaaag cgactccaca tagaagacta ctctgtttct cagacaacac ttgaccaagt    6960
atttgtgaac tttgccaagg accaaagtga tgatgaccac ttaaaagacc tctcattaca    7020
caaaaaccag acagtagtgg acgttgcagt tctcacatct tttctacagg atgagaaagt    7080
gaaagaaagc tatgtatgaa gaatcctgtt catacggggt ggctgaaagt aaagaggaac    7140
tagactttcc tttgcaccat gtgaagtgtt gtggagaaaa gagccagaag ttgatgtggg    7200
```

```
aagaagtaaa ctggatactg tactgatact attcaatgca atgcaattca atgcaatgaa    7260
aacaaaattc cattacaggg gcagtgcctt tgtagcctat gtcttgtatg gctctcaagt    7320
gaaagacttg aatttagttt tttacctata cctatgtgaa actctattat ggaacccaat    7380
ggacatatgg gtttgaactc cactttttt ttttttttt gttcctgtgt attctcattg     7440
gggttgcaac aataattcat caagtaatca tggccagcga ttattgatca aaatcaaaag    7500
gtaatgcaca tcctcattca ctaagccatg ccatgcccag gagactggtt tcccggtgac    7560
acatccattg ctggcaatga gtgtgccaga gttattagtg ccaagttttt cagaaagttt    7620
gaagcaccat ggtgtgtcat gctcactttt gtgaaagctg ctctgctcag agtctatcaa    7680
cattgaatat cagttgacag aatggtgcca tgcgtggcta acatcctgct ttgattccct    7740
ctgataagct gttctggtgg cagtaacatg caacaaaaat gtgggtgtct ccaggcacgg    7800
gaaacttggt tccattgtta tattgtccta tgcttcgagc catgggtcta cagggtcatc    7860
cttatgagac tcttaaatat acttagatcc tggtaagagg caagaatca acagccaaac    7920 tgctggggct gcaagctgct gaagccaggg catgggatta agagattgt gcgttcaaac    7980 ctagggaagc ctgtgcccat ttgtcctgac tgtctgctaa catggtacac tgcatctcaa    8040
gatgtttatc tgacacaagt gtattatttc tggcttttg aattaatcta gaaaatgaaa    8100
agatggagtt gtattttgac aaaaatgttt gtactttta atgttatttg gaattttaag    8160
ttctatcagt gacttctgaa tccttagaat ggcctctttg tagaaccctg tggtatagag    8220
gagtatggcc actgccccac tattttatt ttccttatgta agtttgcata tcagtcatga    8280
ctagtgccta gaaagcaatg tgatggtcag gatctcatga cattatattt gagtttcttt    8340
cagatcattt aggatactct taatctcact tcatcaatca aatattttt gagtgtatgc    8400 tgtagctgaa agagtatgta cgtacgtata agactagaga gatattaagt ctcagtacac    8460
ttcctgtgcc atgttattca gctcactggt ttacaaatat aggttgtctt gtggttgtag    8520
gagcccactg taacaatact gggcagcctt tttttttt ttttaattg caacaatgca     8580 aaagccaaga agtataagg gtcacaagtc taaacaatga attcttcaac agggaaaaca    8640
gctagcttga aaacttgctg aaaaacacaa cttgtgttta tggcatttag taccttcaaa    8700
taattggctt tgcagatatt ggatacccca ttaaatctga cagtctcaaa tttttcatct    8760
cttcaatcac tagtcaagaa aaatataaaa acaacaaata cttccatatg gagcattttt    8820
cagagttttc taacccagtc ttatttttct agtcagtaaa catttgtaaa aatactgttt    8880
cactaatact tactgttaac tgtcttgaga gaaaagaaaa atatgagaga actattgttt    8940
ggggaagttc aagtgatctt tcaatatcat tactaacttc ttccactttt tccagaattt    9000
gaatattaac gctaaaggtg taagacttca gatttcaaat taatctttct atatttttta    9060
aatttacaga atattatata acccactgct gaaaagaaa aaaatgattg ttttagaagt     9120
taaagtcaat attgatttta aatataagta atgaaggcat atttccaata actagtgata    9180
tggcatcgtt gcattttaca gtatcttcaa aaatacagaa tttatagaat aatttctcct    9240
catttaatat ttttcaaaat caaagttatg gtttcctcat tttactaaaa tcgtattcta    9300
attcttcatt atagtaaatc tatgagcaac tccttacttc ggttcctctg atttcaaggc    9360 catatttaa aaaatcaaaa ggcactgtga actattttga agaaaacaca acatttaat     9420 acagattgaa aggacctctt ctgaagctag aaacaatcta tagttataca tcttcattaa    9480
tactgtgtta cctttaaaa tagtaatttt ttacatttc ctgtgtaaac ctaattgtgg     9540
tagaaatttt taccaactct atactcaatc aagcaaaatt tctgtatatt ccctgtggaa    9600
```

| | |
|---|---:|
| tgtacctatg tgagtttcag aaattctcaa aatacgtgtt caaaaatttc tgcttttgca | 9660 |
| tctttgggac acctcagaaa acttattaac aactgtgaat atgagaaata cagaagaaaa | 9720 |
| taataagccc tctatacata aatgcccagc acaattcatt gttaaaaaac aaccaaacct | 9780 |
| cacactactg tatttcatta tctgtactga aagcaaatgc tttgtgacta ttaaatgttg | 9840 |
| cacatcattc attcactgta tagtaatcat tgactaaagc catttgtctg tgttttcttc | 9900 |
| ttgtggttgt atatatcagg taaaatattt tccaaagagc catgtgtcat gtaatactga | 9960 |
| accactttga tattgagaca ttaatttgta cccttgttat tatctactag taataatgta | 10020 |
| atactgtaga aatattgctc taattctttt caaaattgtt gcatccccct tagaatgttt | 10080 |
| ctatttccat aaggatttag gtatgctatt atcccttctt atacccctaag atgaagctgt | 10140 |
| ttttgtgctc tttgttcatc attggccctc attccaagca ctttacgctg tctgtaatgg | 10200 |
| gatctatttt tgcactggaa tatctgagaa ttgcaaaact agacaaaagt ttcacaacag | 10260 |
| atttctaagt taaatcattt tcattaaaag gaaaaaagaa aaaaatttt gtatgtcaat | 10320 |
| aactttatat gaagtattaa aatgcatatt tctatgttgt aatataatga gtcacaaaat | 10380 |
| aaagctgtga cagttctgtt ggtctacaga aa | 10412 |

<210> SEQ ID NO 8
<211> LENGTH: 6786
<212> TYPE: DNA
<213> ORGANISM: HUMAN

<400> SEQUENCE: 8

| | |
|---|---:|
| atggcttgtt ggcctcagct gaggttgctg ctgtggaaga acctcacttt cagaagaaga | 60 |
| caaacatgtc agctgctgct ggaagtggcc tggcctctat ttatcttcct gatcctgatc | 120 |
| tctgttcggc tgagctaccc accctatgaa caacatgaat gccatttttcc aaataaagcc | 180 |
| atgccctctg caggaacact tccttgggtt caggggatta tctgtaatgc caacaacccc | 240 |
| tgtttccgtt acccgactcc tggggaggct cccggagttg ttggaaactt aacaaatcc | 300 |
| attgtggctc gcctgttctc agatgctcgg aggcttcttt tatacagcca gaaagacacc | 360 |
| agcatgaagg acatgcgcaa agttctgaga acattacagc agatcaagaa atccagctca | 420 |
| aacttgaagc ttcaagattt cctggtggac aatgaaacct tctctgggtt cctgtatcac | 480 |
| aacctctctc tcccaaagtc tactgtggac aagatgctga gggctgatgt cattctccac | 540 |
| aaggtatttt gcaaggcta ccagttacat ttgacaagtc tgtgcaatgg atcaaaatca | 600 |
| gaagagatga ttcaacttgg tgaccaagaa gtttctgagc tttgtggcct accaagggag | 660 |
| aaactggctc agcagagcg agtacttcgt tccaacatgg acatcctgaa gccaatcctg | 720 |
| agaacactaa actctacatc tcccttcccg agcaaggagc tggctgaagc cacaaaaaca | 780 |
| ttgctgcata gtcttgggac tctggcccag gagctgttca gcatgagaag ctggagtgac | 840 |
| atgcgacagg aggtgatgtt tctgaccaat gtgaacagct ccagctcctc cacccaaatc | 900 |
| taccaggctg tgtctcgtat tgtctgcggg catcccgagg agggggggct gaagatcaag | 960 |
| tctctcaact ggtatgagga caacaactac aaagccctct ttggaggcaa tggcactgag | 1020 |
| gaagatgctg aaaccttcta tgacaactct acaactcctt actgcaatga tttgatgaag | 1080 |
| aatttggagt ctagtcctct ttcccgcatt atctggaaag ctctgaagcc gctgctcgtt | 1140 |
| gggaagatcc tgtatacacc tgacactcca gccacaaggc aggtcatggc tgaggtgaac | 1200 |
| aagacctcc aggaactggc tgtgttccat gatctggaag gcatgtggga ggaactcagc | 1260 |

```
cccaagatct ggaccttcat ggagaacagc caagaaatgg accttgtccg gatgctgttg    1320
gacagcaggg acaatgacca cttttgggaa cagcagttgg atggcttaga ttggacagcc    1380
caagacatcg tggcgttttt ggccaagcac ccagaggatg tccagtccag taatggttct    1440
gtgtacacct ggagagaagc tttcaacgag actaaccagg caatccggac catatctcgc    1500
ttcatggagt gtgtcaacct gaacaagcta gaacccatag caacagaagt ctggctcatc    1560
aacaagtcca tggagctgct ggatgagagg aagttctggg ctggtattgt gttcactgga    1620
attactccag gcagcattga gctgccccat catgtcaagt acaagatccg aatggacatt    1680
gacaatgtgg agaggacaaa taaaatcaag gatgggtact gggaccctgg tcctcgagct    1740
gacccctttg aggacatgcg gtacgtctgg gggggcttcg cctacttgca ggatgtggtg    1800
gagcaggcaa tcatcagggt gctgacgggc accgagaaga aaactggtgt ctatatgcaa    1860
cagatgccct atccctgtta cgttgatgac atctttctgc gggtgatgag ccggtcaatg    1920
cccctcttca tgacgctggc ctggatttac tcagtggctg tgatcatcaa gggcatcgtg    1980
tatgagaagg aggcacggct gaaagagacc atgcggatca tgggcctgga caacagcatc    2040
ctctggttta gctggttcat tagtagcctc attcctcttc ttgtgagcgc tggcctgcta    2100
gtggtcatcc tgaagttagg aaacctgctg ccctacagtg atcccagcgt ggtgtttgtc    2160
ttcctgtccg tgtttgctgt ggtgacaatc ctgcagtgct tcctgattag cacactcttc    2220
tccagagcca acctggcagc agcctgtggg ggcatcatct acttcacgct gtacctgccc    2280
tacgtcctgt gtgtggcatg gcaggactac gtgggcttca cactcaagat cttcgctagc    2340
ctgctgtctc ctgtggcttt tgggtttggc tgtgagtact ttgccctttt tgaggagcag    2400
ggcattggag tgcagtggga caacctgttt gagagtcctg tggaggaaga tggcttcaat    2460
ctcaccactt cggtctccat gatgctgttt gacaccttcc tctatggggt gatgacctgg    2520
tacattgagg ctgtctttcc aggccagtac ggaattccca ggccctggta ttttccttgc    2580
accaagtcct actggtttgg cgaggaaagt gatgagaaga gccaccctgg ttccaaccag    2640
aagagaatat cagaaatctg catggaggag gaacccaccc acttgaagct gggcgtgtcc    2700
attcagaacc tggtaaaagt ctaccgagat gggatgaagg tggctgtcga tggcctggca    2760
ctgaattttt atgagggcca gatcacctcc ttcctgggcc acaatggagc ggggaagacg    2820
accaccatgt caatcctgac cgggttgttc cccccgacct cgggcaccgc ctacatcctg    2880
ggaaaagaca ttcgctctga gatgagcacc atccggcaga acctgggggt ctgtccccag    2940
cataacgtgc tgtttgacat gctgactgtc gaagaacaca tctggttcta tgcccgcttg    3000
aaagggctct ctgagaagca cgtgaaggcg gagatggagc agatggccct ggatgttggt    3060
ttgccatcaa gcaagctgaa aagcaaaaca agccagctgt caggtggaat gcagagaaag    3120
ctatctgtgg ccttggcctt tgtcggggga tctaaggttg tcattctgga tgaacccaca    3180
gctggtgtgg acccttactc ccgcaggggga atatgggagc tgctgctgaa ataccgacaa    3240
ggccgcacca ttattctctc tacacaccac atggatgaag cggacgtcct ggggggacagg    3300 attgccatca tctcccatgg gaagctgtgc tgtgtgggct cctccctgtt ctgaagaac    3360 cagctgggaa caggctacta cctgaccttg gtcaagaaag atgtggaatc ctccctcagt    3420
tcctgcagaa acagtagtag cactgtgtca tacctgaaaa aggaggacag tgtttctcag    3480
agcagttctg atgctggcct gggcagcgac catgagagtg acacgctgac catcgatgtc    3540
tctgctatct ccaacctcat caggaagcat gtgtctgaag cccggctggt ggaagacata    3600
gggcatgagc tgacctatgt gctgccatat aagctgcta aggagggagc ctttgtggaa    3660
```

-continued

```
ctctttcatg agattgatga ccggctctca gacctgggca tttctagtta tggcatctca      3720
gagacgaccc tggaagaaat attcctcaag gtggccgaag agagtggggt ggatgctgag      3780
acctcagatg gtaccttgcc agcaagacga acaggcggg ccttcgggga caagcagagc      3840
tgtcttcgcc cgttcactga agatgatgct gctgatccaa atgattctga catagaccca      3900
gaatccagag agacagactt gctcagtggg atggatggca aagggtccta ccaggtgaaa      3960
ggctggaaac ttacacagca acagtttgtg gcccttttgt ggaagagact gctaattgcc      4020
agacggagtc ggaaaggatt ttttgctcag attgtcttgc cagctgtgtt tgtctgcatt      4080
gcccttgtgt tcagcctgat cgtgccaccc tttggcaagt accccagcct ggaacttcag      4140
ccctggatgt acaacgaaca gtacacattt gtcagcaatg atgctcctga ggacacggga      4200
accctggaac tcttaaacgc cctcaccaaa gaccctggct cgggacccg ctgtatggaa       4260
ggaaacccaa tcccagacac gccctgccag gcaggggagg aagagtggac cactgcccca     4320
gttccccaga ccatcatgga cctcttccag aatgggaact ggacaatgca gaacccttca    4380
cctgcatgcc agtgtagcag cgacaaaatc aagaagatgc tgcctgtgtg tcccccaggg     4440
gcaggggggc tgcctcctcc acaaagaaaa caaaacactg cagatatcct tcaggacctg     4500
acaggaagaa acatttcgga ttatctggtg aagacgtatg tgcagatcat agccaaaagc    4560
ttaaagaaca agatctgggt gaatgagttt aggtatggcg gcttttccct gggtgtcagt    4620
aatactcaag cacttcctcc gagtcaagaa gttaatgatg ccatcaaaca aatgaagaaa    4680
cacctaaagc tggccaagga cagttctgca gatcgatttc tcaacagctt gggaagattt    4740
atgacaggac tggacaccaa aaataatgtc aaggtgtggt tcaataacaa gggctggcat    4800
gcaatcagct ctttcctgaa tgtcatcaac aatgccattc tccgggccaa cctgcaaaag    4860
ggagagaacc ctagccatta tggaattact gctttcaatc atcccctgaa tctcaccaag    4920
cagcagctct cagaggtggc tctgatgacc acatcagtgg atgtccttgt gtccatctgt    4980
gtcatctttg caatgtcctt cgtcccagcc agctttgtcg tattcctgat ccaggagcgg    5040
gtcagcaaag caaaacacct gcagttcatc agtggagtga agcctgtcat ctactggctc    5100
tctaattttg tctgggatat gtgcaattac gttgtccctg ccacactggt cattatcatc    5160
ttcatctgct tccagcagaa gtcctatgtg tcctccacca atctgcctgt gctagccctt    5220
ctacttttgc tgtatgggtg gtcaatcaca cctctcatgt acccagcctc ctttgtgttc    5280
aagatcccca gcacagccta tgtggtgctc accagcgtga acctcttcat tggcattaat    5340
ggcagcgtgg ccacctttgt gctggagctg ttcaccgaca ataagctgaa taatatcaat    5400
gatatcctga gtccgtgttt cttgatcttc ccacatttttt gcctgggacg agggctcatc    5460
gacatggtga aaaaccaggc aatggctgat gccctggaaa ggtttgggga gaatcgcttt    5520
gtgtcaccat tatcttggga cttggtggga cgaaacctct tcgccatggc cgtggaaggg    5580
gtggtgttct tcctcattac tgttctgatc cagtacagat tcttcatcag gcccagacct    5640
gtaaatgcaa agctatctcc tctgaatgat gaagatgaag atgtgaggcg ggaaagacag    5700
agaattcttg atggtggagg ccagaatgac atcttagaaa tcaaggagtt gacgaagata    5760
tatagaagga agcggaagcc tgctgttgac aggatttgcg tgggcattcc tcctggtgag    5820
tgctttgggc tcctgggagt taatgggct ggaaaatcat caactttcaa gatgttaaca     5880
ggagatacca ctgttaccag aggagatgct ttccttaaca aaaatagtat cttatcaaac    5940
atccatgaag tacatcagaa catgggctac tgccctcagt ttgatgccat cacagagctg    6000
```

```
ttgactggga gagaacacgt ggagttcttt gcccttttga gaggagtccc agagaaagaa    6060
gttggcaagg ttggtgagtg ggcgattcgg aaactgggcc tcgtgaagta tggagaaaaa    6120
tatgctggta actatagtgg aggcaacaaa cgcaagctct ctacagccat ggctttgatc    6180
ggcgggcctc ctgtggtgtt tctggatgaa cccaccacag gcatggatcc caaagcccgg    6240
cggttcttgt ggaattgtgc cctaagtgtt gtcaaggagg ggagatcagt agtgcttaca    6300
tctcatagta tggaagagtg tgaagctctt tgcactagga tggcaatcat ggtcaatgga    6360
aggttcaggt gccttggcag tgtccagcat ctaaaaaata ggtttggaga tggttataca    6420
atagttgtac gaatagcagg gtccaacccg gacctgaagc ctgtccagga tttctttgga    6480
cttgcatttc ctggaagtgt tctaaaagag aaacaccgga acatgctaca ataccagctt    6540
ccatcttcat tatcttctct ggccaggata ttcagcatcc tctcccagag caaaagcga    6600 ctccacatag aagactactc tgtttctcag acaacacttg accaagtatt tgtgaacttt    6660
gccaaggacc aaagtgatga tgaccactta aaagacctct cattacacaa aaaccagaca    6720
gtagtggacg ttgcagttct cacatctttt ctacaggatg agaaagtgaa agaaagctat    6780
gtatga                                                                6786
```

<210> SEQ ID NO 9
<211> LENGTH: 2261
<212> TYPE: PRT
<213> ORGANISM: HUMAN

<400> SEQUENCE: 9

```
Met Ala Cys Trp Pro Gln Leu Arg Leu Leu Leu Trp Lys Asn Leu Thr
1               5                   10                  15

Phe Arg Arg Arg Gln Thr Cys Gln Leu Leu Glu Val Ala Trp Pro
        20                  25                  30

Leu Phe Ile Phe Leu Ile Leu Ile Ser Val Arg Leu Ser Tyr Pro Pro
    35                  40                  45

Tyr Glu Gln His Glu Cys His Phe Pro Asn Lys Ala Met Pro Ser Ala
50                  55                  60

Gly Thr Leu Pro Trp Val Gln Gly Ile Ile Cys Asn Ala Asn Asn Pro
65                  70                  75                  80

Cys Phe Arg Tyr Pro Thr Pro Gly Glu Ala Pro Gly Val Val Gly Asn
                85                  90                  95

Phe Asn Lys Ser Ile Val Ala Arg Leu Phe Ser Asp Ala Arg Arg Leu
            100                 105                 110

Leu Leu Tyr Ser Gln Lys Asp Thr Ser Met Lys Asp Met Arg Lys Val
        115                 120                 125

Leu Arg Thr Leu Gln Gln Ile Lys Lys Ser Ser Asn Leu Lys Leu
    130                 135                 140

Gln Asp Phe Leu Val Asp Asn Glu Thr Phe Ser Gly Phe Leu Tyr His
145                 150                 155                 160

Asn Leu Ser Leu Pro Lys Ser Thr Val Asp Lys Met Leu Arg Ala Asp
                165                 170                 175

Val Ile Leu His Lys Val Phe Leu Gln Gly Tyr Gln Leu His Leu Thr
            180                 185                 190

Ser Leu Cys Asn Gly Ser Lys Ser Glu Glu Met Ile Gln Leu Gly Asp
        195                 200                 205

Gln Glu Val Ser Glu Leu Cys Gly Leu Pro Arg Glu Lys Leu Ala Ala
    210                 215                 220

Ala Glu Arg Val Leu Arg Ser Asn Met Asp Ile Leu Lys Pro Ile Leu
```

```
                225                 230                 235                 240
Arg Thr Leu Asn Ser Thr Ser Pro Phe Pro Ser Lys Glu Leu Ala Glu
                245                 250                 255
Ala Thr Lys Thr Leu Leu His Ser Leu Gly Thr Leu Ala Gln Glu Leu
                260                 265                 270
Phe Ser Met Arg Ser Trp Ser Asp Met Arg Gln Glu Val Met Phe Leu
                275                 280                 285
Thr Asn Val Asn Ser Ser Ser Ser Thr Gln Ile Tyr Gln Ala Val
        290                 295                 300
Ser Arg Ile Val Cys Gly His Pro Glu Gly Gly Leu Lys Ile Lys
305                 310                 315                 320
Ser Leu Asn Trp Tyr Glu Asp Asn Asn Tyr Lys Ala Leu Phe Gly Gly
                    325                 330                 335
Asn Gly Thr Glu Glu Asp Ala Glu Thr Phe Tyr Asp Asn Ser Thr Thr
                340                 345                 350
Pro Tyr Cys Asn Asp Leu Met Lys Asn Leu Glu Ser Ser Pro Leu Ser
                355                 360                 365
Arg Ile Ile Trp Lys Ala Leu Lys Pro Leu Leu Val Gly Lys Ile Leu
        370                 375                 380
Tyr Thr Pro Asp Thr Pro Ala Thr Arg Gln Val Met Ala Glu Val Asn
385                 390                 395                 400
Lys Thr Phe Gln Glu Leu Ala Val Phe His Asp Leu Glu Gly Met Trp
                405                 410                 415
Glu Glu Leu Ser Pro Lys Ile Trp Thr Phe Met Glu Asn Ser Gln Glu
                420                 425                 430
Met Asp Leu Val Arg Met Leu Leu Asp Ser Arg Asp Asn Asp His Phe
                435                 440                 445
Trp Glu Gln Gln Leu Asp Gly Leu Asp Trp Thr Ala Gln Asp Ile Val
        450                 455                 460
Ala Phe Leu Ala Lys His Pro Glu Asp Val Gln Ser Ser Asn Gly Ser
465                 470                 475                 480
Val Tyr Thr Trp Arg Glu Ala Phe Asn Glu Thr Asn Gln Ala Ile Arg
                485                 490                 495
Thr Ile Ser Arg Phe Met Glu Cys Val Asn Leu Asn Lys Leu Glu Pro
                500                 505                 510
Ile Ala Thr Glu Val Trp Leu Ile Asn Lys Ser Met Glu Leu Leu Asp
        515                 520                 525
Glu Arg Lys Phe Trp Ala Gly Ile Val Phe Thr Gly Ile Thr Pro Gly
                530                 535                 540
Ser Ile Glu Leu Pro His His Val Lys Tyr Lys Ile Arg Met Asp Ile
545                 550                 555                 560
Asp Asn Val Glu Arg Thr Asn Lys Ile Lys Asp Gly Tyr Trp Asp Pro
                565                 570                 575
Gly Pro Arg Ala Asp Pro Phe Glu Asp Met Arg Tyr Val Trp Gly Gly
                580                 585                 590
Phe Ala Tyr Leu Gln Asp Val Val Glu Gln Ala Ile Ile Arg Val Leu
                595                 600                 605
Thr Gly Thr Glu Lys Lys Thr Gly Val Tyr Met Gln Gln Met Pro Tyr
        610                 615                 620
Pro Cys Tyr Val Asp Asp Ile Phe Leu Arg Val Met Ser Arg Ser Met
625                 630                 635                 640
Pro Leu Phe Met Thr Leu Ala Trp Ile Tyr Ser Val Ala Val Ile Ile
                645                 650                 655
```

```
Lys Gly Ile Val Tyr Glu Lys Glu Ala Arg Leu Lys Glu Thr Met Arg
            660                 665                 670

Ile Met Gly Leu Asp Asn Ser Ile Leu Trp Phe Ser Trp Phe Ile Ser
        675                 680                 685

Ser Leu Ile Pro Leu Leu Val Ser Ala Gly Leu Leu Val Val Ile Leu
    690                 695                 700

Lys Leu Gly Asn Leu Leu Pro Tyr Ser Asp Pro Ser Val Val Phe Val
705                 710                 715                 720

Phe Leu Ser Val Phe Ala Val Val Thr Ile Leu Gln Cys Phe Leu Ile
                725                 730                 735

Ser Thr Leu Phe Ser Arg Ala Asn Leu Ala Ala Ala Cys Gly Gly Ile
            740                 745                 750

Ile Tyr Phe Thr Leu Tyr Leu Pro Tyr Val Leu Cys Val Ala Trp Gln
        755                 760                 765

Asp Tyr Val Gly Phe Thr Leu Lys Ile Phe Ala Ser Leu Leu Ser Pro
    770                 775                 780

Val Ala Phe Gly Phe Gly Cys Glu Tyr Phe Ala Leu Phe Glu Glu Gln
785                 790                 795                 800

Gly Ile Gly Val Gln Trp Asp Asn Leu Phe Glu Ser Pro Val Glu Glu
                805                 810                 815

Asp Gly Phe Asn Leu Thr Thr Ser Val Ser Met Met Leu Phe Asp Thr
            820                 825                 830

Phe Leu Tyr Gly Val Met Thr Trp Tyr Ile Glu Ala Val Phe Pro Gly
        835                 840                 845

Gln Tyr Gly Ile Pro Arg Pro Trp Tyr Phe Pro Cys Thr Lys Ser Tyr
    850                 855                 860

Trp Phe Gly Glu Glu Ser Asp Glu Lys Ser His Pro Gly Ser Asn Gln
865                 870                 875                 880

Lys Arg Ile Ser Glu Ile Cys Met Glu Glu Glu Pro Thr His Leu Lys
                885                 890                 895

Leu Gly Val Ser Ile Gln Asn Leu Val Lys Val Tyr Arg Asp Gly Met
            900                 905                 910

Lys Val Ala Val Asp Gly Leu Ala Leu Asn Phe Tyr Glu Gly Gln Ile
        915                 920                 925

Thr Ser Phe Leu Gly His Asn Gly Ala Gly Lys Thr Thr Thr Met Ser
    930                 935                 940

Ile Leu Thr Gly Leu Phe Pro Pro Thr Ser Gly Thr Ala Tyr Ile Leu
945                 950                 955                 960

Gly Lys Asp Ile Arg Ser Glu Met Ser Thr Ile Arg Gln Asn Leu Gly
                965                 970                 975

Val Cys Pro Gln His Asn Val Leu Phe Asp Met Leu Thr Val Glu Glu
            980                 985                 990

His Ile Trp Phe Tyr Ala Arg Leu Lys Gly Leu Ser Glu Lys His Val
        995                1000                1005

Lys Ala Glu Met Glu Gln Met Ala Leu Asp Val Gly Leu Pro Ser
    1010                1015                1020

Ser Lys Leu Lys Ser Lys Thr Ser Gln Leu Ser Gly Gly Met Gln
    1025                1030                1035

Arg Lys Leu Ser Val Ala Leu Ala Phe Val Gly Gly Ser Lys Val
    1040                1045                1050

Val Ile Leu Asp Glu Pro Thr Ala Gly Val Asp Pro Tyr Ser Arg
    1055                1060                1065
```

```
Arg Gly Ile Trp Glu Leu Leu Leu Lys Tyr Arg Gln Gly Arg Thr
1070            1075            1080

Ile Ile Leu Ser Thr His His Met Asp Glu Ala Asp Val Leu Gly
1085            1090            1095

Asp Arg Ile Ala Ile Ile Ser His Gly Lys Leu Cys Cys Val Gly
1100            1105            1110

Ser Ser Leu Phe Leu Lys Asn Gln Leu Gly Thr Gly Tyr Tyr Leu
1115            1120            1125

Thr Leu Val Lys Lys Asp Val Glu Ser Ser Leu Ser Ser Cys Arg
1130            1135            1140

Asn Ser Ser Ser Thr Val Ser Tyr Leu Lys Lys Glu Asp Ser Val
1145            1150            1155

Ser Gln Ser Ser Ser Asp Ala Gly Leu Gly Ser Asp His Glu Ser
1160            1165            1170

Asp Thr Leu Thr Ile Asp Val Ser Ala Ile Ser Asn Leu Ile Arg
1175            1180            1185

Lys His Val Ser Glu Ala Arg Leu Val Glu Asp Ile Gly His Glu
1190            1195            1200

Leu Thr Tyr Val Leu Pro Tyr Glu Ala Ala Lys Glu Gly Ala Phe
1205            1210            1215

Val Glu Leu Phe His Glu Ile Asp Asp Arg Leu Ser Asp Leu Gly
1220            1225            1230

Ile Ser Ser Tyr Gly Ile Ser Glu Thr Thr Leu Glu Glu Ile Phe
1235            1240            1245

Leu Lys Val Ala Glu Glu Ser Gly Val Asp Ala Glu Thr Ser Asp
1250            1255            1260

Gly Thr Leu Pro Ala Arg Arg Asn Arg Arg Ala Phe Gly Asp Lys
1265            1270            1275

Gln Ser Cys Leu Arg Pro Phe Thr Glu Asp Asp Ala Ala Asp Pro
1280            1285            1290

Asn Asp Ser Asp Ile Asp Pro Glu Ser Arg Glu Thr Asp Leu Leu
1295            1300            1305

Ser Gly Met Asp Gly Lys Gly Ser Tyr Gln Val Lys Gly Trp Lys
1310            1315            1320

Leu Thr Gln Gln Gln Phe Val Ala Leu Leu Trp Lys Arg Leu Leu
1325            1330            1335

Ile Ala Arg Arg Ser Arg Lys Gly Phe Phe Ala Gln Ile Val Leu
1340            1345            1350

Pro Ala Val Phe Val Cys Ile Ala Leu Val Phe Ser Leu Ile Val
1355            1360            1365

Pro Pro Phe Gly Lys Tyr Pro Ser Leu Glu Leu Gln Pro Trp Met
1370            1375            1380

Tyr Asn Glu Gln Tyr Thr Phe Val Ser Asn Asp Ala Pro Glu Asp
1385            1390            1395

Thr Gly Thr Leu Glu Leu Leu Asn Ala Leu Thr Lys Asp Pro Gly
1400            1405            1410

Phe Gly Thr Arg Cys Met Glu Gly Asn Pro Ile Pro Asp Thr Pro
1415            1420            1425

Cys Gln Ala Gly Glu Glu Glu Trp Thr Thr Ala Pro Val Pro Gln
1430            1435            1440

Thr Ile Met Asp Leu Phe Gln Asn Gly Asn Trp Thr Met Gln Asn
1445            1450            1455

Pro Ser Pro Ala Cys Gln Cys Ser Ser Asp Lys Ile Lys Lys Met
```

-continued

```
              1460                1465              1470

Leu Pro Val Cys Pro Pro Gly Ala Gly Gly Leu Pro Pro Pro Gln
    1475                1480              1485

Arg Lys Gln Asn Thr Ala Asp Ile Leu Gln Asp Leu Thr Gly Arg
    1490                1495              1500

Asn Ile Ser Asp Tyr Leu Val Lys Thr Tyr Val Gln Ile Ile Ala
    1505                1510              1515

Lys Ser Leu Lys Asn Lys Ile Trp Val Asn Glu Phe Arg Tyr Gly
    1520                1525              1530

Gly Phe Ser Leu Gly Val Ser Asn Thr Gln Ala Leu Pro Pro Ser
    1535                1540              1545

Gln Glu Val Asn Asp Ala Ile Lys Gln Met Lys Lys His Leu Lys
    1550                1555              1560

Leu Ala Lys Asp Ser Ser Ala Asp Arg Phe Leu Asn Ser Leu Gly
    1565                1570              1575

Arg Phe Met Thr Gly Leu Asp Thr Lys Asn Asn Val Lys Val Trp
    1580                1585              1590

Phe Asn Asn Lys Gly Trp His Ala Ile Ser Ser Phe Leu Asn Val
    1595                1600              1605

Ile Asn Asn Ala Ile Leu Arg Ala Asn Leu Gln Lys Gly Glu Asn
    1610                1615              1620

Pro Ser His Tyr Gly Ile Thr Ala Phe Asn His Pro Leu Asn Leu
    1625                1630              1635

Thr Lys Gln Gln Leu Ser Glu Val Ala Leu Met Thr Thr Ser Val
    1640                1645              1650

Asp Val Leu Val Ser Ile Cys Val Ile Phe Ala Met Ser Phe Val
    1655                1660              1665

Pro Ala Ser Phe Val Val Phe Leu Ile Gln Glu Arg Val Ser Lys
    1670                1675              1680

Ala Lys His Leu Gln Phe Ile Ser Gly Val Lys Pro Val Ile Tyr
    1685                1690              1695

Trp Leu Ser Asn Phe Val Trp Asp Met Cys Asn Tyr Val Val Pro
    1700                1705              1710

Ala Thr Leu Val Ile Ile Ile Phe Ile Cys Phe Gln Gln Lys Ser
    1715                1720              1725

Tyr Val Ser Ser Thr Asn Leu Pro Val Leu Ala Leu Leu Leu Leu
    1730                1735              1740

Leu Tyr Gly Trp Ser Ile Thr Pro Leu Met Tyr Pro Ala Ser Phe
    1745                1750              1755

Val Phe Lys Ile Pro Ser Thr Ala Tyr Val Val Leu Thr Ser Val
    1760                1765              1770

Asn Leu Phe Ile Gly Ile Asn Gly Ser Val Ala Thr Phe Val Leu
    1775                1780              1785

Glu Leu Phe Thr Asp Asn Lys Leu Asn Asn Ile Asn Asp Ile Leu
    1790                1795              1800

Lys Ser Val Phe Leu Ile Phe Pro His Phe Cys Leu Gly Arg Gly
    1805                1810              1815

Leu Ile Asp Met Val Lys Asn Gln Ala Met Ala Asp Ala Leu Glu
    1820                1825              1830

Arg Phe Gly Glu Asn Arg Phe Val Ser Pro Leu Ser Trp Asp Leu
    1835                1840              1845

Val Gly Arg Asn Leu Phe Ala Met Ala Val Glu Gly Val Val Phe
    1850                1855              1860
```

-continued

```
Phe Leu Ile Thr Val Leu Ile Gln Tyr Arg Phe Phe Ile Arg Pro
    1865                1870                1875

Arg Pro Val Asn Ala Lys Leu Ser Pro Leu Asn Asp Glu Asp Glu
    1880                1885                1890

Asp Val Arg Arg Glu Arg Gln Arg Ile Leu Asp Gly Gly Gly Gln
    1895                1900                1905

Asn Asp Ile Leu Glu Ile Lys Glu Leu Thr Lys Ile Tyr Arg Arg
    1910                1915                1920

Lys Arg Lys Pro Ala Val Asp Arg Ile Cys Val Gly Ile Pro Pro
    1925                1930                1935

Gly Glu Cys Phe Gly Leu Leu Gly Val Asn Gly Ala Gly Lys Ser
    1940                1945                1950

Ser Thr Phe Lys Met Leu Thr Gly Asp Thr Thr Val Thr Arg Gly
    1955                1960                1965

Asp Ala Phe Leu Asn Lys Asn Ser Ile Leu Ser Asn Ile His Glu
    1970                1975                1980

Val His Gln Asn Met Gly Tyr Cys Pro Gln Phe Asp Ala Ile Thr
    1985                1990                1995

Glu Leu Leu Thr Gly Arg Glu His Val Glu Phe Phe Ala Leu Leu
    2000                2005                2010

Arg Gly Val Pro Glu Lys Glu Val Gly Lys Val Gly Glu Trp Ala
    2015                2020                2025

Ile Arg Lys Leu Gly Leu Val Lys Tyr Gly Glu Lys Tyr Ala Gly
    2030                2035                2040

Asn Tyr Ser Gly Gly Asn Lys Arg Lys Leu Ser Thr Ala Met Ala
    2045                2050                2055

Leu Ile Gly Gly Pro Pro Val Val Phe Leu Asp Glu Pro Thr Thr
    2060                2065                2070

Gly Met Asp Pro Lys Ala Arg Arg Phe Leu Trp Asn Cys Ala Leu
    2075                2080                2085

Ser Val Val Lys Glu Gly Arg Ser Val Val Leu Thr Ser His Ser
    2090                2095                2100

Met Glu Glu Cys Glu Ala Leu Cys Thr Arg Met Ala Ile Met Val
    2105                2110                2115

Asn Gly Arg Phe Arg Cys Leu Gly Ser Val Gln His Leu Lys Asn
    2120                2125                2130

Arg Phe Gly Asp Gly Tyr Thr Ile Val Val Arg Ile Ala Gly Ser
    2135                2140                2145

Asn Pro Asp Leu Lys Pro Val Gln Asp Phe Phe Gly Leu Ala Phe
    2150                2155                2160

Pro Gly Ser Val Leu Lys Glu Lys His Arg Asn Met Leu Gln Tyr
    2165                2170                2175

Gln Leu Pro Ser Ser Leu Ser Ser Leu Ala Arg Ile Phe Ser Ile
    2180                2185                2190

Leu Ser Gln Ser Lys Lys Arg Leu His Ile Glu Asp Tyr Ser Val
    2195                2200                2205

Ser Gln Thr Thr Leu Asp Gln Val Phe Val Asn Phe Ala Lys Asp
    2210                2215                2220

Gln Ser Asp Asp Asp His Leu Lys Asp Leu Ser Leu His Lys Asn
    2225                2230                2235

Gln Thr Val Val Asp Val Ala Val Leu Thr Ser Phe Leu Gln Asp
    2240                2245                2250
```

Glu Lys Val Lys Glu Ser Tyr Val
    2255            2260

<210> SEQ ID NO 10
<211> LENGTH: 2261
<212> TYPE: PRT
<213> ORGANISM: HUMAN

<400> SEQUENCE: 10

Met Ala Cys Trp Pro Gln Leu Arg Leu Leu Trp Lys Asn Leu Thr
1               5                   10                  15

Phe Arg Arg Gln Thr Cys Gln Leu Leu Glu Val Ala Trp Pro
            20                  25                  30

Leu Phe Ile Phe Leu Ile Leu Ile Ser Val Arg Leu Ser Tyr Pro Pro
            35                  40                      45

Tyr Glu Gln His Glu Cys His Phe Pro Asn Lys Ala Met Pro Ser Ala
    50                  55                  60

Gly Thr Leu Pro Trp Val Gln Gly Ile Ile Cys Asn Ala Asn Asn Pro
65                  70                  75                  80

Cys Phe Arg Tyr Pro Thr Pro Gly Glu Ala Pro Gly Val Val Gly Asn
                85                  90                  95

Phe Asn Lys Ser Ile Val Ala Arg Leu Phe Ser Asp Ala Arg Arg Leu
            100                 105                 110

Leu Leu Tyr Ser Gln Lys Asp Thr Ser Met Lys Asp Met Arg Lys Val
            115                 120                 125

Leu Arg Thr Leu Gln Gln Ile Lys Lys Ser Ser Asn Leu Lys Leu
        130                 135                 140

Gln Asp Phe Leu Val Asp Asn Glu Thr Phe Ser Gly Phe Leu Tyr His
145                 150                 155                 160

Asn Leu Ser Leu Pro Lys Ser Thr Val Asp Lys Met Leu Arg Ala Asp
                165                 170                 175

Val Ile Leu His Lys Val Phe Leu Gln Gly Tyr Gln Leu His Leu Thr
            180                 185                 190

Ser Leu Cys Asn Gly Ser Lys Ser Glu Glu Met Ile Gln Leu Gly Asp
            195                 200                 205

Gln Glu Val Ser Glu Leu Cys Gly Leu Pro Arg Glu Lys Leu Ala Ala
    210                 215                 220

Ala Glu Arg Val Leu Arg Ser Asn Met Asp Ile Leu Lys Pro Ile Leu
225                 230                 235                 240

Arg Thr Leu Asn Ser Thr Ser Pro Phe Pro Ser Lys Glu Leu Ala Glu
                245                 250                 255

Ala Thr Lys Thr Leu Leu His Ser Leu Gly Thr Leu Ala Gln Glu Leu
            260                 265                 270

Phe Ser Met Arg Ser Trp Ser Asp Met Arg Gln Glu Val Met Phe Leu
            275                 280                 285

Thr Asn Val Asn Ser Ser Ser Ser Thr Gln Ile Tyr Gln Ala Val
    290                 295                 300

Ser Arg Ile Val Cys Gly His Pro Glu Gly Gly Gly Leu Lys Ile Lys
305                 310                 315                 320

Ser Leu Asn Trp Tyr Glu Asp Asn Asn Tyr Lys Ala Leu Phe Gly Gly
                325                 330                 335

Asn Gly Thr Glu Glu Asp Ala Glu Thr Phe Tyr Asp Asn Ser Thr Thr
            340                 345                 350

Pro Tyr Cys Asn Asp Leu Met Lys Asn Leu Glu Ser Ser Pro Leu Ser
            355                 360                 365

-continued

```
Arg Ile Ile Trp Lys Ala Leu Lys Pro Leu Leu Val Gly Lys Ile Leu
        370                 375                 380
Tyr Thr Pro Asp Thr Pro Ala Thr Arg Gln Val Met Ala Glu Val Asn
385                 390                 395                 400
Lys Thr Phe Gln Glu Leu Ala Val Phe His Asp Leu Glu Gly Met Trp
                405                 410                 415
Glu Glu Leu Ser Pro Lys Ile Trp Thr Phe Met Glu Asn Ser Gln Glu
            420                 425                 430
Met Asp Leu Val Arg Met Leu Leu Asp Ser Arg Asp Asn Asp His Phe
        435                 440                 445
Trp Glu Gln Gln Leu Asp Gly Leu Asp Trp Thr Ala Gln Asp Ile Val
    450                 455                 460
Ala Phe Leu Ala Lys His Pro Glu Asp Val Gln Ser Ser Asn Gly Ser
465                 470                 475                 480
Val Tyr Thr Trp Arg Glu Ala Phe Asn Glu Thr Asn Gln Ala Ile Arg
                485                 490                 495
Thr Ile Ser Arg Phe Met Glu Cys Val Asn Leu Asn Lys Leu Glu Pro
            500                 505                 510
Ile Ala Thr Glu Val Trp Leu Ile Asn Lys Ser Met Glu Leu Leu Asp
        515                 520                 525
Glu Arg Lys Phe Trp Ala Gly Ile Val Phe Thr Gly Ile Thr Pro Gly
    530                 535                 540
Ser Ile Glu Leu Pro His His Val Lys Tyr Lys Ile Arg Met Asp Ile
545                 550                 555                 560
Asp Asn Val Glu Arg Thr Asn Lys Ile Lys Asp Gly Tyr Trp Asp Pro
                565                 570                 575
Gly Pro Arg Ala Asp Pro Phe Glu Asp Met Arg Tyr Val Trp Gly Gly
            580                 585                 590
Phe Ala Tyr Leu Gln Asp Val Val Glu Gln Ala Ile Ile Arg Val Leu
        595                 600                 605
Thr Gly Thr Glu Lys Lys Thr Gly Val Tyr Met Gln Gln Met Pro Tyr
    610                 615                 620
Pro Cys Tyr Val Asp Asp Ile Phe Leu Arg Val Met Ser Arg Ser Met
625                 630                 635                 640
Pro Leu Phe Met Thr Leu Ala Trp Ile Tyr Ser Val Ala Val Ile Ile
                645                 650                 655
Lys Gly Ile Val Tyr Glu Lys Glu Ala Arg Leu Lys Glu Thr Met Arg
            660                 665                 670
Ile Met Gly Leu Asp Asn Ser Ile Leu Trp Phe Ser Trp Phe Ile Ser
        675                 680                 685
Ser Leu Ile Pro Leu Leu Val Ser Ala Gly Leu Leu Val Val Ile Leu
    690                 695                 700
Lys Leu Gly Asn Leu Leu Pro Tyr Ser Asp Pro Ser Val Val Phe Val
705                 710                 715                 720
Phe Leu Ser Val Phe Ala Val Val Thr Ile Leu Gln Cys Phe Leu Ile
                725                 730                 735
Ser Thr Leu Phe Ser Arg Ala Asn Leu Ala Ala Ala Cys Gly Gly Ile
            740                 745                 750
Ile Tyr Phe Thr Leu Tyr Leu Pro Tyr Val Leu Cys Val Ala Trp Gln
        755                 760                 765
Asp Tyr Val Gly Phe Thr Leu Lys Ile Phe Ala Ser Leu Leu Ser Pro
    770                 775                 780
```

-continued

Val Ala Phe Gly Phe Gly Cys Glu Tyr Phe Ala Leu Phe Glu Glu Gln
785                 790                 795                 800

Gly Ile Gly Val Gln Trp Asp Asn Leu Phe Glu Ser Pro Val Glu Glu
            805                 810                 815

Asp Gly Phe Asn Leu Thr Thr Ser Val Ser Met Met Leu Phe Asp Thr
            820                 825                 830

Phe Leu Tyr Gly Val Met Thr Trp Tyr Ile Glu Ala Val Phe Pro Gly
            835                 840                 845

Gln Tyr Gly Ile Pro Arg Pro Trp Tyr Phe Pro Cys Thr Lys Ser Tyr
850                 855                 860

Trp Phe Gly Glu Glu Ser Asp Glu Lys Ser His Pro Gly Ser Asn Gln
865                 870                 875                 880

Lys Arg Ile Ser Glu Ile Cys Met Glu Glu Pro Thr His Leu Lys
                885                 890                 895

Leu Gly Val Ser Ile Gln Asn Leu Val Lys Val Tyr Arg Asp Gly Met
            900                 905                 910

Lys Val Ala Val Asp Gly Leu Ala Leu Asn Phe Tyr Glu Gly Gln Ile
        915                 920                 925

Thr Ser Phe Leu Gly His Asn Gly Ala Gly Lys Thr Thr Thr Met Ser
930                 935                 940

Ile Leu Thr Gly Leu Phe Pro Pro Thr Ser Gly Thr Ala Tyr Ile Leu
945                 950                 955                 960

Gly Lys Asp Ile Arg Ser Glu Met Ser Thr Ile Arg Gln Asn Leu Gly
            965                 970                 975

Val Cys Pro Gln His Asn Val Leu Phe Asp Met Leu Thr Val Glu Glu
            980                 985                 990

His Ile Trp Phe Tyr Ala Arg Leu Lys Gly Leu Ser Glu Lys His Val
            995                 1000                1005

Lys Ala Glu Met Glu Gln Met Ala Leu Asp Val Gly Leu Pro Ser
    1010                1015                1020

Ser Lys Leu Lys Ser Lys Thr Ser Gln Leu Ser Gly Gly Met Gln
    1025                1030                1035

Arg Lys Leu Ser Val Ala Leu Ala Phe Val Gly Gly Ser Lys Val
    1040                1045                1050

Val Ile Leu Asp Glu Pro Thr Ala Gly Val Asp Pro Tyr Ser Arg
    1055                1060                1065

Arg Gly Ile Trp Glu Leu Leu Leu Lys Tyr Arg Gln Gly Arg Thr
    1070                1075                1080

Ile Ile Leu Ser Thr His His Met Asp Glu Ala Asp Val Leu Gly
    1085                1090                1095

Asp Arg Ile Ala Ile Ile Ser His Gly Lys Leu Cys Cys Val Gly
    1100                1105                1110

Ser Ser Leu Phe Leu Lys Asn Gln Leu Gly Thr Gly Tyr Tyr Leu
    1115                1120                1125

Thr Leu Val Lys Lys Asp Val Glu Ser Ser Leu Ser Ser Cys Arg
    1130                1135                1140

Asn Ser Ser Ser Thr Val Ser Tyr Leu Lys Lys Glu Asp Ser Val
    1145                1150                1155

Ser Gln Ser Ser Ser Asp Ala Gly Leu Gly Ser Asp His Glu Ser
    1160                1165                1170

Asp Thr Leu Thr Ile Asp Val Ser Ala Ile Ser Asn Leu Ile Arg
    1175                1180                1185

Lys His Val Ser Glu Ala Arg Leu Val Glu Asp Ile Gly His Glu

-continued

```
            1190                1195                1200
Leu Thr Tyr Val Leu Pro Tyr Glu Ala Lys Glu Gly Ala Phe
    1205                1210                1215
Val Glu Leu Phe His Glu Ile Asp Asp Arg Leu Ser Asp Leu Gly
    1220                1225                1230
Ile Ser Ser Tyr Gly Ile Ser Glu Thr Thr Leu Glu Glu Ile Phe
    1235                1240                1245
Leu Lys Val Ala Glu Glu Ser Gly Val Asp Ala Glu Thr Ser Asp
    1250                1255                1260
Gly Thr Leu Pro Ala Arg Arg Asn Arg Arg Ala Phe Gly Asp Lys
    1265                1270                1275
Gln Ser Cys Leu Arg Pro Phe Thr Glu Asp Asp Ala Ala Asp Pro
    1280                1285                1290
Asn Asp Ser Asp Ile Asp Pro Glu Ser Arg Glu Thr Asp Leu Leu
    1295                1300                1305
Ser Gly Met Asp Gly Lys Gly Ser Tyr Gln Val Lys Gly Trp Lys
    1310                1315                1320
Leu Thr Gln Gln Gln Phe Val Ala Leu Leu Trp Lys Arg Leu Leu
    1325                1330                1335
Ile Ala Arg Arg Ser Arg Lys Gly Phe Phe Ala Gln Ile Val Leu
    1340                1345                1350
Pro Ala Val Phe Val Cys Ile Ala Leu Val Phe Ser Leu Ile Val
    1355                1360                1365
Pro Pro Phe Gly Lys Tyr Pro Ser Leu Glu Leu Gln Pro Trp Met
    1370                1375                1380
Tyr Asn Glu Gln Tyr Thr Phe Val Ser Asn Asp Ala Pro Glu Asp
    1385                1390                1395
Thr Gly Thr Leu Glu Leu Leu Asn Ala Leu Thr Lys Asp Pro Gly
    1400                1405                1410
Phe Gly Thr Arg Cys Met Glu Gly Asn Pro Ile Pro Asp Thr Pro
    1415                1420                1425
Cys Gln Ala Gly Glu Glu Glu Trp Thr Thr Ala Pro Val Pro Gln
    1430                1435                1440
Thr Ile Met Asp Leu Phe Gln Asn Gly Asn Trp Thr Met Gln Asn
    1445                1450                1455
Pro Ser Pro Ala Cys Gln Cys Ser Ser Asp Lys Ile Lys Lys Met
    1460                1465                1470
Leu Pro Val Cys Pro Pro Gly Ala Gly Gly Leu Pro Pro Pro Gln
    1475                1480                1485
Arg Lys Gln Asn Thr Ala Asp Ile Leu Gln Asp Leu Thr Gly Arg
    1490                1495                1500
Asn Ile Ser Asp Tyr Leu Val Lys Thr Tyr Val Gln Ile Ile Ala
    1505                1510                1515
Lys Ser Leu Lys Asn Lys Ile Trp Val Asn Glu Phe Arg Tyr Gly
    1520                1525                1530
Gly Phe Ser Leu Gly Val Ser Asn Thr Gln Ala Leu Pro Pro Ser
    1535                1540                1545
Gln Glu Val Asn Asp Ala Ile Lys Gln Met Lys Lys His Leu Lys
    1550                1555                1560
Leu Ala Lys Asp Ser Ser Ala Asp Arg Phe Leu Asn Ser Leu Gly
    1565                1570                1575
Arg Phe Met Thr Gly Leu Asp Thr Lys Asn Asn Val Lys Val Trp
    1580                1585                1590
```

-continued

Phe Asn Asn Lys Gly Trp His Ala Ile Ser Ser Phe Leu Asn Val
1595                1600                1605

Ile Asn Asn Ala Ile Leu Arg Ala Asn Leu Gln Lys Gly Glu Asn
1610                1615                1620

Pro Ser His Tyr Gly Ile Thr Ala Phe Asn His Pro Leu Asn Leu
1625                1630                1635

Thr Lys Gln Gln Leu Ser Glu Val Ala Leu Met Thr Thr Ser Val
1640                1645                1650

Asp Val Leu Val Ser Ile Cys Val Ile Phe Ala Met Ser Phe Val
1655                1660                1665

Pro Ala Ser Phe Val Val Phe Leu Ile Gln Glu Arg Val Ser Lys
1670                1675                1680

Ala Lys His Leu Gln Phe Ile Ser Gly Val Lys Pro Val Ile Tyr
1685                1690                1695

Trp Leu Ser Asn Phe Val Trp Asp Met Cys Asn Tyr Val Val Pro
1700                1705                1710

Ala Thr Leu Val Ile Ile Ile Phe Ile Cys Phe Gln Gln Lys Ser
1715                1720                1725

Tyr Val Ser Ser Thr Asn Leu Pro Val Leu Ala Leu Leu Leu Leu
1730                1735                1740

Leu Tyr Gly Trp Ser Ile Thr Pro Leu Met Tyr Pro Ala Ser Phe
1745                1750                1755

Val Phe Lys Ile Pro Ser Thr Ala Tyr Val Val Leu Thr Ser Val
1760                1765                1770

Asn Leu Phe Ile Gly Ile Asn Gly Ser Val Ala Thr Phe Val Leu
1775                1780                1785

Glu Leu Phe Thr Asp Asn Lys Leu Asn Asn Ile Asn Asp Ile Leu
1790                1795                1800

Lys Ser Val Phe Leu Ile Phe Pro His Phe Cys Leu Gly Arg Gly
1805                1810                1815

Leu Ile Asp Met Val Lys Asn Gln Ala Met Ala Asp Ala Leu Glu
1820                1825                1830

Arg Phe Gly Glu Asn Arg Phe Val Ser Pro Leu Ser Trp Asp Leu
1835                1840                1845

Val Gly Arg Asn Leu Phe Ala Met Ala Val Glu Gly Val Val Phe
1850                1855                1860

Phe Leu Ile Thr Val Leu Ile Gln Tyr Arg Phe Phe Ile Arg Pro
1865                1870                1875

Arg Pro Val Asn Ala Lys Leu Ser Pro Leu Asn Asp Glu Asp Glu
1880                1885                1890

Asp Val Arg Arg Glu Arg Gln Arg Ile Leu Asp Gly Gly Gly Gln
1895                1900                1905

Asn Asp Ile Leu Glu Ile Lys Glu Leu Thr Lys Ile Tyr Arg Arg
1910                1915                1920

Lys Arg Lys Pro Ala Val Asp Arg Ile Cys Val Gly Ile Pro Pro
1925                1930                1935

Gly Glu Cys Phe Gly Leu Leu Gly Val Asn Gly Ala Gly Lys Ser
1940                1945                1950

Ser Thr Phe Lys Met Leu Thr Gly Asp Thr Thr Val Thr Arg Gly
1955                1960                1965

Asp Ala Phe Leu Asn Lys Asn Ser Ile Leu Ser Asn Ile His Glu
1970                1975                1980

| | | | | | | | | | | |
|---|---|---|---|---|---|---|---|---|---|---|
| Val | His | Gln | Asn | Met | Gly | Tyr | Cys | Pro | Gln | Phe | Asp | Ala | Ile | Thr |
| | 1985 | | | | 1990 | | | | | 1995 | | | | |

Val His Gln Asn Met Gly Tyr Cys Pro Gln Phe Asp Ala Ile Thr
     1985               1990                  1995

Glu Leu Leu Thr Gly Arg Glu His Val Glu Phe Phe Ala Leu Leu
     2000               2005                  2010

Arg Gly Val Pro Glu Lys Glu Val Gly Lys Val Gly Glu Trp Ala
     2015               2020                  2025

Ile Arg Lys Leu Gly Leu Val Lys Tyr Gly Glu Lys Tyr Ala Gly
     2030               2035                  2040

Asn Tyr Ser Gly Gly Asn Lys Arg Lys Leu Ser Thr Ala Met Ala
     2045               2050                  2055

Leu Ile Gly Gly Pro Pro Val Phe Leu Asp Glu Pro Thr Thr
     2060               2065                  2070

Gly Met Asp Pro Lys Ala Arg Arg Phe Leu Trp Asn Cys Ala Leu
     2075               2080                  2085

Ser Val Val Lys Glu Gly Arg Ser Val Val Leu Thr Ser His Ser
     2090               2095                  2100

Met Glu Glu Cys Glu Ala Leu Cys Thr Arg Met Ala Ile Met Val
     2105               2110                  2115

Asn Gly Arg Phe Arg Cys Leu Gly Ser Val Gln His Leu Lys Asn
     2120               2125                  2130

Arg Phe Gly Asp Gly Tyr Thr Ile Val Val Arg Ile Ala Gly Ser
     2135               2140                  2145

Asn Pro Asp Leu Lys Pro Val Gln Asp Phe Phe Gly Leu Ala Phe
     2150               2155                  2160

Pro Gly Ser Val Leu Lys Glu Lys His Arg Asn Met Leu Gln Tyr
     2165               2170                  2175

Gln Leu Pro Ser Ser Leu Ser Ser Leu Ala Arg Ile Phe Ser Ile
     2180               2185                  2190

Leu Ser Gln Ser Lys Lys Arg Leu His Ile Glu Asp Tyr Ser Val
     2195               2200                  2205

Ser Gln Thr Thr Leu Asp Gln Val Phe Val Asn Phe Ala Lys Asp
     2210               2215                  2220

Gln Ser Asp Asp Asp His Leu Lys Asp Leu Ser Leu His Lys Asn
     2225               2230                  2235

Gln Thr Val Val Asp Val Ala Val Leu Thr Ser Phe Leu Gln Asp
     2240               2245                  2250

Glu Lys Val Lys Glu Ser Tyr Val
     2255               2260

<210> SEQ ID NO 11
<211> LENGTH: 2566
<212> TYPE: DNA
<213> ORGANISM: HUMAN

<400> SEQUENCE: 11
cgtcgccgtc cccgtctcct gccaggcgcg gagccctgcg agccgcgggt gggccccagg     60
cgcgcagaca tgggctgctc cgccaaagcg cgctgggctg ccggggcgct gggcgtcgcg   120
gggctactgt gcgctgtgct gggcgctgtc atgatcgtga tggtgccgtc gctcatcaag   180
cagcaggtcc ttaagaacgt gcgcatcgac cccagtagcc tgtccttcaa catgtggaag   240
gagatcccta tccccttcta tctctccgtc tacttctttg acgtcatgaa ccccagcgag   300
atcctgaagg gcgagaagcc gcaggtgcgg gagcgcgggc cctacgtgta cagggagtcc   360
aggcacaaaa gcaacatcac cttcaacaac aacgacaccg tgtccttcct cgagtaccgc   420

| | |
|---|---|
| accttccagt tccagccctc caagtcccac ggctcggaga gcgactacat cgtcatgccc | 480 |
| aacatcctgg tcttgggtgc ggcggtgatg atggagaata agcccatgac cctgaagctc | 540 |
| atcatgacct tggcattcac caccctcggc gaacgtgcct tcatgaaccg cactgtgggt | 600 |
| gagatcatgt ggggctacaa ggacccccctt gtgaatctca tcaacaagta ctttccaggc | 660 |
| atgttcccct tcaaggacaa gttcggatta tttgctgagc tcaacaactc cgactctggg | 720 |
| ctcttcacgg tgttcacggg ggtccagaac atcagcagga tccacctcgt ggacaagtgg | 780 |
| aacgggctga gcaaggttga cttctggcat tccgatcagt gcaacatgat caatggaact | 840 |
| tctgggcaaa tgtggccgcc cttcatgact cctgagtcct cgctggagtt ctacagcccg | 900 |
| gaggcctgcc gatccatgaa gctaatgtac aaggagtcag gggtgtttga aggcatcccc | 960 |
| acctatcgct tcgtggctcc caaaaccctg tttgccaacg ggtccatcta cccacccaac | 1020 |
| gaaggcttct gcccgtgcct ggagtctgga attcagaacg tcagcacctg caggttcagt | 1080 |
| gccccccttgt ttctctccca tcctcacttc ctcaacgccg accggttcct ggcagaagcg | 1140 |
| gtgactggcc tgcaccctaa ccaggaggca cactccttgt tcctggacat ccacccggtc | 1200 |
| acgggaatcc ccatgaactg ctctgtgaaa ctgcagctga gcctctacat gaaatctgtc | 1260 |
| gcaggcattg acaaactgg gaagattgag cctgtggtcc tgccgctgct ctggtttgca | 1320 |
| gagagcgggg ccatggaggg ggagactctt cacacattct acactcagct ggtgttgatg | 1380 |
| cccaaggtga tgcactatgc ccagtacgtc ctcctggcgc tgggctgcgt cctgctgctg | 1440 |
| gtccctgtca tctgccaaat ccggagccaa gagaaatgct atttattttg gagtagtagt | 1500 |
| aaaaagggct caaaggataa ggaggccatt caggcctatt ctgaatccct gatgacatca | 1560 |
| gctcccaagg gctctgtgct gcaggaagca aaactgtagg gtcctgagga caccgtgagc | 1620 |
| cagccaggcc tggccgctgg gcctgaccgg cccccccagcc cctacacccc gcttctcccg | 1680 |
| gactctccca gcagacagcc ccccagcccc acagcctgag cctcccagct gccatgtgcc | 1740 |
| tgttgcacac ctgcacacac gccctggcac acatacacac atgcgtgcag gcttgtgcag | 1800 |
| acactcaggg atggagctgc tgctgaaggg acttgtaggg agaggctcgt caacaagcac | 1860 |
| tgttctggaa ccttctctcc acgtggccca caggctgacc acaggggctg tgggtcctgc | 1920 |
| gtccccttcc tcgggtgagc ctggcctgtc ccgttcagcc gttgggccag gcttcctccc | 1980 |
| ctccaaggtg aaacactgca gtcccggtgt ggtggctccc catgcaggac gggccaggct | 2040 |
| gggagtgccg ccttcctgtg ccaaattcag tggggactca gtgccaggcc ctggcacga | 2100 |
| gctttggcct tggtctacct gccaggccag gcaaagcgcc tttacacagg cctcggaaaa | 2160 |
| caatggagtg agcacaagat gcccgtgcca gctgcccgag ggtctccgcc caccccggcc | 2220 |
| ggactttgat ccccccgaag tcttcacagg cactgcatcg ggttgtctgg cgcccttttc | 2280 |
| ctccagccta aactgacatc atcctatgga ctgagccggc cactctctgg ccgaagtggc | 2340 |
| gcaggctgtg cccccgagct gccccacccc cctcacaggg tccctcagat tataggtgcc | 2400 |
| caggctgagg tgaagaggcc tgggggccct gccttccggg cgctcctgga ccctggggca | 2460 |
| aacctgtgac ccttttctac tggaatagaa atgagtttta tcatctttga aaaataattc | 2520 |
| actcttgaag taataaacgt ttaaaaaaat ggaaaaaaaa aaaaaa | 2566 |

<210> SEQ ID NO 12
<211> LENGTH: 509
<212> TYPE: PRT
<213> ORGANISM: HUMAN

<400> SEQUENCE: 12

-continued

```
Met Gly Cys Ser Ala Lys Ala Arg Trp Ala Gly Ala Leu Gly Val
 1               5                  10                 15

Ala Gly Leu Leu Cys Ala Val Leu Gly Ala Val Met Ile Val Met Val
                20                  25                  30

Pro Ser Leu Ile Lys Gln Gln Val Leu Lys Asn Val Arg Ile Asp Pro
             35                  40                  45

Ser Ser Leu Ser Phe Asn Met Trp Lys Glu Ile Pro Ile Pro Phe Tyr
 50                  55                  60

Leu Ser Val Tyr Phe Phe Asp Val Met Asn Pro Ser Glu Ile Leu Lys
 65                  70                  75                  80

Gly Glu Lys Pro Gln Val Arg Glu Arg Gly Pro Tyr Val Tyr Arg Glu
                 85                  90                  95

Ser Arg His Lys Ser Asn Ile Thr Phe Asn Asn Asp Thr Val Ser
                100                 105                 110

Phe Leu Glu Tyr Arg Thr Phe Gln Phe Gln Pro Ser Lys Ser His Gly
            115                 120                 125

Ser Glu Ser Asp Tyr Ile Val Met Pro Asn Ile Leu Val Leu Gly Ala
            130                 135                 140

Ala Val Met Met Glu Asn Lys Pro Met Thr Leu Lys Leu Ile Met Thr
145                 150                 155                 160

Leu Ala Phe Thr Thr Leu Gly Glu Arg Ala Phe Met Asn Arg Thr Val
                165                 170                 175

Gly Glu Ile Met Trp Gly Tyr Lys Asp Pro Leu Val Asn Leu Ile Asn
                180                 185                 190

Lys Tyr Phe Pro Gly Met Phe Pro Phe Lys Asp Lys Phe Gly Leu Phe
            195                 200                 205

Ala Glu Leu Asn Asn Ser Asp Ser Gly Leu Phe Thr Val Phe Thr Gly
            210                 215                 220

Val Gln Asn Ile Ser Arg Ile His Leu Val Asp Lys Trp Asn Gly Leu
225                 230                 235                 240

Ser Lys Val Asp Phe Trp His Ser Asp Gln Cys Asn Met Ile Asn Gly
                245                 250                 255

Thr Ser Gly Gln Met Trp Pro Pro Phe Met Thr Pro Glu Ser Ser Leu
                260                 265                 270

Glu Phe Tyr Ser Pro Glu Ala Cys Arg Ser Met Lys Leu Met Tyr Lys
            275                 280                 285

Glu Ser Gly Val Phe Glu Gly Ile Pro Thr Tyr Arg Phe Val Ala Pro
            290                 295                 300

Lys Thr Leu Phe Ala Asn Gly Ser Ile Tyr Pro Pro Asn Glu Gly Phe
305                 310                 315                 320

Cys Pro Cys Leu Glu Ser Gly Ile Gln Asn Val Ser Thr Cys Arg Phe
                325                 330                 335

Ser Ala Pro Leu Phe Leu Ser His Pro His Phe Leu Asn Ala Asp Pro
                340                 345                 350

Val Leu Ala Glu Ala Val Thr Gly Leu His Pro Asn Gln Glu Ala His
            355                 360                 365

Ser Leu Phe Leu Asp Ile His Pro Val Thr Gly Ile Pro Met Asn Cys
370                 375                 380

Ser Val Lys Leu Gln Leu Ser Leu Tyr Met Lys Ser Val Ala Gly Ile
385                 390                 395                 400

Gly Gln Thr Gly Lys Ile Glu Pro Val Val Leu Pro Leu Leu Trp Phe
                405                 410                 415
```

```
Ala Glu Ser Gly Ala Met Glu Gly Glu Thr Leu His Thr Phe Tyr Thr
            420                 425                 430

Gln Leu Val Leu Met Pro Lys Val Met His Tyr Ala Gln Tyr Val Leu
        435                 440                 445

Leu Ala Leu Gly Cys Val Leu Leu Val Pro Val Ile Cys Gln Ile
        450                 455                 460

Arg Ser Gln Glu Lys Cys Tyr Leu Phe Trp Ser Ser Lys Gly
465                 470                 475                 480

Ser Lys Asp Lys Glu Ala Ile Gln Ala Tyr Ser Glu Ser Leu Met Thr
                485                 490                 495

Ser Ala Pro Lys Gly Ser Val Leu Gln Glu Ala Lys Leu
                500                 505
```

<210> SEQ ID NO 13
<211> LENGTH: 25
<212> TYPE: DNA
<213> ORGANISM: ARTIFICIAL SEQUENCE
<220> FEATURE:
<223> OTHER INFORMATION: Primer

<400> SEQUENCE: 13
taagcttggc acggctgtcc aagga                                    25

<210> SEQ ID NO 14
<211> LENGTH: 26
<212> TYPE: DNA
<213> ORGANISM: ARTIFICIAL SEQUENCE
<220> FEATURE:
<223> OTHER INFORMATION: Primer

<400> SEQUENCE: 14
acagaattcg ccccggcctg gtacac                                   26

<210> SEQ ID NO 15
<211> LENGTH: 18
<212> TYPE: PRT
<213> ORGANISM: ARTIFICIAL SEQUENCE
<220> FEATURE:
<223> OTHER INFORMATION: Synthetic Peptide

<400> SEQUENCE: 15

```
Asp Trp Leu Lys Ala Phe Tyr Asp Lys Val Ala Glu Lys Leu Lys Glu
1               5                   10                  15

Ala Phe
```

<210> SEQ ID NO 16
<211> LENGTH: 18
<212> TYPE: PRT
<213> ORGANISM: ARTIFICIAL SEQUENCE
<220> FEATURE:
<223> OTHER INFORMATION: Peptide

<400> SEQUENCE: 16

```
Asp Trp Phe Lys Ala Phe Tyr Asp Lys Val Ala Glu Lys Phe Lys Glu
1               5                   10                  15

Ala Phe
```

<210> SEQ ID NO 17
<211> LENGTH: 67
<212> TYPE: PRT
<213> ORGANISM: ARTIFICIAL SEQUENCE
<220> FEATURE:
<223> OTHER INFORMATION: Peptide

```
<400> SEQUENCE: 17

Leu Ser Pro Leu Gly Glu Glu Met Arg Asp Arg Ala Arg Ala His Val
1               5                   10                  15

Asp Ala Leu Arg Thr His Leu Ala Pro Tyr Ser Asp Glu Leu Arg Gln
            20                  25                  30

Pro Leu Ala Ala Arg Leu Glu Ala Leu Lys Glu Asn Gly Gly Ala Arg
        35                  40                  45

Leu Ala Glu Tyr His Ala Lys Ala Thr Glu His Leu Ser Thr Leu Ser
    50                  55                  60

Glu Lys Ala
65
```

TREATMENT FOR DARK ADAPTATION

CROSS-REFERENCE TO RELATED APPLICATIONS

The present invention is a divisional application of U.S. Nonprovisional patent application Ser. No. 10/794,198, filed Mar. 5, 2004, which is a continuation-in-part of U.S. Nonprovisional patent application Ser. No. 10/428,551, filed May 2, 2003, which is a continuation-in-part of U.S. Nonprovisional patent application Ser. No. 10/313,641, filed Dec. 6, 2002, which claims priority to U.S. Provisional Patent Application 60/340,498, filed Dec. 7, 2001; and U.S. Provisional Patent Application 60/415,864, filed Oct. 3, 2002, all of which are incorporated by reference herein in their entirety.

FIELD OF THE INVENTION

The present invention is directed to the fields of ophthalmology and cell biology. Specifically, the invention regards increasing reverse cholesterol transport in the retinal pigment epithelium and Bruch's membrane. More specifically, the invention relates to treatment of age-related macular degeneration (AMD) utilizing regulation of reverse cholesterol transport.

BACKGROUND OF THE INVENTION

Age-related macular degeneration (AMD) is the leading cause of severe visual loss in the developed world (Taylor et al., 2001; VanNewkirk et al., 2000). In the early stages of the disease, before visual loss occurs from choroidal neovascularization, there is progressive accumulation of lipids in Bruch's membrane (Pauleikhoff et al., 1990; Holz et al., 1994; Sheraidah et al., 1993; Spaide et al., 1999). Bruch's membrane lies at the critical juncture between the outer retina and its blood supply, the choriocapillaris. Lipid deposition causes reduced hydraulic conductivity and macromolecular permeability in Bruch's membrane and is thought to impair retinal metabolism (Moore et al., 1995; Pauleikhoff et al., 1990; Starita et al., 1996). Retina and/or RPE may respond by elaboration of angiogenic factors (e.g. VEGF, vFGF) that promote growth of choroidal neovascularization.

Interestingly, lipid accumulation in Bruch's membrane similar to that in AMD has been observed in apolipoprotein E (apo E) null mice (Dithmar et al., 2000; Kliffen et al., 2000). Because of the additional association between apo E alleles and other age-related degenerations, Alzheimer's disease and atherosclerosis, there has been recent investigation into a potential role for apo E in AMD.

Several studies on apo E polymorphism in AMD have been conducted (Simonelli et al., 2001; Klaver et al., 1998; Souied et al., 1998). In contrast to Alzheimer's disease, the apo E-4 allele has been associated with reduced prevalence of AMD. Apo E-2 allele is slightly increased in patients with AMD. Further supporting a role in AMD pathogenesis, apo E has been detected in drusen, the Bruch's membrane deposits that are the hallmark of AMD (Klaver et al., 1998; Anderson et al., 2001). Immunohistochemistry on post-mortem eyes has demonstrated apo E in the basal aspect of the retinal pigment epithelium (RPE) (Anderson et al., 2001). Cultured RPE cells synthesize high levels of apo E mRNA, comparable to levels found in brain (Anderson et al., 2001).

While the role of apo E in AMD is not established, this apolipoprotein has several functions that may affect the course of this disease. Apo E has anti-angiogenic (Browning et al., 1994), anti-inflammatory (Michael et al., 1994), and anti-oxidative effects (Tangirala et al., 2001). These are all considered atheroprotective attributes of Apo E, but may also be important in protecting against progression of AMD. While atheroprotective effects of apo E were initially thought to stem from effects on plasma lipid levels, local effects on vascular macrophages are probably equally important. Thus, selective enhanced expression of macrophage apo E in the arterial wall reduces atherosclerosis in spite of hyperlipidemia (Shimano et al., 1995; Bellosta et al., 1995; Hasty et al., 1999). Conversely, reconstitution of apo E null macrophages in C57BL/6 wild type mice induces atherosclerosis (Fazio et al., 1994). Atheroprotective effects of arterial apo E expression are thought to derive in part from facilitation of reverse cholesterol transport (Mazzone et al., 1992; Lin et al., 1999). The mechanisms by which apo E facilitates reverse cholesterol transport are incompletely understood. Apo E expression increases cholesterol efflux to HDL3 in J774 macrophages (Mazzone and Reardon, 1994) and lipid free apolipoprotein A1 (Langer et al., 2000). Cell surface apo E is also hypothesized to induce efflux from the plasma membrane (Lin et al., 1999).

Reverse cholesterol transport may be important in the pathogenesis of AMD because of lipid efflux from RPE into Bruch's membrane. Very much like intimal macrophages, RPE cells progressively accumulate lipid deposits throughout life; however, unlike vessel wall macrophages, the source of RPE lipid is thought to be retinal photoreceptor outer segments (POS) (Kennedy et al., 1995). Every day, each RPE cell phagocytoses and degrades more than one thousand POS via lyzosmal enzymes. These POS are enriched in phospholipid and contain the photoreactive pigment, rhodopsin. Incompletely digested POS accumulate as lipofuscin in RPE. By age 80, approximately 20% of RPE cell volume is occupied by lipofuscin (Feeney-Burns et al., 1984).

Analysis of Bruch's membrane lipid reveals an age-related accumulation of phospholipid, triglyceride, cholesterol, and cholesterol ester (Holz et al., 1994; Curcio et al., 2001). The origin of these lipids also is thought to derive principally from POS rather than from the circulation (Holz et al., 1994; Spaide et al., 1999). POS lipids are hypothesized to efflux from the RPE into Bruch's membrane. Although cholesterol ester deposition in Bruch's suggests contribution from plasma lipids, biochemical analysis of these esters suggests esterification of intracellular cholesterol by RPE cell derived ACAT (Curcio et al., 2002). While trafficking of lipids from the retina to RPE cells has been studied extensively, mechanisms of lipid efflux from RPE to Bruch's membrane are not well understood. Furthermore, from a pathogenic standpoint, regulation of lipid efflux into Bruch's membrane may be important in determining the rate of lipid-induced thickening that occurs in aging.

In AS, similar to AMD, lipids accumulate in the extracellular matrix and within phagocytic cells, primarily macrophages. Mechanisms of lipid metabolism in AS have been investigated in detail. Similar investigations into lipid processing by RPE and subsequent lipid efflux into BM and the circulation have not been conducted with the same depth as those for AS. As a consequence, potential therapeutic approaches to dry AMD are wonting.

Navab et al. (2003) describe ApoA-I mimetic peptides comprising D-amino acids for oral delivery for the treatment of atherosclerosis.

U.S. Patent Application Publication US 2002/0142953 relates to human compositions encoding apolipoproteins that are related to lipid metabolism and cardiovascular disease.

Thus, the present invention provides a novel approach to reduce lipid content of ocular tissue, such as Bruch's membrane and further provides methods and compositions for the treatment of macular degeneration, such as AMD.

SUMMARY OF THE INVENTION

In the present invention, there are methods and compositions that relate to increasing reverse cholesterol transport in the retinal pigment epithelium (RPE). Particularly, the increase in reverse cholesterol transport is mediated, enhanced, facilitated, and/or triggered by administration of a composition. More particularly, one or more compositions promote efflux of lipids from Bruch's membrane and/or enhances binding of effluxed lipids from Bruch's membrane, thereby reducing accumulation of lipids in both retinal pigment epithelium and Bruch's membrane. This is beneficial in these regions, given that in aging Bruch's membrane, there is progressive accumulation of lipid and cross-linked protein that impedes hydraulic conductivity and macromolecular permeability. This abnormal deposition, in specific embodiments, also impairs the ability of some larger molecular weight species of HDL, a preferred cholesterol and phospholipids acceptor for lipids effluxed by cultured human RPE, to act as a lipoprotein acceptor. As HDL is unable to pass through BM and promote efflux and/or bind effluxed lipids, more lipids accumulate in both RPE and BM. A skilled artisan recognizes that such accumulations are a major finding in age-related macular degeneration (AMD), and, therefore, recognizes the need for novel compositions for the treatment of this debilitating disease.

Apolipoprotein A1 (ApoA-I) is the major lipoprotein component of HDL, and it has a mass of approximately 28 kDaltons. ApoA-I bound to phospholipids comprises nascent HDL particles that bind to ABCA1 on the RPE basal membrane and promote lipid efflux. Because of the low molecular weight of ApoA-I, it can penetrate an aged BM more easily than larger molecular weight species of HDL to bind to the RPE. In addition to its role in promoting reverse cholesterol transport from RPE, ApoA-I also is a potent anti-oxidant, which is known to reduce visual loss in patients with AMD.

In some embodiments, the present invention is directed to a system, method, and/or composition(s) related to treating AMD. Treatments for dry AMD have been lacking, because the pathogenesis of this common condition is poorly understood, and the inventors have demonstrated analogous biological behavior between human retinal pigment epithelial (RPE) cells and macrophages that point toward similar pathogenic mechanisms of AMD and atherosclerosis. Specifically, reverse cholesterol transport (RCT) is exploited in the present invention for the treatment of AMD. The present inventors provide the novel demonstration of RCT in RPE cells in the eye. More specifically, RCT is regulated through manipulation of levels of cholesterol and/or phospholipid transporters (ABCA-1, Apo E, SRB-1, SRB-2) by nuclear hormone receptor ligands such as agonists of thyroid hormone (TR), liver X receptor (LXR), and/or retinoid X receptor (RXR). A goal for the present invention is the reduction of lipid content of RPE Bruch's membrane to facilitate an improvement in visual function and/or, in some embodiments, prevent ocular disease, such as AMD. Reduction of the lipid content of Bruch's membrane preferably results in at least one or more of the following: reduction in development of CNV; improvement in dark adaptation; improvement in night vision; improved visual acuity; and/or improved recovery to bright flash stimulus.

In an additional embodiment of the present invention, there is a method of treating macular degeneration (AMD) in an individual, comprising the step of delivering to the individual a therapeutically effective amount of an ApoA-I composition. In a specific embodiment, the delivering occurs under conditions wherein reverse cholesterol transport is upregulated, wherein lipid accumulations in BM or RPE are reduced, wherein efflux of lipids from BM is increased, and/or wherein therapeutic anti-oxidant applications are achieved. In further specific embodiments, the administration of the ApoA-I composition results in effective treatment for AMD or any ocular disease, such as be ameliorating at least one symptom of the disease. Delivery of the ApoA-I composition may occur by any method in the art so long as it provides a therapeutically effective amount to the tissue or tissues in need thereof. The delivery may be local or systemic. In preferred embodiments, the delivery is intravenously, as has been done for ApoA-I in mouse models of atherosclerosis and in patients with coronary artery disease. In other embodiments, the delivery is oral.

In particular aspects of the invention, the ApoA-I composition may be any ApoA-I composition that upon delivery to an individual suffering from an ocular disease such as AMD, said disease has amelioration of at least one symptom. For example, the ApoA-I composition may be comprised of one or more L-amino acids or one or more D-amino acids, or mixtures thereof. In particular embodiments, there is an ApoA-I mimetic peptide comprised of D-amino acids, which is not recognized as readily by human proteases, and thus can be administered orally. In specific embodiments, this is more convenient than parenteral administration with an intravenous formulation comprising the L-amino acid ApoA-I or its mimetic peptide. In specific embodiments, exemplary mimetic ApoA-I peptides are used, such as are described by Navab et al. (2003), incorporated by reference herein in its entirety.

By way of example, patients with AMD (atrophic or exudative) are administered an ApoA-I composition, such as intravenous ApoA-I, ApoA-I mimetic peptide, or compositions that increase circulating ApoA-I, such as the exemplary oral synthetic phospholipid (1,2 Dimyristoyl-sn-glycero-3-phosphocholine) (DMPC). Administration could occur in any frequency so long as there is at least one therapeutic effect, and in preferred embodiments the effect is detectable. The administration, in specific but exemplary embodiments, is as frequent as daily or less frequently as in every other month depending on the method of administration and the clinical response.

In another embodiment of the present invention, there is a kit for the treatment of macular degeneration, housed in a suitable container, comprising a ApoA-I composition. In particular embodiments, the ApoA-I composition may be ApoA-I from any organism, but particularly human ApoA-I, a mimetic ApoA-I peptide, or an agent that increases ApoA-I ciruculating levels, such as DMPC. In a specific embodiment, the kit comprises a pharmaceutically acceptable excipient. In another specific embodiment, the ApoA-I composition is comprised in the pharmaceutically acceptable excipient. In other specific embodiments, the ApoA-I composition is comprised in a liposome and delivered orally to an individual.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

I. Definitions

Figure 1:
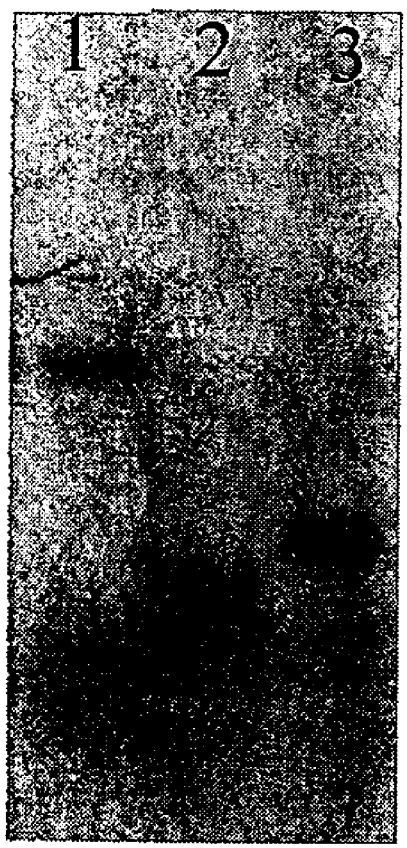
FIG. 1 shows that RPE cells express Apo E, ABCA1, and LXR α.

As used herein the specification, "a" or "an" may mean one or more. As used herein in the claim(s), when used in conjunction with the word "comprising", the words "a" or "an" may mean one or more than one. As used herein "another" may mean at least a second or more.

The term "age-related macular degeneration" as used herein refers to macular degeneration in an individual over the age of about 50. In one specific embodiment, it is associated with destruction and loss of the photoreceptors in the macula region of the retina resulting in decreased central vision and, in advanced cases, legal blindness.

The term "Bruch's membrane" as used herein refers to a five-layered structure separating the choriocapillaris from the RPE.

The term "HDL or subspecies thereof" refers to the fact that high density lipoproteins (HDL) can be fractionated into particulate species defined in molecular size and composition. HDL as prepared by density ultracentrifugation and by native nondenaturing purification processes including anti-apolipoprotein A-I immunoaffinity chromatography have been characterized for its constituent species by two-dimensional nondenaturing polyacrylamide electrophoresis, immunoblotting, and mass spectroscopy. HDL has been resolved into more than twenty-five particle species that differ in charge and molecular size. Each particle is defined by a unique combination of protein (including apolipoproteins A-I, A-II, A-IV, A-V, C-III, D, E, J, L, lecithin:cholesterol acyltransferase, cholesterol ester transferase, phospholipid transfer protein, alpha-2 macroglobulin) and lipid (including phospholipid, triglyceride, cholesterol, cholesterol ester, fatty acids). A partial list of HDL species include HDL alpha-1, HDL alpha-2, HDL alpha-3, HDL prebeta-1, HDL prebeta-2 (and variants "a", "b", "c", "d"), HDL prebeta-3, HDL prebeta-4, and HDL prealpha-1.

The term "increase lipid efflux" or "increasing lipid efflux" as used herein refers to an increased level and/or rate of lipid efflux, promoting lipid efflux, enhancing lipid efflux, facilitating lipid efflux, upregulating lipid efflux, improving lipid efflux, and/or augmenting lipid efflux. In a specific embodiment, the efflux comprises efflux of phospholipid, triglyceride, cholesterol, and/or cholesterol ester.

A skilled artisan recognizes that the term "lipid transporter" as used herein refers to a lipoprotein that carries lipids away from peripheral cells into the circulation, and examples include HDL and subspecies thereof, or a mixture thereof. The term "lipid transporter" is also used in the art to refer to, for example, transmembrane proteins that transport cholesterol and phospholipids, for example, from inside a cell to outside the cell. Examples include ABCA1, SR-BI, SR-BII, ABCA4, ABCG5, ABCG8, or a mixture thereof.

The term "macula" as used herein refers to the light-sensing cells of the central region of the retina.

The term "macular degeneration" as used herein refers to deterioration of the central portion of the retina, the macula.

The term "reverse cholesterol transport" as used herein refers to transport of cholesterol from peripheral tissues to the liver. In a specific embodiment, it refers to efflux of lipid from RPE cells. In specific embodiments, it comprises efflux of cellular cholesterol and/or phospholipid to HDL, and, in further specific embodiments, it comprises HDL delivery of cholesterol ester to the liver, such as for biliary secretion.

The term "therapeutically effective" as used herein refers to the amount of a compound required to improve some symptom associated with a disease. For example, in the treatment of macular degeneration, a compound which improves sight to any degree or arrests any symptom of impaired sight would be therapeutically effective. A therapeutically effective amount of a compound is not required to cure a disease but will provide a treatment for a disease.

The term "upregulate" as used herein is defined as increasing the level and/or rate of an event, process, or mechanism, such as reverse cholesterol transport and/or the transcription and/or translation processes of a nucleic acid, such as a gene.

II. The Present Invention

The present inventors have shown that HDL is a preferred cholesterol and phospholipids acceptor for lipids effluxed by cultured human RPE. In aging BM, there is progressive accumulation of lipid and cross-linked protein that impedes hydraulic conductivity and macromolecular permeability. This abnormal deposition may also impair the ability of some larger molecular weight species of HDL to act as a lipoprotein acceptor. As HDL is unable to pass through BM and promote efflux and bind effluxed lipids, more lipids accumulate in both RPE and BM. Indeed, such accumulations are a major finding in age-related macular degeneration.

Apolipoprotein A1 (ApoA-I), having a mass of approximately 28 kDaltons, is the major lipoprotein component of HDL. When bound to phospholipids, it comprises nascent HDL particles that bind to ABCA1 on the RPE basal membrane and promote lipid efflux. Because of its low molecular weight, it can penetrate an aged BM more easily than larger molecular weight species of HDL to bind to the RPE. In addition to it role in promoting reverse cholesterol transport from RPE, ApoA-I also is a potent anti-oxidant. Anti-oxidants have been established to reduce visual loss in patients with AMD.

Several methods are used to increase ApoA-I delivery to RPE as a treatment for AMD, including administration intravenously as has been done in mouse models of atherosclerosis and in patients with coronary artery disease. ApoA-I, which is normally comprised of L-amino acids, can be administered as an ApoA-I mimetic peptide (e.g. amino acid sequence SEQ ID NO:15 and/or SEQ ID NO:16) comprising D-amino acids. The D-amino acid based ApoA-I mimentic peptide is not recognized as readily by human proteases, and thus can be administered orally. In some embodiments, this would be more convenient than parenteral administration with an intravenous formulation containing the L-amino acid ApoA-I or its mimetic peptide. Furthermore, oral synthetic phospholipid (1,2 Dimyristoyl-α-glycero-3-phosphocholine, DMPC) increases levels of circulating ApoA-I.

By way of example, patients with AMD (atrophic or exudative) are administered intravenously either ApoA-I, ApoA-I mimetic peptide, an agent to increase levels of circulating ApoA-I, such as DMPC, or a mixture thereof.

The histopathology of macula in patients with AMD shows diffuse thickening of Bruch's membrane, and the overlying RPE is attenuated and full of lipofuscin granules. Photoreceptors are shortened and atrophic, and much of the thickened Bruch's membrane consists of lipid deposition. It is known that following about 50 years of age, the rate of lipid accumulation accelerates (Holz et al., 1994).

Using cell culture methods to study lipid metabolism, the inventors have shown a number of analogous mechanisms for lipid metabolism that are shared by macrophages and human RPE cells. The shared biology of these two cell types indicates useful therapeutic approaches for treatment of AMD. Specifically, the present inventors are the first to show that RCT occurs in RPE cells, and enhancement of RCT is beneficial for removing undesired lipid from the RPE cells and/or Bruch's membrane to facilitate retinal metabolism. In a specific embodiment, the transporters in the RCT system are regulated to improve RCT. In a further specific embodiment, this regulatory aspect of the present invention provides a novel treatment for AMD.

Although there has been discussion in the field regarding mechanisms of lipid accumulation in macula of AMD individuals, the present invention regards efflux of lipid into the circulation, which reduces the amount of lipid in RPE and/or Bruch's membrane. Promotion of this efflux comprises one aspect of the invention and is an effective therapy for both early and late AMD. A skilled artisan recognizes that early AMD comprises the presence of drusen and late stage AMD comprises visual loss from choroidal neovascularization or geographic atrophy.

Thus, the present invention provides the novel idea in the field in which reverse cholesterol transport occurs in RPE cells. In specific embodiments, the invention provides methods and compositions related to facilitating efflux of cholesterol and/or phospholipids from inside an RPE cell to the outside of the RPE cell, and further through Bruch's membrane. In another specific embodiment, following efflux from Bruch's membrane the cholesterol and/or phospholipids are transported by apolipoprotein E, apolipoprotein A1, and other transporters, or a combination thereof, to HDL for removal to the liver.

A skilled artisan recognizes the important role reverse cholesterol transport (RCT) plays in lipid homeostasis. HDL levels are inversely correlated with incidence of coronary artery disease (CAD). Tangier's disease, which comprises a mutation of ABCA1, leads to deposition of cholesterol in reticuloendothelial tissues and premature atherosclerosis. Furthermore, the Apo E null mouse is an excellent model of atherosclerosis and hyperlipidemia. Interestingly, supporting an important role of Apo E in RCT, reconstitution of Apo E positive macrophages via bone marrow transplant into an Apo E null mouse prevents atherosclerosis. This occurs in spite of persistent hyperlipidemia.

In one embodiment of the present invention a transporter of lipid from RPE cells is enhanced for the transport activity, such as by an increase in the level of the transporter. Examples of transporters include apo E, ABCA1, SR-BI, SR-BII, ABCA4, ABCG5, ABCG8; other proteins that might be involved are LCAT, CETP, PLTP, LRP receptor, LDL receptor, Lox-1, and lipases. In a specific embodiment, lox-1 and PLTP are expressed in RPE, as demonstrated by RT_PCR. In a specific embodiment of the present invention, ApoA-I is utilized to facilitate RCT from RPE cells. In an additional specific embodiment, ApoA-I is made by RPE cells.

In a specific embodiment of the present invention, strategies for intervention for treatment of AMD are provided in which reverse cholesterol transport is enhanced at the level of the RPE by upregulating ApoA-I, ABCA1, Apo E, SR-BI and/or SR-BII expression. SR-B has been reported to be upregulated by 17 beta-Estradiol and testosterone. Additionally, or alone, HDL binding to effluxed lipids is enhanced, thereby increasing efflux of lipids from Bruch's membrane into the circulation and providing therapy for AMD. Although the present invention generally regards an increase in ApoA-I, a major lipoprotein component of HDL, in one embodiment, an increase in HDL levels overall is utilized to facilitate lipid efflux from RPE cells and/or Bruch's membrane, and in a specific embodiment, levels of specific subspecies of HDL are utilized to facilitate lipid efflux. For example, effluxed lipids could bind to preβ-HDL, HDL1, HDL2 or HDL3. Effluxed lipids could also bind prebeta-1, prebeta-2, prebeta- 3, and/or prebeta-4 HDL. In a specific embodiment, the effluxed lipids bind preferentially to HDL2 that comprises apo E.

One skilled in the art recognizes particular RCT components are present in RPE cells (Mullins et al., 2000; Anderson et al., 2001). Nuclear hormone receptors known to regulate expression of reverse cholesterol transport proteins are also expressed in cultured human RPE. Thus, in a preferred embodiment of the present invention, ligands to at least one of the nuclear hormone receptors upregulates RCT. In further embodiments, following efflux from RPE cells, the lipids bind HDL, so in an embodiment of the present invention there is upregulation of HDL for AMD treatment, such as by statins and/or niacin.

In an alternative embodiment, treatment for AMD comprises reduction of RCT. For example, in individuals past a certain age, such as about 50, 55, 60, 65, 70, 75, 80, and so on, the transporters are preferentially inhibited. In one aspect of this embodiment, HDL is unable to enter Bruch's membrane to remove the lipids and the RPE continues to efflux lipids. In such cases where effluxed lipids from RPE cannot be removed by a lipoprotein acceptor, lipid efflux by RPE is inhibited to maintain macromolecular transport across Bruch's membrane. Inhibition of RCT by reducing levels of ABCA-1, apo E, and/or SRB-1, or SRB-2 would reduce accumulation of lipid in Bruch's membrane.

In embodiments of the present invention, ligands for nuclear hormone receptors are utilized as compounds for enhancing RCT for the reduction of lipid content of RPE and Bruch's membrane. In a specific embodiment, the nuclear hormone receptor ligands are utilized for treatment of AMD. In a further specific embodiment, the nuclear hormone receptors comprise TR, RXR, and/or LXR. In other specific embodiments, ligands of the nuclear hormone receptors are delivered to at least one RPE cell to facilitate efflux of lipids from the RPE cell and/or are delivered to Bruch's membrane for efflux from Bruch's membrane. Examples of ligands for TR include T3 (3,5,3'-L-triiodothyronine). Other examples of TR ligands include but are not limited to TRIAC (3-triiodothyroacetic acid); KB141 (Karo Bio); GC-1; and 3,5 dimethyl-3-isopropylthyronine. Examples of ligands for RXR include 9 cis-retinoic acid, and other RXR ligands also include but are not limited to: AGN 191659 [(E)-5-[2-(5,6,7,8-tetrahydro-3,5,5,8,8-pentamethyl-2-naphthyl)propen-1-yl]-2-thiophen-ecarboxylic acid]; AGN 191701 [(E) 2-[2-(5,6,7,8-tetrahy-dro-3,5,5,8,8-pentamethyl-2-naphthyl)propen-1-yl]-4-thiophene-carboxylic acid]; AGN 192849 [(3,5,5,8,8,-pentamethyl-5,6,7,8-tetrahydronaphthalen-2-yl) (5 carboxypyrid-2-yl)sulfide]; LGD346; LG100268; LG100754; BMS649; and bexaroteneR (Ligand Pharmaceuticals) (4-[1-(5,6,7,8-tetrahydro-3,5,5,8,8-pentamethyl-2-naphthalenyl) ethenyl] benzoic acid). Examples of ligands for LXR include 22 (R) hydroxycholesterol, acetyl-podocarpic dimer, T0901317, and GW3965.

In an embodiment of the present invention, expression of a sequence is monitored following administration of an upregulator of its expression or a compound suspected to be an upregulator. A skilled artisan recognizes how to obtain these sequences, such as commercially from Celera Genomics, Inc. (Rockville, Md.) or from the National Center for Biotechnology Information's GenBank database. Exemplary apo E polynucleotide sequences include the following, cited with their GenBank Accession number: SEQ ID NO:1 (K00396; incorporated by reference); SEQ ID NO:2 (M10065; incorporated by reference); and SEQ ID NO:3 (M12529; incorporated by reference). Some exemplary apo E polypeptide sequences include the following, cited with their GenBank Accession number: SEQ ID NO:4 (AAB59546; incorporated by reference); SEQ ID NO:5 (AAB59397; incorporated by reference); and SEQ ID NO:6 (AAB59518; incorporated by reference).

In other embodiments, sequences of ABCA-1 are utilized, such as to monitor ABCA-1 expression related to methods of the present invention. Some examples of ABCA1 polynucleotides include SEQ ID NO:7 (NM_005502; incorporated by reference); and SEQ ID NO:8 (AB055982; incorporated by reference). Some examples of ABCA1 polypeptides include SEQ ID NO:9 (NP_005493; incorporated by reference); and SEQ ID NO:10 (BAB63210; incorporated by reference).

In some methods of the present invention, expression levels of sequences of SR-BI and SR-B2 polynucleotides are monitored following administration of a nuclear hormone receptor ligand. An example of SR-BI polynucleotide is SEQ ID NO:11 (NM_005505; incorporated by reference) and an example of a SR-BI polypeptide is SEQ ID NO:12 (NP_005496; incorporated by reference).

III. Pharmaceutical Compositions and Routes of Administration

Compositions of the present invention may have an effective amount of a compound for therapeutic administration and, in some embodiments, in combination with an effective amount of a second compound that is also an anti-AMD agent. In a specific embodiment, the compound is a ligand/agonist of a nuclear hormone receptor. In other embodiments, compounds that upregulate expression of HDL are the compounds for therapeutic administration. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-AMD agents, can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants and the like.

The delivery vehicles of the present invention may include classic pharmaceutical preparations. Administration of these compositions according to the present invention will be via any common route so long as the target ocular tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions. In some embodiments, the compositions are administered by sustained release intra- or extra-ocular devices.

The vehicles and therapeutic compounds therein of the present invention are advantageously administered in the form of injectable compositions either as liquid solutions or suspensions; solid forms suitable for solution in, or suspension in, liquid prior to injection also may be prepared. These preparations also may be emulsified. A typical composition for such purposes comprises a 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters, such as theyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

All of the essential materials and reagents required for AMD treatment, diagnosis and/or prevention may be assembled together in a kit. When the components of the kit are provided in one or more liquid solutions, the liquid solution preferably is an aqueous solution, with a sterile aqueous solution being particularly preferred.

For in vivo use, an anti-AMD agent may be formulated into a single or separate pharmaceutically acceptable syringeable composition. In this case, the container means may itself be an inhalant, syringe, pipette, eye dropper, or other such like apparatus, from which the formulation may be applied to an infected area of the body, such as the lungs, injected into an animal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the anti-AMD composition.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle.

The active compounds of the present invention will often be formulated for parenteral administration, e.g., formulated for injection via the intravenous, intramuscular, subcutaneous, or even intraperitoneal routes. The preparation of an aqueous composition that contains a second agent(s) as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in eye drops, cremes and lotions.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intraocular, intravenous, intramuscular, and subcutaneous administration. In this connection, sterile aqueous media that can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Targeting of ocular tissues may be accomplished in any one of a variety of ways. In one embodiment, there is the use of liposomes to target a compound of the present invention to the eye, and preferably to RPE cells and/or Bruch's membrane. For example, the compound may be complexed with liposomes in the manner described above, and this compound/liposome complex injected into patients with AMD, using intravenous injection to direct the compound to the desired ocular tissue or cell. Directly injecting the liposome complex into the proximity of the RPE or Bruch's membrane can also provide for targeting of the complex with some forms of AMD. In a specific embodiment, the compound is administered via intra-ocular sustained delivery (such as Vitrasert® or Envision® by Bauch and). In a specific embodiment, the compound is delivered by posterior subtenons injection. In another specific embodiment, microemulsion particles with apo E (such as, recombinant) are delivered to ocular tissue to take up lipid from Bruch's membrane, RPE cells, or both.

Those of skill in the art will recognize that the best treatment regimens for using compounds of the present invention to treat AMD can be straightforwardly determined. This is not a question of experimentation, but rather one of optimization, which is routinely conducted in the medical arts. In vivo studies in nude mice often provide a starting point from which to begin to optimize the dosage and delivery regimes. The frequency of injection will initially be once a week, as has been done in some mice studies. However, this frequency might be optimally adjusted from one day to every two weeks to monthly, depending upon the results obtained from the initial clinical trials and the needs of a particular patient. Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 mg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 mg/Kg body weight. In other embodiments, it is envisaged that higher does may be used, such doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

In some embodiments of the present invention, the ApoA-I composition is comprised as a polynucleotide, utilizing delivery vehicles well known in the art. In other embodiments of the present invention, ApoA-I composition comprises a polypeptide or peptide. Any form may be distributed in a delivery composition, such as a liposome, examples of which are known in the art.

IV. Kits

Any of the compositions described herein may be comprised in a kit. In a non-limiting example, an ApoA-I composition, and in some embodiments, at least one additional agent, may be comprised in a kit. In other embodiments, a lipid transporter such as HDL or a subspecies thereof.

The kits may comprise a suitably aliquoted ApoA-I composition, and/or additional agent compositions of the present invention, whether labeled or unlabeled, as may be used to prepare a standard curve for treatment of macular degeneration, such as AMD. The components of the kits may be packaged in aqueous media or in lyophilized form. When reagents and/or components are provided as a dry powder, the powder can be reconstituted by the addition of a suitable solvent. It is envisioned that the solvent may also be provided in another container means.

Suitable ApoA-I compositions comprise those that are sufficient to upregulate reverse cholesterol transport, those that reduce lipid accumulations in BM or RPE, those that increase efflux of lipids from BM, and/or are sufficient to provide an anti-oxidant therapeutic effect. In preferred embodiments, the ApoA-I compositions are suitable to provide therapy for macular degeneration, such as by ameliorating and/or preventing at least one symptom.

The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the nuclear hormone receptor ligand, additional agent, and any other reagent containers in close confinement for commercial sale. Such containers may include injection or blow-molded plastic containers into which the desired vials are retained.

V. Biological Functional Equivalents

As modifications and/or changes may be made in the structure of ApoA-I polypeptides or peptides according to the present invention, while obtaining molecules having similar or improved characteristics, such biologically functional equivalents are also encompassed within the present invention.

A. Modified Polynucleotides and Polypeptides

Although administration of ApoA-I peptides or polypeptides is preferable, in some embodiments the ApoA-I composition is a polynucleotide encoding the desired polypeptide or peptide. The biological functional equivalent may comprise a polynucleotide that has been engineered to contain distinct sequences while at the same time retaining the capacity to encode the "wild-type" or standard protein or other polypeptide or peptide of interest. This can be accomplished to the degeneracy of the genetic code, i.e., the presence of multiple codons, which encode for the same amino acids. In one example, one of skill in the art may wish to introduce a restriction enzyme recognition sequence into a polynucleotide while not disturbing the ability of that polynucleotide to encode a protein.

In another example, a polynucleotide may encode a biological functional equivalent with more significant changes. Certain amino acids may be substituted for other amino acids in a protein structure without appreciable loss of interactive binding capacity with structures such as, for example, antigen-binding regions of antibodies, binding sites on substrate molecules, receptors, and such like. So-called "conservative" changes do not disrupt the biological activity of the protein, as the structural change is not one that impinges of the protein's ability to carry out its designed function. It is thus contemplated by the inventors that various changes may be made in the sequence of genes and proteins disclosed herein, while still fulfilling the goals of the present invention.

In terms of functional equivalents, it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Biologically functional equivalents are thus defined herein as those proteins (and polynucleotides) in selected amino acids (or codons) may be substituted. Functional activity, such as the ability to bind lipids, is preferably retained in any natural or synthetic ApoA-I polypeptide or peptide.

In general, the shorter the length of the molecule, the fewer changes that can be made within the molecule while retaining function. Longer domains may have an intermediate number of changes. The full-length protein will have the most tolerance for a larger number of changes. However, it must be appreciated that certain molecules or domains that are highly dependent upon their structure may tolerate little or no modification.

Amino acid substitutions are generally based on the relative similarity of the amino acid side-chain substituents, for example, their hydrophobicity, hydrophilicity, charge, size, and/or the like. An analysis of the size, shape and/or type of the amino acid side-chain substituents reveals that arginine, lysine and/or histidine are all positively charged residues; that alanine, glycine and/or serine are all a similar size; and/or that phenylalanine, tryptophan and/or tyrosine all have a generally similar shape. Therefore, based upon these considerations, arginine, lysine and/or histidine; alanine, glycine and/or serine; and/or phenylalanine, tryptophan and/or tyrosine; are defined herein as biologically functional equivalents.

To effect more quantitative changes, the hydropathic index of amino acids may be considered. Each amino acid has been assigned a hydropathic index on the basis of their hydrophobicity and/or charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and/or arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index and/or score and/or still retain a similar biological activity. In making changes based upon the hydropathic index, the substitution of amino acids whose hydropathic indices are within +2 is preferred, those which are within +1 are particularly preferred, and/or those within +0.5 are even more particularly preferred.

It also is understood in the art that the substitution of like amino acids can be made effectively on the basis of hydrophilicity, particularly where the biological functional equivalent protein and/or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and/or antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and/or those within ±0.5 are even more particularly preferred.

B. Altered Amino Acids

The present invention, in some aspects, may rely on the synthesis of peptides and polypeptides in cyto, via transcription and translation of appropriate polynucleotides. In alternative embodiments, the polypeptide or peptide is synthesized outside a cell, such as chemically. These peptides and polypeptides may include the twenty "natural" amino acids, and, in some embodiments, post-translational modifications thereof. However, in vitro peptide synthesis permits the use of modified and/or unusual amino acids. A table of exemplary, but not limiting, modified and/or unusual amino acids is provided herein below.

TABLE 1

Modified and/or Unusual Amino Acids

| Abbr. | Amino Acid | Abbr. | Amino Acid |
|---|---|---|---|
| Aad | 2-Aminoadipic acid | EtAsn | N-Ethylasparagine |
| BAad | 3-Aminoadipic acid | Hyl | Hydroxylysine |
| BAla | beta-alanine, beta-Amino-propionic acid | AHyl | allo-Hydroxylysine |

TABLE 1-continued

Modified and/or Unusual Amino Acids

| Abbr. | Amino Acid | Abbr. | Amino Acid |
|---|---|---|---|
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | allo-Isoleucine |
| Aib | 2-Aminoisobutyric acid | MeGly | N-Methylglycine, sarcosine |
| BAib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

C. Mimetics

In addition to the biological functional equivalents discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents. In a specific embodiment, the key portion comprises lipid binding activity.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

Other approaches have focused on the use of small, multi-disulfide-containing proteins as attractive structural templates for producing biologically active conformations that mimic the binding sites of large proteins. Vita et al. (1998). A structural motif that appears to be evolutionarily conserved in certain toxins is small (30-40 amino acids), stable, and high permissive for mutation. This motif is composed of a beta sheet and an alpha helix bridged in the interior core by three disulfides.

Beta II turns have been mimicked successfully using cyclic L-pentapeptides and those with D-amino acids. Weisshoff et al. (1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

EXAMPLES

The following is an illustration of preferred embodiments for practicing the present invention. However, they are not limiting examples. Other examples and methods are possible in practicing the present invention.

Example 1

Materials and Methods

Cell Culture and Drug Treatments

Primary cultures of normal human RPE cells from passages 5 to 10 were used for the experiments described. RPE cells were grown to confluence on laminin-coated 6 well Transwell tissue culture plates (Costar) with DMEM-H21 containing 10% fetal bovine serum, 2 mM glutamine, 50 μg/ml gentamicin and 2.5 mg/ml fungizone in the top and bottom chambers. For immunofluorescent staining cells were grown on laminin coated slides in the same medium. Cells were grown for at least 1 week at confluence prior to drug treatment. Cells to be treated with drugs were incubated in serum free DMEM-H21 prior to drug addition. Drug treatments were in serum free DMEM-H21 with or without $10^{-7}$ M thyroid hormone ($T_3$), $2.5 \times 10^{-6}$ M 22 (R) hydroxycholesterol, or $10^{-7}$ M cis retinoic acid in both chambers for 36 hours.

RT-PCR

Confluent cell cultures were harvested and total RNA was purified using RNAzol (Teltest, Inc., Friendswood, Tex.) according to the manufacturer's instructions. Equal amounts of purified RNA were used in each reaction as templates for cDNA synthesis using the 1st Strand Synthesis Kit for RT-PCR (AMV) (Boehringer, Indianapolis, Ind.). RT-PCR was carried out on 1 μg of cDNA with Amplitaq Taq polymerase (Perkin-Elmer, Branchburg, N.J.). In some experiments apo E RT-PCR products were quantified using the QuantumRNA assay kit according to the manufacturer's instructions (Ambion, Austin, Tex.). Briefly, 18S rRNA and apo E cDNAs are simultaneously amplified in each reaction. The RT-PCR products are resolved by electrophoresis on 1.4% agarose gels. The apo E mRNA expression is assessed relative to the internal 18S rRNA expression by densitometric analysis of photographed agarose gels.

RT-PCR primers specific to human apo E, ABCA1, SR-BI, SR-BII, and lxr α were used. The RT-PCR product of the predicted sizes for the apo E, ABCA1, SR-BI, and SR-BII RT-PCR products were excised form the gel and their identities were confirmed by DNA sequencing (not shown).

Immunofluoresence Microscopy

RPE cells, grown on slides, were σταινεδ with either antisera to ABCA1, or with purified antibodies to SR-BI or SR-BII. Cells were fixed in ice cold 100% MeOH for 20 min. All subsequent steps were performed at room temperature.

Cells were washed in phosphate buffered saline (PBS) and incubated for in 5% goat serum in PBS for 30 min. Cells were then washed in buffer A (150 mM NaCl, 10 mM phosphate, pH 7.8) and incubated with the primary antibody in buffer A for 45 min. After washing with buffer A the cells were incubated in Avidin Blocking Reagent (Vector Laboratories, Burlingame, Calif.) for 15 min, washed in buffer A again and incubated in Biotin Blocking Reagent (Vector Laboratories, Burlingame, Calif.) for 15 min. After washing in buffer A, cells were incubated in 10 µg/ml biotinylated goat anti-rabbit IgG (Vector Laboratories, Burlingame, Calif.) in buffer A for 30 min, washed in buffer A and incubated in 20 µg/ml fluorescein conjugated avidin D (Vector Laboratories, Burlingame, Calif.) in buffer B (150 mM NaCl, 100 mM sodium bicarbonate, pH 8.5) for 30 min. The cells were washed in buffer B and a cover slip was added to each slide, over a few drops of Vectashield (Vector Laboratories, Burlingame, Calif.). The slides were stored in the dark until ready for microscopic examination.

Apo E Western blotting

Cells were treated with Media was concentrated 20-fold by centrifugal ultrafiltration (VIVA SPIN 20, MCO 5,000, Viva Sciences, Hannover, Germany), dialyzed against 0.15M NaCl, 1 mM sodium EDTA, 0.025% sodium azide (SalEN). Total protein content was determined by a modified Lowry assay (Bio-Rad DC kit, Richmond, Calif.). Concentrated media (50 µg protein) was made to Start Buffer (0.025 M NaCl, 0.010 M tris (pH 8.5), 5 mM $MnCl_2$) and adsorbed onto a 0.1 ml column containing Heparin-Sepharose CL-4B (Pharmacia, Uppsala, Sweden). Following a 2 ml wash in Start Buffer, the apo E containing bound fraction was eluted with 0.5M NaCl in Start buffer. The eluate was concentrated to 20 µl and buffer-exchanged to SalEN by centrifugal ultrafiltration (Biomax, 5k MCO, Millipore, Bedford, Mass.). Apo E was resolved by tris-tricine buffered SDS-PAGE (5-25% linear acrylamide gradient) and proteins electrophoetically transferred (55V, 18 h) to nitrocelluose membrane filters (Schleicher and Shuell, Keen, N.H.). Membranes were blocked with 10% bovine serum albumin at room temperature and probed with 1% goat anti-human apo E antiserum (18 h, 3° C.) prepared in 0.15% NaCl, 1 mM EDTA (pH 7.4), 0.1% Triton X-100 (SalET). The primary-bound anti-apo E antibodies were detected colorimetrically with horseradish peroxidase conjugated rabbit anti-goat Ig (H+L) and $NiCl_2$-enhanced diaminobenzine staining. Stained bands were compared densitometrically from the digitized scanned image (NIH Image, v.1.62). Anti apo E antibodies were obtained by hyper-immunization of goats with purified apo E or obtained from Assay Designs (A299, Ann Arbor, Mich.).

Lipoprotein fractions were prepared from conditioned media that was adjusted with solid KBr to a density of 1.21 g/ml. Samples were ultracentrifuged in a Beckman 42.2 Ti rotor at 40,000 rpm for 18 h at 10 C. The lipoprotein and lipoprotein-free fractions, the top and bottom 50 µl, respectively, were dialysed against SalEN prior to analysis.

[$^{14}$C] Docosohexanoic Acid (DHA) Labeled POS Uptake and Transport

Bovine outer photoreceptor outer segments (POS) were labeled by incubating for with Coenzyme A, ATP, $Mg^{2+}$, and [$^{14}$C]-DHA. Cells grown on laminin coated Transwell plates were incubated with 12 µg/ml labeled POS in the apical chamber for 36 hours in medium containing 10% lipoprotein deficient fetal bovine serum. The basal medium was subjected to scintillation counting to determine the amount of [$^{14}$C] labeled lipids transported through the RPE cells.

Identification of Acceptors for Exported $^{14}$C Lipids

Bovine outer photoreceptor outer segments (POS) were labeled by incubating for with Coenzyme A, ATP, $Mg^{2+}$, and [$^{14}$C]-DHA. Cells grown on laminin coated Transwell plates were incubated with 12 µg/ml labeled POS in the apical chamber for 36 hours in medium containing 10% lipoprotein deficient fetal bovine serum. The basal chambers contained either 1 mg/ml human HDL, 1 mg/ml human LDL or 100% human plasma. The basal medium was collected and lipoproteins were repurified from by potassium bromide density gradient centrifugation at d=1.21 g/ml (Beckman 42.2 Ti rotor, 40,000 rpm, 18 h, 10° C.), dialyzed, and resolved by size in nondenaturing 0-35% PAGE. Gels were stained with coomassie blue R-250. Gel lanes were sectioned into thirty 2 mm slices that were digested (TS-1, Research Products International) and radioactivity quanitfied by liquid scintillation spectrometry.

Example 2

Expression of Transporters in RPE Cells

One skilled in the art recognizes that certain RCT components in cultured human RPE cells have been demonstrated (Mullins et al, 2000; Anderson et al., 2001). Nuclear hormone receptors known to regulate expression of reverse cholesterol transport proteins are also expressed in cultured human RPE.

A skilled artisan recognizes that there is expression of TRs and RXRs in RPE cells in culture (Duncan et al, 1999). RT-PCR of human RPE cell cDNA revealed that these cells also express mRNAs for apo E, ABCA1, SR-BI, SR-BII and lxr α. As shown in FIG. 1 lane 1, FIG. 1 lane 2 and FIG. 1 lane 3, RPE cells express mRNAs for apo E, ABCA1 and lxr α, respectively.

Figure 2:
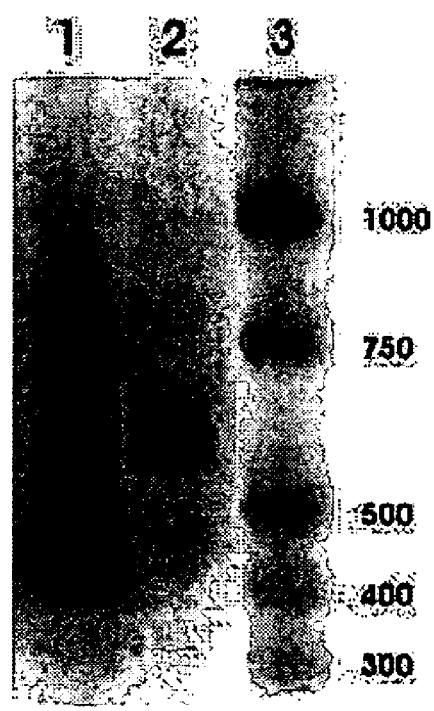
FIG. 2 shows RPE cell expression of SR-BI and SR-BII.

As shown in FIG. 2, lane 1, and FIG. 2, lane 2, RPE cells express mRNA for SR-BI and SR-BII respectively.

Figure 3:
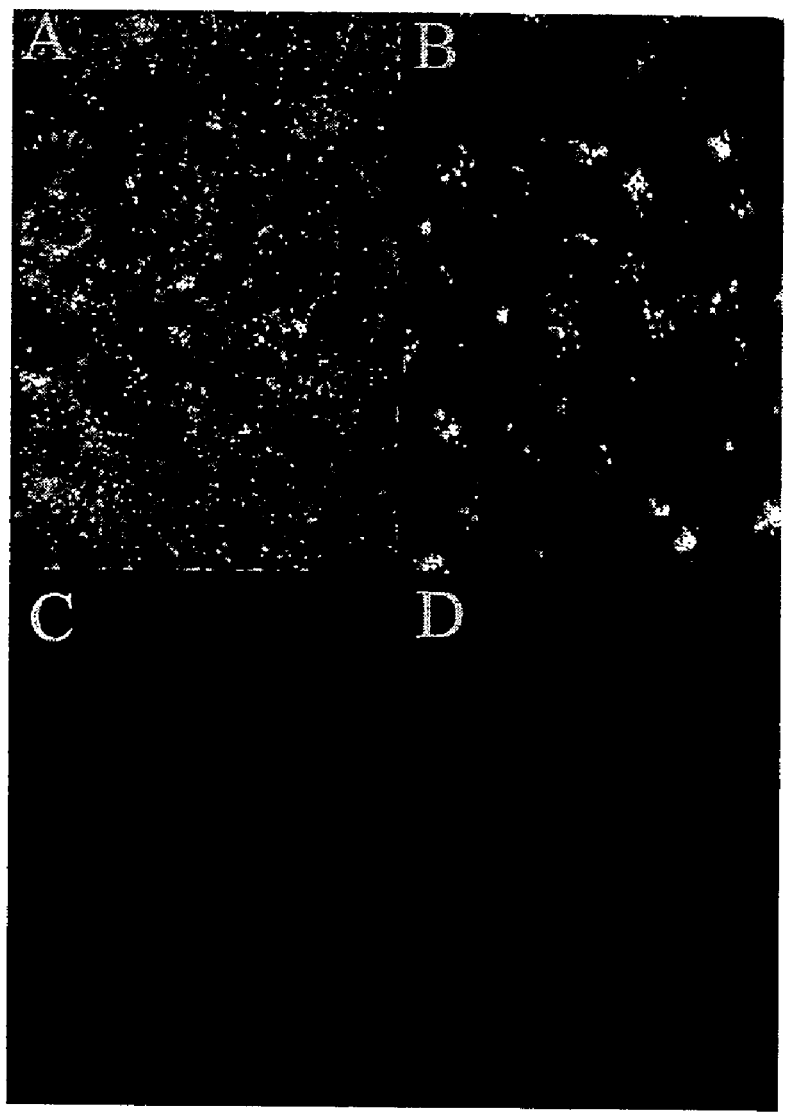
FIG. 3 illustrates SR-BI and SR-BII immunofluorescence in RPE cells.

Furthermore, in immunofluoresence microscopy experiments, RPE cells stain strongly for SR-BI (FIG. 3A) and SR-BII (FIG. 3B). Control non-specific IgG or antibody vehicle did not stain RPE cells (FIGS. 3C and 3D, respectively). Expression of SR-BI and SR-BII in these cells was confirmed by PCR.

Figure 4:
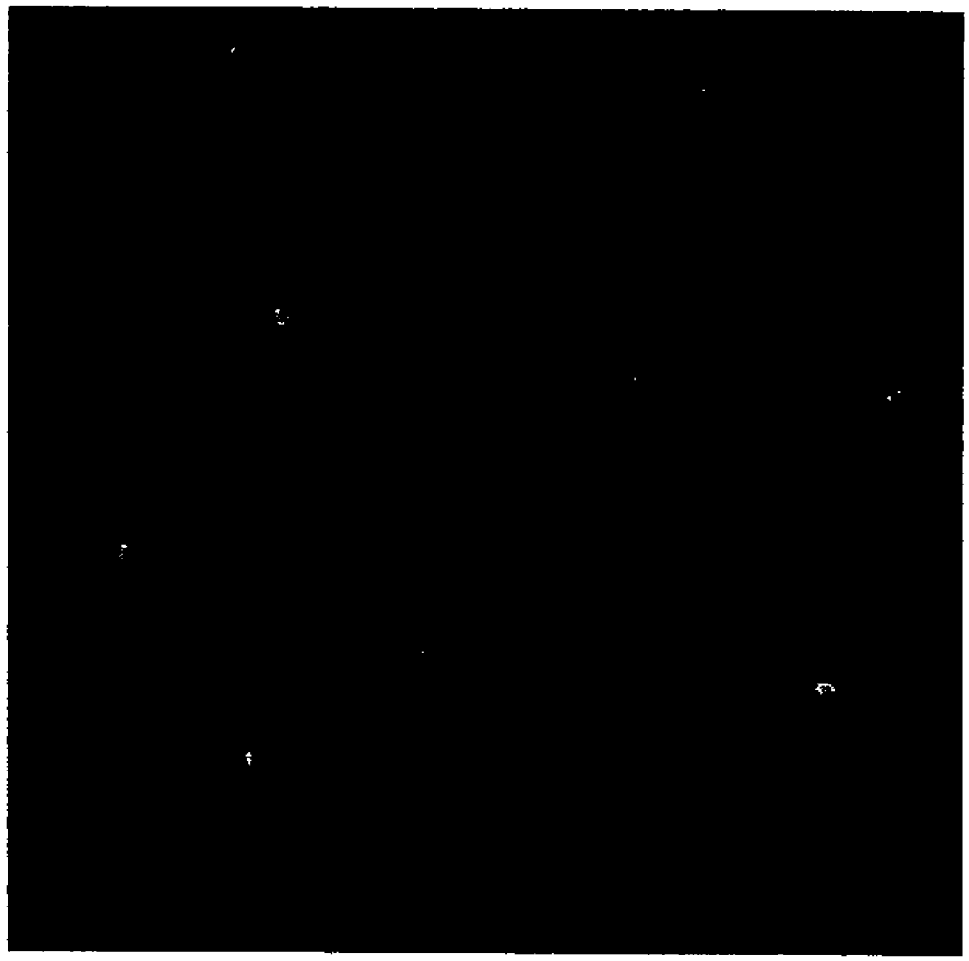
FIG. 4 demonstrates ABCA1 immunofluorescence in RPE cells.

Expression of ABCA1 protein was demonstrated by immunofluorescent staining of RPE cells with an antibody to ABCA1 (FIG. 4). Cell nuclei were stained with DAPI.

Example 3

Regulation of APO E Secretion in RPE Cells

Figure 5:
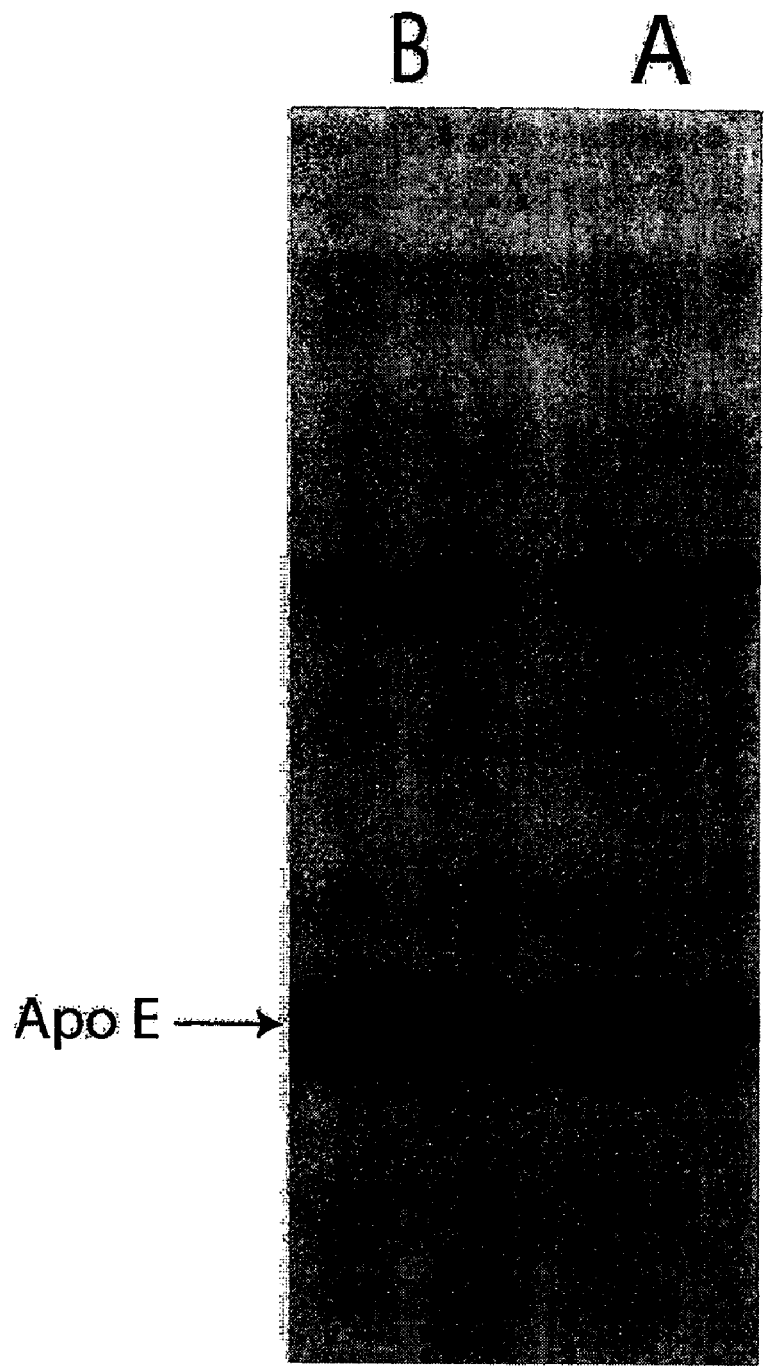
FIG. 5 demonstrates that basal Apo E expression is greater than apical Apo E expression in cultured human RPE cells.

In order to distinguish apical (A) from basally (B) secreted apo E, RPE cells were cultured on laminin-coated Transwell plates. Specifically, human cultured RPE (passage 2-10, 35 y.o. donor) were placed on laminin-coated Transwell plates, wherein the upper and lower wells both had serum-free media. Total protein and apo E-specific protein concentrations were measured from media pooled and concentrated from 3-6 replicate wells. To assess apo E-specific secretion, apo E was purified from conditioned media by heparin-sepharose affinity chromatography and visualized by western blotting. Apo E concentrations were consistently greater in the basolateral media (FIG. 5, lane 1 vs. lane 2). These data demonstrate that RPE cells display polarized secretion of cellular proteins, including apo E. Thus, this indicated that Apo E is preferentially secreted basally, supporting its role in RCT.

Figure 6:
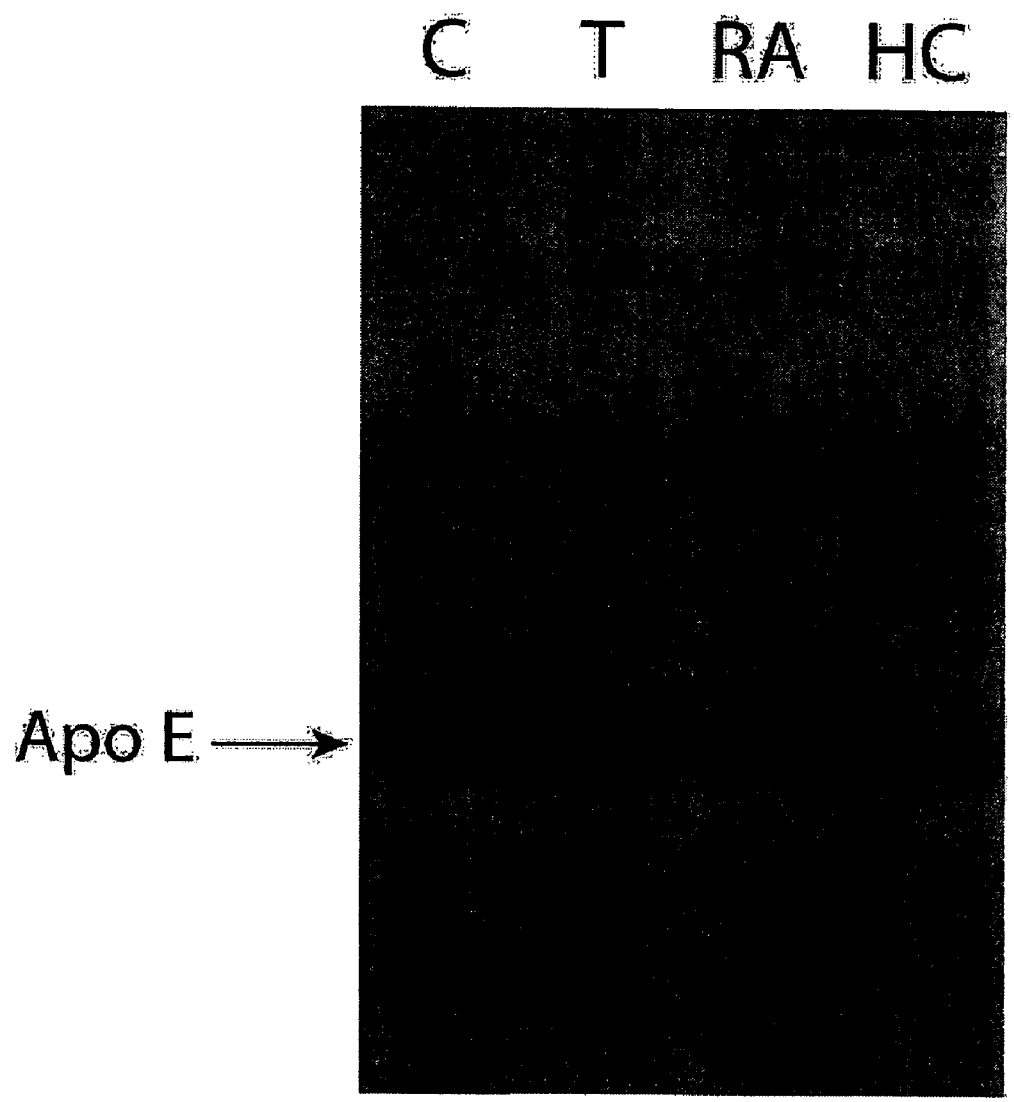
FIG. 6 shows regulation of Apo E expression by nuclear hormone receptor ligands.

Since RPE cells express lxr α as well as thyroid hormone receptors (TRs) and retinoid-X-receptors (RXRs), the effect of $10^{-7}$ M T3, $2.5 \times 10^{-6}$ M 22 (R) hydroxycholesterol (HC) (an lxr α agonist), or $10^{-7}$ M cis retinoic acid (cRA) (an RXR agonist) on apo E secretion from RPE cells was tested. FIG. 6 illustrates the same experimental procedure as described above, but with basal and apical media both containing the following compounds for a 36 hour incubation: T3 ($10^{-7}$) M (T); 9 cis-RA ($10^{-6}$) M (RA); and 22 (R) hydroxycholesterol 2.5 ($10^{-6}$) M (HC). The basal media was analyzed for Apo E expression with Western blot, and the results showed increased basal expression of Apo E with the compound treatments. Thus, as before, polarized apo E secretion was observed and, in this case, occurred in the presence of T3, HC or cRA, indicating that an increase in levels of basally secreted apo E is the result of administration of these compounds to RPE cells.

Example 4

Assay of Efflux from RPE Cells

This example characterizes efflux of POS residues from RPE cells, particularly regarding binding to HDL. Giusto et al. (1986) describes a method of $^{14}$C decosahexanoic acid (DHA) labeling of bovine photoreceptor outer segment (POS) lipids. Generally, an approximately 36 hour incubation over human RPE cells wherein the basal medium contains plasma, HDL, or LDL is followed by centrifugation of the basal media to collect lipoprotein fraction, which is then analyzed to determine distribution of radioactivity.

Figure 7:
FIG. 7 provides a non-denatured polyacrylamide gel of lipoprotein fractions.
Figure 7:
Figure 7:

Specifically, bovine photoreceptor outer segment (POS) are labeled with $^{14}$C decosahexanoic acid (DHA) and placed in lipoprotein deficient media. Following this, they are placed over cultured human RPE on Transwell plates for 36 hours, and the basal medium contained either 100% plasma, HDL (1 mg/cc) or LDL (1 mg/cc). After 36 hours, basal media was centrifuged to collect lipoprotein fraction (density 1.2). This fraction was then run on a non-denaturing gel and stained with Coomassie blue. FIG. 7 shows LDL and HDL fractions, both separately and together in plasma (PL). The PL fraction contains the same amount of HDL and LDL as each of the separated fractions (HDL, LDL).

Figure 8:
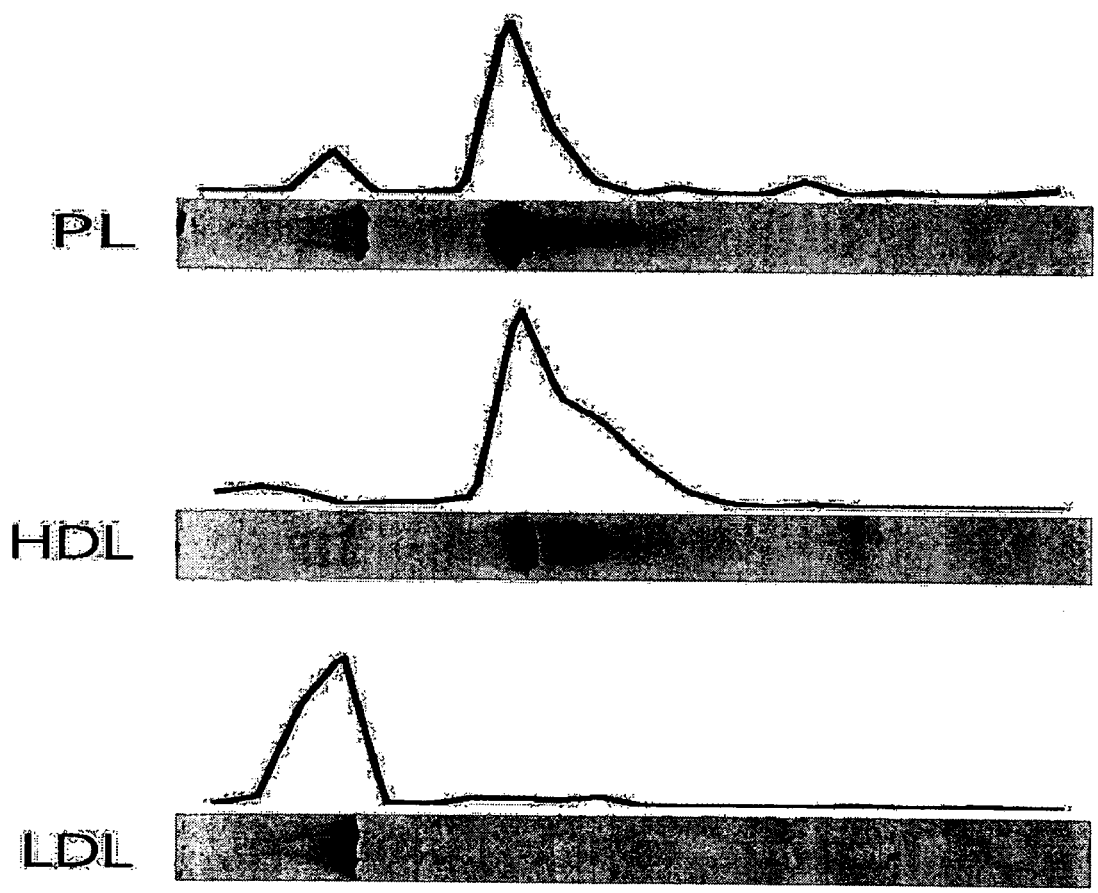
FIG. 8 shows $^{14}C$ distribution of the fractions from FIG. 7.

The PA gel was cut into about 1 mm pieces, and the radioactivity distribution was determined (FIG. 8). With either LDL or HDL alone, counts were observed over respective lipoprotein fractions. When both LDL and HDL in plasma are present, counts localize preferentially over HDL fraction. This indicates that following phagocytosis of POS by RPE, POS residues are effluxed and preferentially bound by HDL. This is a novel demonstration illustrating that RCT to an HDL acceptor occurs in RPE cells.

Figure 9:
FIG. 9 demonstrates thin layer chromatography illustrating the identification of six out of seventeen spots of an HDL fraction. Note: HDL is the high density lipoprotein fraction; POS is labeled POS starting material; PC is phophatidylcholine; PI is phosphatidylinisotol; PE is phosphatidylethanolamine; C is cholesterol; TRL is TG rich lipid, including triglycerides and cholesterol ester.

To characterize the lipids in the lipoprotein fraction, thin layer chromatography was performed. Acid charring was used to identify lipid containing spots. The spots were scraped off of the plate and $^{14}$C was quantified by liquid scintillation counting. Six of 17 $^{14}$C-containing spots were identified with standards shown (FIG. 9). Eleven $^{14}$C-containing spots bound to HDL remain unidentified and could be unique serum marker(s) for patients with early AMD.

Thus, in an embodiment of the present invention, a patient sample is obtained, such as by drawing blood, and the HDL is examined for bound POS residues. From this, a determination of their risk of visual loss from AMD is made. In a specific embodiment, the profile of bound POS residues is indicative of identifying an individual afflicted with ocular disease and/or of identifying an individual at risk for developing an ocular disease.

Example 5

Modulation of RCT by Compound Administration

Figure 10:
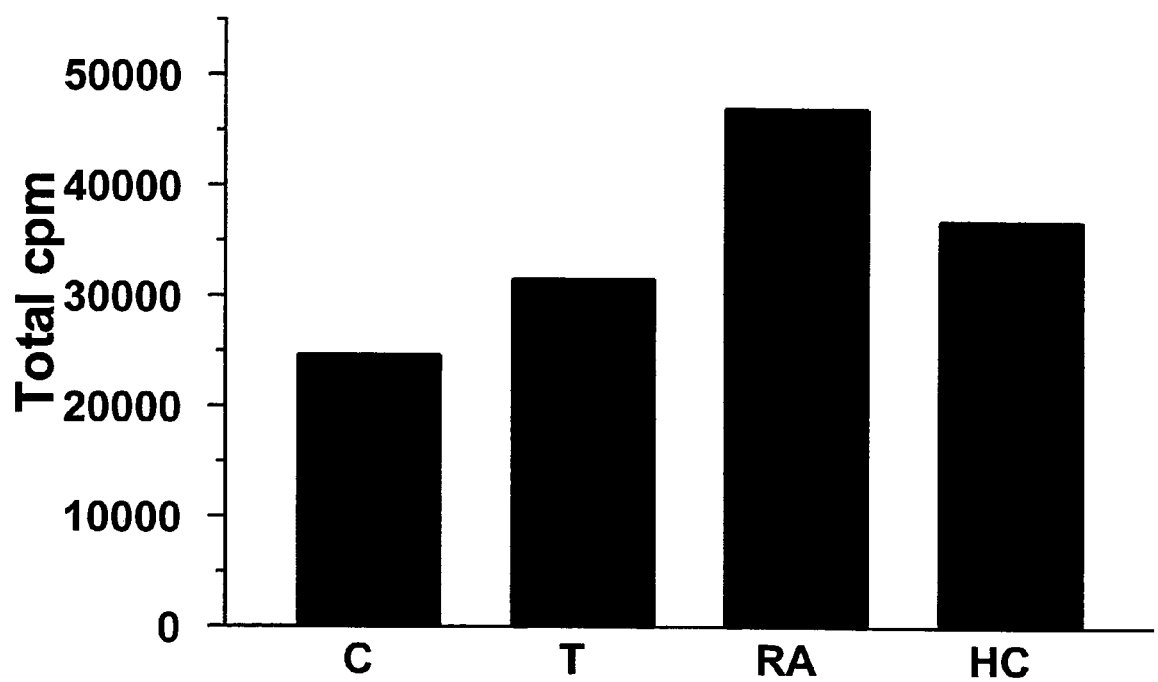
FIG. 10 demonstrates that $^{14}C$ counts increase following drug treatments that increase RCT.

This experiment determines whether compound administration can upregulate efflux of labeled POS residues to HDL, particularly by showing regulation of $^{14}$C-DHA labeled POS efflux into basal media. An assay similar to that described in Example 4 is utilized; however, in this Example the cells were treated with T3, 9 cis-retinoic acid, and 22 (R) hydroxycholesterol in the concentrations described above for 36 hours. Total radioactivity (cpm) in the absence of HDL purification was determined by liquid scintillation counting of the basal media. FIG. 10 indicates that compound treatments increase RCT by cultured human RPE cells.

Specifically, cells were grown for 1 to 2 weeks at confluence on Transwell plates. $^{14}$C-labeled POS (30 mg/ml) were added to the apical medium. The apical and basal medium comprised either $10^{-7}$ M T3, $2.5 \times 10^{-5}$ M 22 (R) hydroxycholesterol, or $10^{-7}$ M cis retinoic acid. The basal medium contained 1 mg/ml HDL. After 36 hours the basal medium was collected and $^{14}$C counts were determined by scintillation counting. As stated, all of the compound treatments increased transport of $^{14}$C-labeled POS to the basal medium.

The effect of T3 on Apo E mRNA levels was also assessed by RT-PCR. Treatment with $10^{-7}$ M T3 resulted in a 1.5 to 2-fold increase in apo E mRNA levels, suggesting that T3 is acting, at least in part, to increase apo E levels at the mRNA level. In specific embodiments, administration of 9 cis-retinoic acid and 22 (R) hydroxycholesterol similarly upregulates expression of apo E.

Figure 11:
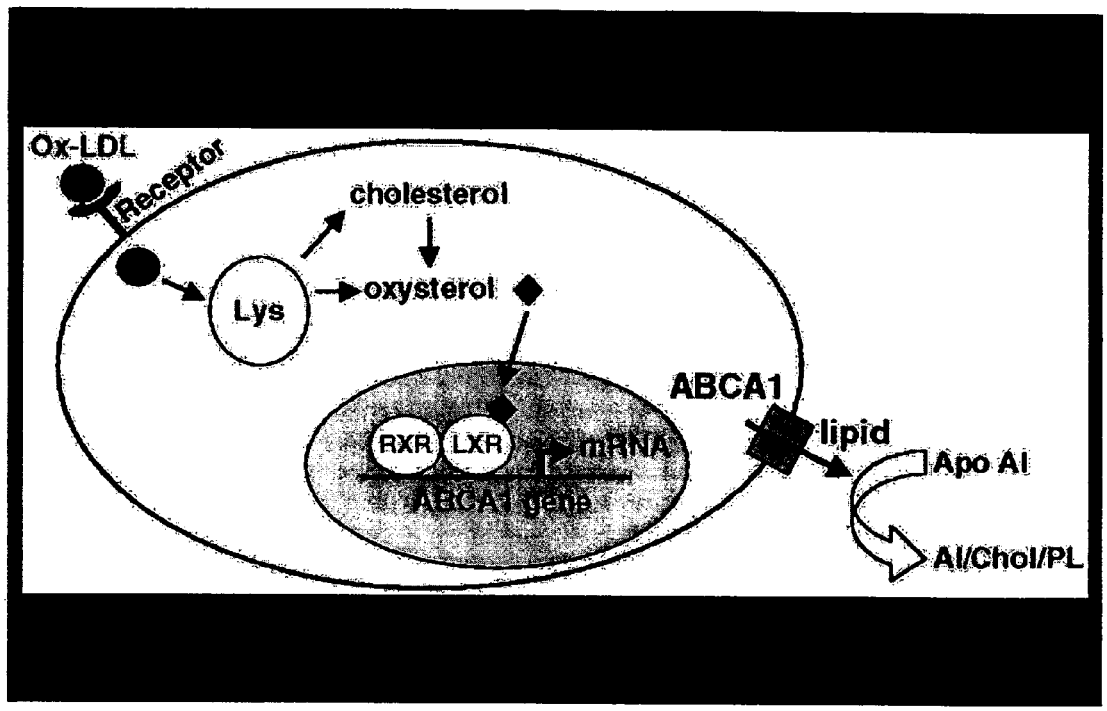
FIG. 11 illustrates ABCA1 regulation by RXR and LXR ligands.

Thus, in a specific embodiment, RCT is regulated via nuclear hormone receptor ligands. For example, ABCA1 expression is upregulated by binding of LXR and RXR agonists to their respective nuclear hormone receptors (FIG. 11). Since these receptors form heterodimers bound to the ABCA1 promoter, ligand binding increases expression of ABCA1 and, hence, RCT.

Example 6

Identification of HDL as Lipid Acceptor from RPE Cells

Figure 12:
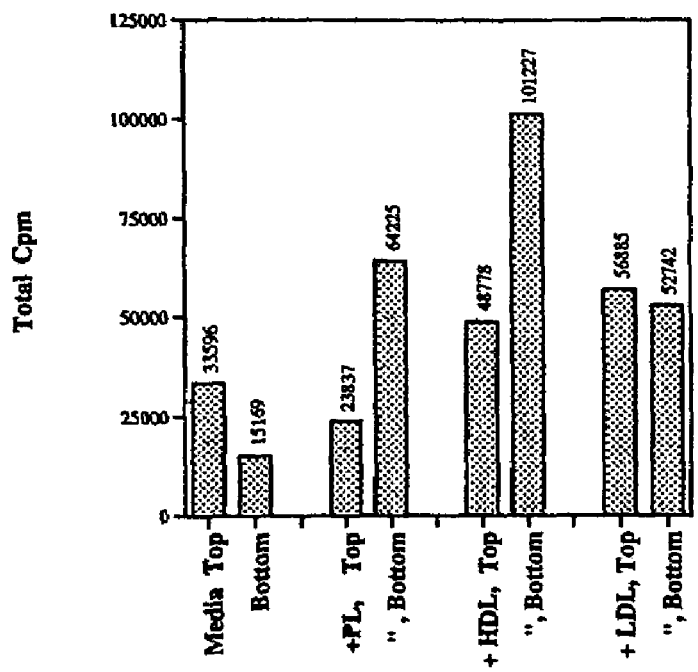
FIG. 12 shows HDL, LDL and plasma stimulation of $^{14}C$-labeled lipid transport the identification of HDL from RPE cells.

In the presence of added purified human LDL and HDL, radiolabeled lipid efflux is enhanced (FIG. 12). As shown graphically, efflux (bottoms in graph) was greatly enhanced by the presence of plasma (PL in graph), HDL or LDL, as compared to no addition to the bottom medium (left side of graph).

As shown in FIG. 8, when whole human EDTA-plasma is employed and lipoproteins are isolated, [$^{14}$C]-labeled lipids are incorporated into LDL and HDL. However, radiolabel preferentially associated with HDL. Furthermore, the radiolabel in HDL was localized to the larger HDL 2 subspecies, which include the HDL particles enriched in apo E. This result suggests that lipid efflux from RPE is enhanced by the apo E-containing HDL.

Example 7

Reduction of BM Lipids via Scavenger Receptors (SRS)

Scavenger receptors in macrophages function to phagocytose oxLDL molecules. There are types of SRs previously described in macrophages including SR-A1, SR-A2, SR-B1, SR-B2, CD36, and LOX. SRs are distinct from LDL receptors in that levels of expression for SRs are upregulated by oxLDL. This upregulation by intracellular oxLDL levels is modulated by nuclear hormone receptors, peroxisome proliferator activated receptor (PPAR) and retinoic acid X receptor (RXR), that exert transcriptional control of CD36 expression. Because the earliest lesion of AS, the fatty streak, consists of macrophages engulfed with excessive oxLDL, and because RPE cells similarly become filled with lipid inclusions in AMD, SR expression was studied in RPE cells. Expression of the following SRs in RPE cells was identified: CD36 (confirmation of previous investigators), SR-A1, SR-A2 (both first time demonstrated in RPE), SR-B1, SR-B2 (both first time demonstrated in RPE).

Figure 13:
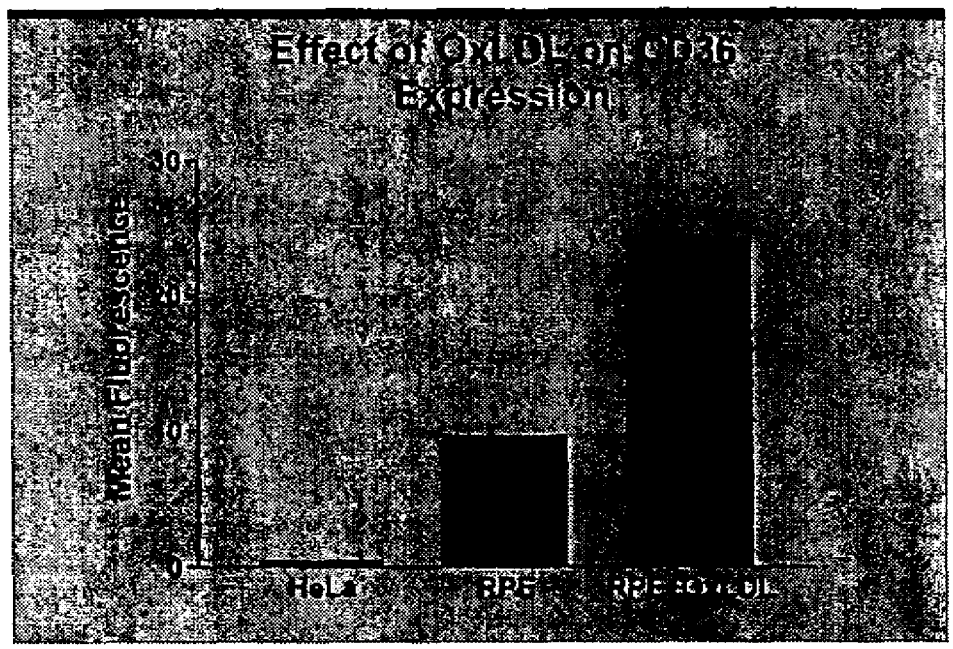
FIG. 13 shows stimulation of CD36 expression by oxidized lipid.

The inventors have also shown that, like macrophages, oxLDL upregulates expression of CD36 in RPE cells (FIG. 13). Additionally, RPE cells express the nuclear hormone receptors, PPAR and RXR, indicating control mechanisms for SR expression are analogous between the cell types. Thus, in specific embodiments the expression of RPE SRs in patients is controlled with PPAR and RXR ligands (e.g. PG-J2, thiazolidinediones, cis-retinoic acid). This controls the rate at which RPE cells phagocytose oxidized photoreceptor outer segments, and hence slows the rate at which abnormal lipid inclusions accumulate in RPE and BM. In other specific embodiments, expression of CD36 is downregulated with a composition such as tamoxifen, TGF-beta or INF-gamma. Similarly, regulating expression of other RPE SRs would control levels of lipids in both RPE and BM. For example, for SR-A regulation IGF-1, TGF-beta, EGF, and/or PDGF is used, and for SR-B regulation cAMP and/or estradiol (for upregulation) or TNF-alpha, LPS, and/or INF-gamma (for downregulation) is used.

Example 8

HDL Increases $^{14}C$ Lipid Efflux from RPE Cells Preferentially to other Lipoproteins Transcription of the apo E gene is regulated by liver-X-receptor alpha (LXR α) that acts as heterodimers with retinoid-X-receptor alpha (RXR α) (Mak et al., 2002). The inventors have previously shown that RPE cells express $T_3$ receptors (TRs) that also act as heterodimers with RXR α (Duncan et al., 1999). The inventors and others, have demonstrated that primary cultures of RPE cells express mRNA for lxr α, RXR α, apo E, and other proteins involved in regulation of lipid and cholesterol uptake, metabolism and efflux (summarized herein). In this Example, the inventors show that apo E secreted by primary cultures of RPE cells can be up-regulated by thyroid hormone ($T_3$), 22(R) hydroxycholesterol (HC), and cis retinoic acid (RA). The inventors also demonstrated that a high density lipoprotein (HDL) fraction rich in apo E is a preferential acceptor for labeled POS lipids.

As shown in Table II, the present inventors and other investigators have identified mRNAs for the proteins involved in regulating lipid and cholesterol uptake, metabolism and efflux. The cells used in the experiments described below express only the apo E3 allele (E3/E3).

TABLE II

Agents involved in regulating lipid and cholesterol uptake, metabolism, and efflux

| TRANSCRIPTION FACTORS | | LIGANDS |
|---|---|---|
| TR α1 | Thyroid hormone Receptor alpha 1 | $T_3$ |
| TR α2 | Thyroid hormone Receptor alpha 2 | $T_3$ |
| TR β 1 | Thyroid hormone Receptor beta 1 | $T_3$ |
| RXR α | Retinoid-X Receptor alpha | Retinoic Acid |
| RXR β | Retinoid-X Receptor beta | Retinoic Acid |
| PPAR γ | Peroxisome Proliferator Activator Receptor gamma | Oxidized lipids |
| Lxr α | Liver-X Receptor alpha | Oxysterols |
| CELL SURFACE RECEPTORS | | |
| SR-BI | Scavenger Receptor BI | Oxidized Lipids |
| SR-BII | Scavenger Receptor BII | Oxidized Lipids |
| SR-AI | Scavenger Receptor AI | Oxidized Lipoproteins |
| SR-AII | Scavenger Receptor AII | Oxidized Lipoproteins |
| Lox-1 | Lectin-like Oxidized LDL receptor 1 | Oxidized Lipoproteins |
| CHOLESTEROL/LIPID TRANSPORT AND METABOLISM | | FUNCTIONS |
| SR-BI | Scavenger Receptor BI | Reverse Cholesterol Transport |
| SR-BII | Scavenger Receptor BII | Reverse Cholesterol Transport |
| ABCA1 | ATP Binding Cassette Protein A1 | Reverse Cholesterol Transport |
| ACAT1 | Acyl-CoA Cholesterol Acyltransferase 1 | Cholesterol Acylation |
| Apo E | Apolipoprotein E | Cholesterol/ Lipid Trafficking |

As shown qualitatively in FIG. 6, $T_3$ (TR agonist), RA (RXR agonist), HC (LXR agonist) stimulate basal apo E secretion. As previously indicated, RPE cells were treated for 36 hours on Transwell® plates with serum free DMEM in upper and lower chambers +/− the drugs indicated. Control (C) refers to no drug addition; T refers to $10^{-7}$ M $T_3$; RA refers to $10^{-7}$ M cis retinoic acid; and HC refers to $2.5 \times 10^{-6}$ M 22(R) hydroxycholesterol. Basal media from 3 wells were combined, concentrated, and apo E was detected by western blotting.

Figure 14:
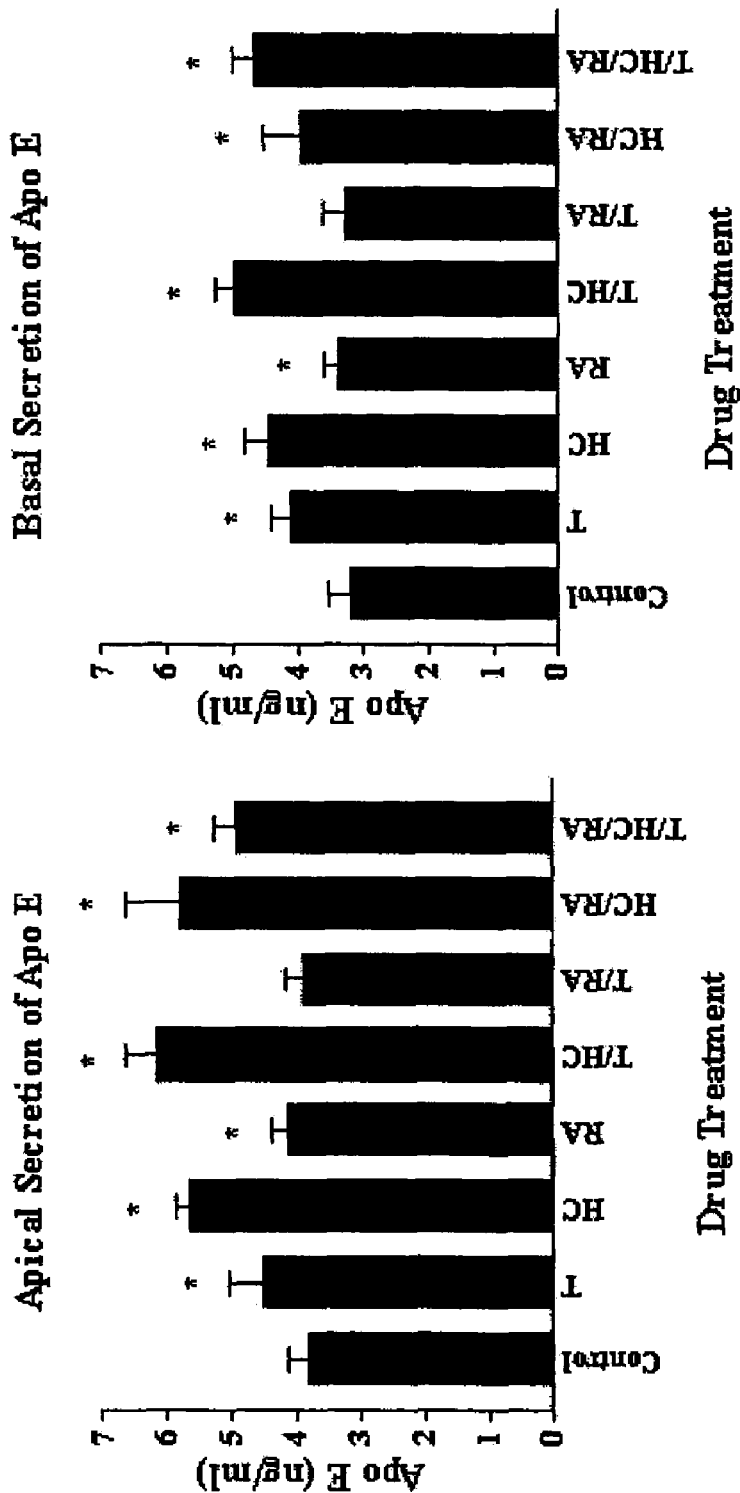
FIG. 14 illustrates apical and basal secretion from RPE cells of apoE in the presence of $T_3$ (T), 22(R) hydroxycholesterol, or cis retinoic acid (RA).

As shown quantitatively in FIG. 14, TR, LXR and RXR agonists upregulate apo E secretion alone and in combination, as assessed by ELISA assays. RPE cells were treated for 36 hours on Transwell® plates with serum free DMEM +/− the drugs indicated. Control refers to no drug addition, T refers to $10^{-7}$ M $T_3$; HC refers to $2.5 \times 10^{-6}$ M 22(R) hydroxycholesterol; RA refers to $10^{-7}$ M cis retinoic acid. N=6, * indicates p<0.05 (two-tailed t-test) compared to Control.

Figure 15:
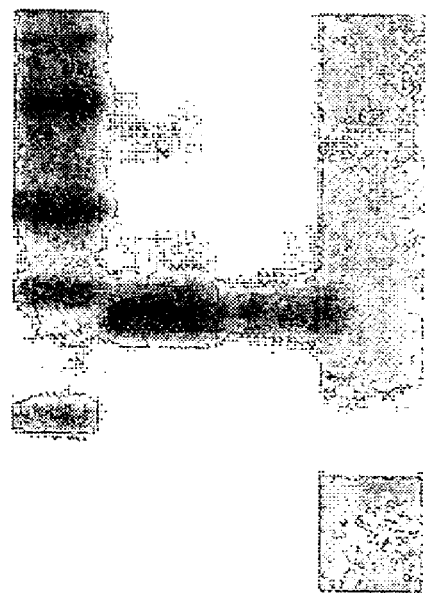
FIG. 15 shows that apoE secreted from RPE cells binds to HDL.

As shown in FIG. 15, apo E secreted from RPE cells binds to HDL. RPE cells on Transwell® plates were grown in DMEM with 5% FBS for 36 hours (apical chamber). Basal chambers had serum free DMEM with either 200, 50, or 0 μg/ml mouse HDL (lanes 2, 3, and 4 respectively). Lane 1 illustrates molecular weight markers. HDL was purified by ultracentrifugation, resolved by polyacrylamide gel electrophoresis, and human apo E was identified by western blotting.

Figure 16:
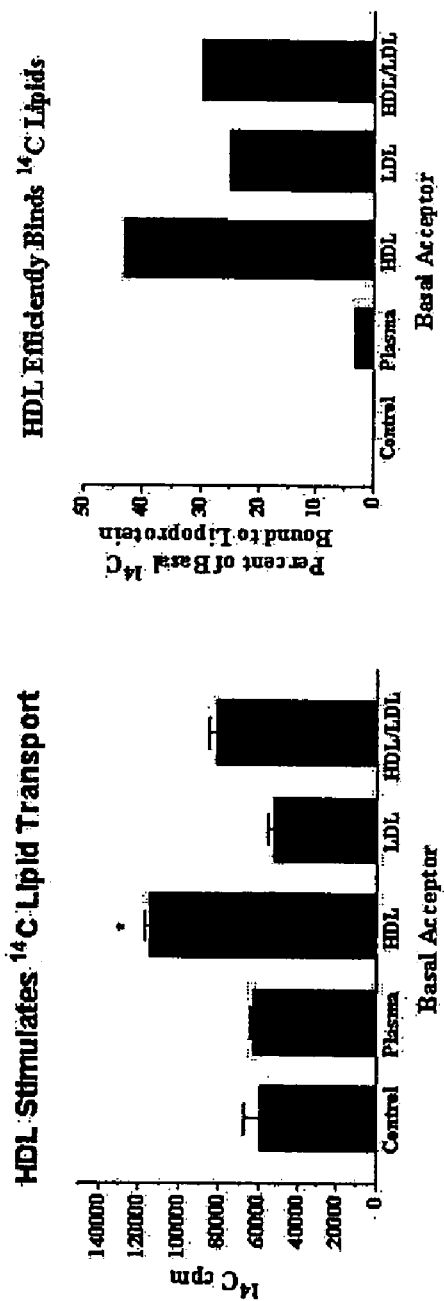
FIG. 16 demonstrates that HDL stimulates lipid efflux from RPE cells in culture.

As shown in FIG. 16, HDL stimulates POS lipid efflux from RPE cells in culture. RPE cells on Transwell® plates were fed $^{14}$C labeled POS in DMEM with 5% FBS for 36 hours (apical chamber). Basal chambers had serum free DMEM. Both upper and lower media contained either no addition (Control), 10% human plasma, 100 µg/ml HDL, 1000 µg/ml LDL or 50 µg/ml HDL+500 µg/ml LDL as indicated. FIG. 16 left: Basal $^{14}$C cpm/130 µl. N=3, * indicates p≦0.05 (two-tailed t-test) compared to Control. FIG. 16 right: Lipoproteins were purified by ultracentrifugation, dialyzed to remove soluble $^{14}$C, and counted.

As shown in FIG. 8, $^{14}$C labeled POS lipids preferentially bind to apo E containing high molecular weight HDL (HDL3). $^{14}$C labeled lipoproteins from the lower chamber were purified by ultracentrifugation and resolved on native polyacrylamide gels.

Figure 17:
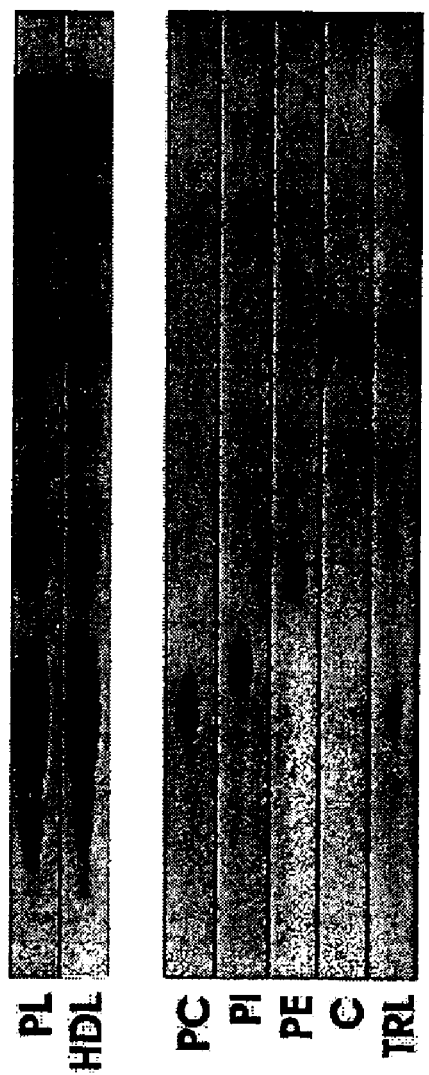
FIG. 17 shows characterization of HDL and plasma bound POS lipids by thin layer chromatography.

Characterization of HDL and plasma bound POS lipids was made by thin layer chromatography, as shown in FIG. 17. $^{14}$C labeled lipoproteins from the lower chamber were purified by ultracentrifugation, and lipids were resolved by thin layer chromatography followed by acid charring.

Figure 18:
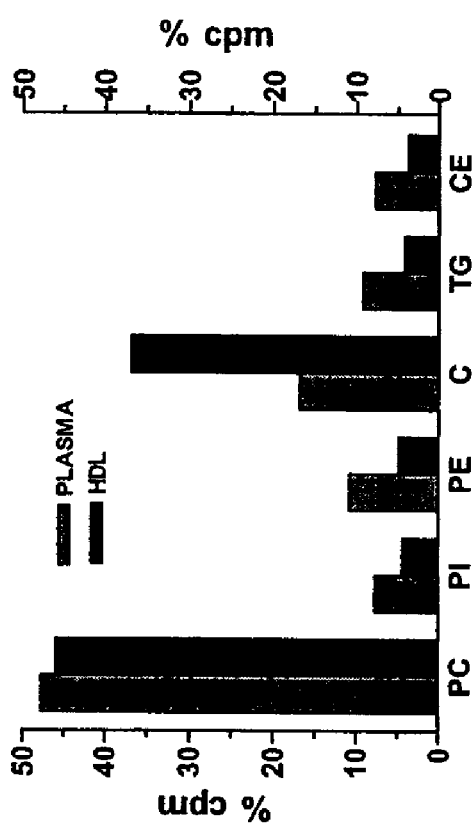
FIG. 18 shows plasma and HDL levels of species identified in FIG. 17.

As shown in FIG. 18, six spots in HDL and plasma were tentatively identified; at least 11 other spots are not yet identified. Spots identified by charring were cut out and $^{14}$C cpm determined by liquid scintillation counting.

Example 9

Exemplary Methods and Materials for Example 8

Cell Culture

Primary cultures of normal human RPE cells were prepared from a 35 year old donor eye as described (Song and Lui, 1990). Cells from passages 4 to 10 were used. RPE cells were grown on laminin-coated tissue culture plates, or on laminin coated 0.4 µM cellulose acetate Transwell® dishes (Costar) in DMEM H21 containing 5-10% fetal bovine serum (FBS), 2 mM glutamine, 5 µg/ml gentamycin, 100 IU/ml penicillin, 100 mg/ml streptomycin, 2.5 mg/ml fungizone, 1 ng/ml bFGF, and 1 ng/ml EGF. Where indicated, FBS was substituted with: 6 g/L NEAA, 0.39 g/L methylcellulose (serum free medium). No differences in cell morphology or protein expression were observed in cultures from different passages. RPE cells were grown at confluence for at least 14 days prior to undergoing the experimental treatments described below.

RT-PCR

RT-PCR was carried out on 1 µg of cDNA. The RT-PCR products are resolved by electrophoresis on 1.4% agarose gels. The RT-PCR primer sequences used are given followed by the predicted apo E RT-PCR product size. apo E forward: 5'-TAA GCT TGG CAC GGC TGT CCA AGG A (SEQ ID NO:13); apo E reverse: 5'-ACA GAA TTC GCC CCG GCC TGG TAC AC (SEQ ID NO:14); 241 bp product (detects both apo E3 and apo E4). PCR was conducted for 20-30 cycles at 55° C. in buffer containing 2.0-5.0 mM MgCl$_2$. The RT-PCR product of the predicted size for apo E had its identity confirmed by DNA sequencing. Only the apo E3 mRNA sequence was detected. Messenger RNAs for the other proteins listed in the Table II were identified using similar strategies with primers specific to each cDNA.

Western Blotting

Briefly, media was concentrated 20-fold by centrifugal ultrafiltration (VIVA SPIN 20, MCO 5,000; Viva Sciences). Concentrated media (20 µg protein) was purified over Heparin-Sepharose CL-4B. The apo E containing (bound) fraction was eluted and re-concentrated to 20 µl. Apo E was resolved by 5-25% linear gradient SDS polyacrylamide gel electrophoresis, and proteins were electrophoretically transferred to nitrocelluose. Membranes were blocked with 10% BSA and probed with 1% goat anti-human apo E antiserum. Apo E antibodies were detected colorimetrically with horseradish peroxidase conjugated rabbit anti-goat IgG and NiCl$_2$-enhanced diaminobenzine staining.

ELISA Assay

Media samples treated with 0.1% Tween-20 containing 1% bovine serum albumin were incubated (37° C., 4 h) in 96-well plates previously coated with apo E-affinity purified goat anti-apo E antibody. Apo E was detected using a secondary antibody-peroxidase conjugate and 3.3.5.5'-tetramethylethylenediamine (TMB) substrate. Optical density was measured at 450 nm. The assay was calibrated with purified plasma apo E. The dynamic range of the assay was 1-40 ng/ml apo E with a CV<5%.

POS Lipid Transport and Lipoprotein Gel Analysis

Briefly, purified POS lipids were labeled with $^{14}$C docosohexanoic acid as described (Guisto et al., 1986). Twenty µg/ml (protein) of POS were added to the top chambers of 6 well Transwell® plates. The bottom chambers contained serum free medium with or without human high density lipoprotein (HDL), human low density lipoprotein (LDL), or human plasma in the amounts indicated. After 36 hours, cell culture medium was harvested from the bottom chambers, adjusted to a density of 1.25 g/ml with solid potassium bromide and underlayed over a KBr solution of d=1.21. Samples were ultracentrifuged (Beckman 50.2Ti, 45,000 rpm, 10° C.) for 20 hours. The top (lipoprotein) layer was removed, dialyzed, and subjected to non-denaturing gel electrophoresis. The gels were stained with Coomassie Blue and photographed, after which 2 mM slices were subjected to scintillation counting.

Thin Layer Chromatography

Lipoprotein samples were extracted for lipid by the method of Bligh-Dyer, which is well known in the art. Lipids were resolved by silica gel K6 thin layer chromtography using sequential developments in Solvent 1: chloroform/methanol/acetic acid/water (25:15:4:2) and Solvent 2: n-hexane/diethylether/acetic acid (65:35:2). Lipid species were detected by acid charring, plates were immersed in 7.5% copper acetate, 2.5% copper sulfate, 8% phosphoric acid and heated on a hot plate for 1 hour. $^{14}$C radioactivity was measured by liquid scintillation counting in standard methods known in the art.

Example 10

ApoA-I Delivery to Increase Reverse Cholesterol Transport

The present inventors have shown that HDL is a preferred cholesterol and phospholipids acceptor for lipids effluxed by cultured human RPE. In aging BM, there is progressive accumulation of lipid and cross-linked protein that impedes hydraulic conductivity and macromolecular permeability. This abnormal deposition may also impair the ability of some larger molecular weight species of HDL to act as a lipoprotein acceptor. As HDL is unable to pass through BM and promote efflux and bind effluxed lipids, more lipids would accumulate in both RPE and BM. Indeed such accumulations are a major finding in age-related macular degeneration (AMD).

Apolipoprotein A1 (ApoA-I) is the major lipoprotein component of HDL. It has a mass of approximately 28 kDaltons. ApoA-I bound to phospholipids comprises nascent HDL particles that bind to ABCA1 on the RPE basal membrane and promote lipid efflux. Because of ApoA-I's low molecular weight, it can penetrate an aged BM more easily than larger molecular weight species of HDL to bind to the RPE. In addition to it role in promoting reverse cholesterol transport from RPE, ApoA-I also in a potent anti-oxidant. Anti-oxidants have been established to reduce visual loss in patients with AMD.

Several methods are used to increase ApoA-I delivery to RPE as a treatment for AMD:

1. ApoA-I is administered intravenously as has been done in mouse models of atherosclerosis and in patients with coronary artery disease.

2. ApoA-I, which is normally comprised on L-amino acids, can be administered as an ApoA-I mimetic peptide consisting of D-amino acids. The D-amino acid based ApoA-I mimentic peptide is not recognized as readily by human proteases, and thus can be administered orally. This would be more convenient than parenteral administration with an intravenous formulation containing the L-amino acid ApoA-I or its mimetic peptide.

3. Oral synthetic phospholipid (1,2 Dimyristoyl-α-glycero-3-phosphocholine, DMPC) increases levels of circulating ApoA-I.

By way of example, patients with AMD (atrophic or exudative) are administered either intravenous ApoA-I, ApoA-I mimetic peptide, or DMPC to increase levels of circulating ApoA-I. Administration could occur as frequent as daily or less frequently as in every other month depending on the method of administration and the clinical response.

Apo A-I mimetic peptides may be synthesized according to standard methods in the art, and in some embodiments one or more amino acids in the peptide are the D-stereoisomer. Methods to synthesize mimetic peptides are known in the art, including those described in de Beer, M. C., et al. (2001) and Matz and Jonas, 1982.

The peptides are based on the sequence Ac-D-W-L-K-A-F-Y-D-K-V-A-E-K-L-K-E-A-F-NH2 (Ac-18A-NH2 or 2F) (SEQ ID NO:15) (Navab et al., 2003), where Ac symbolizes acetylated. Thus, in specific embodiments, the C-terminus is carboxylated. The 2F peptide or an analog of 2F with the primary amino acid sequence Ac-D-W-F-K-A-F-Y-D-K-V-A-E-K-F-K-E-A-F-NH2 (4F) (SEQ ID NO:16) is used (Navab et al., 2003). An example of a human apolipoprotein A1 includes: LSPLGEEMRD RARAHVDALR THLAPYSDEL RQPLAARLEA LKENGGARLA EYHAKATEHL STLSEKA (SEQ ID NO:17). Other apolipoprotein A1 sequences, including those from organisms other than human, are available to the skilled artisan at the National Center for Biotechnology Information's GenBank database on the World Wide Web.

In some embodiments of the present invention, a mouse model is utilized to characterize administration of ApoA-I compositions. For example, the model generated by Dithmar et al. (2000) or an analogous model generated by similar methods in the art may be used in optimizing the present invention. In this model, ApoE$^-$ mice demonstrate ultrastructural changes in Bruch's membrane, such as accumulation of material similar to basal linear deposit and an increase in membrane-bound material.

Example 11

ApoA-I and RPE Cells

Figure 19:
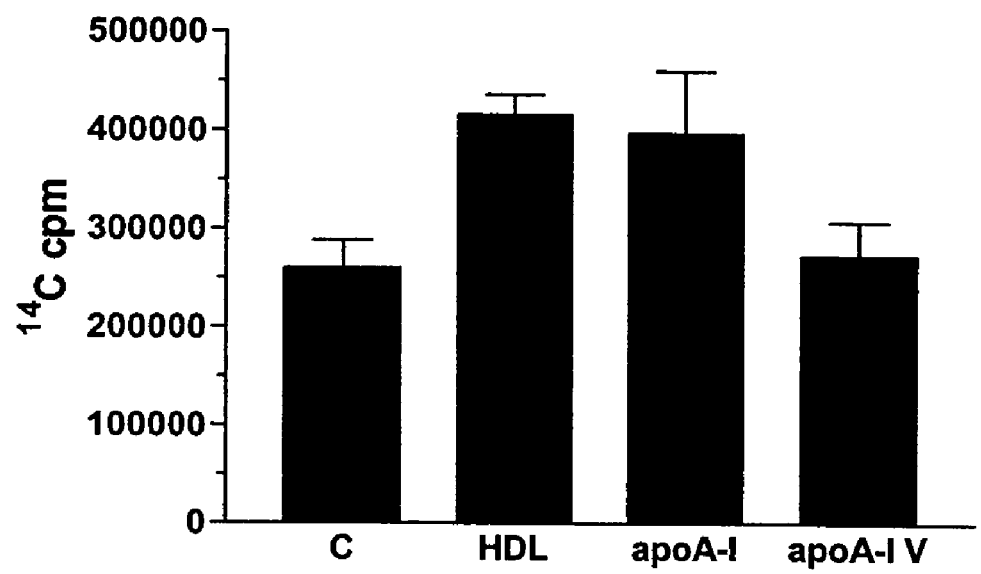
FIG. 19 shows measurement of $^{14}C$-labeled lipid efflux for no human high density lipoprotein (HDL) (Control); 100 µg/ml of human HDL; pure human apoA-I; or human apoA-I vesicles.

The present inventors have created liposomes comprising apoA-I (artificial preβ$_1$ HDL). Artificial discoidal apoA-I liposomes comprising purified human plasma apoAI, the saturated phospholipid dimyristoyl-L-α-phoshatidylcholine (DMPC) and cholesterol were constructed by the sodium cholate dialysis method. Liposomes were prepared using a molar ratio of approximately 1/5/95, apoA-I/free cholesterol/DMPC. Human retinal pigment epithelial cells grown on 6 well laminin coated Transwell® plates were fed $^{14}$C-docosahexaenoic acid labeled photoreceptor outer segments in medium containing 5% lipoprotein free fetal bovine serum for 36 hours (apical chamber). Basal chambers contained serum free medium and either no human high density lipoprotein (HDL) (Control), 100 µg/ml of human HDL, pure human apoA-I, or human apoA-I vesicles. An aliquot of the basal medium was subjected to liquid scintillation counting. The results are shown in FIG. 19. Wells were treated in triplicate. HDL stimulated $^{14}$C-labeled lipid efflux by about 60%. ApoA-I appeared to stimulate 14C-labeled lipid efflux. The apoA-I vesicles (apoA-I V) did not stimulate $^{14}$C-labeled lipid efflux.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference. The references, to the extent that they provide exemplary procedural or other details supplementary to those set forth herein, are specifically incorporated herein by reference.

Patents

U.S. Pat. No. 6,071,924
U.S. Pat. No. 5,846,711
U.S. Pat. No. 5,440,013
U.S. Pat. No. 5,618,914
U.S. Pat. No. 5,670,155
U.S. Pat. No. 5,446,128
U.S. Pat. No. 5,710,245
U.S. Pat. No. 5,840,833
U.S. Pat. No. 5,859,184
U.S. Pat. No. 5,929,237
U.S. Pat. No. 5,475,085
U.S. Pat. No. 5,672,681
U.S. Pat. No. 5,674,976
U.S. Pat. No. 4,554,101
U.S. Patent Application Publication US 2002/0142953
WO 00/52479
WO 01/58494
WO 02/13812
WO 01/79446

Publications

Anderson D H, Ozaki S, Nealon M, Neitz J, Mullins R F, Hageman G S, Johnson L V: Local cellular sources of apolipoprotein E in the human retina and retinal pigmented epithelium: implications for the process of drusen formation: Am J Ophthalmol. 2001; 131(6):767-8

Anderson, D. H. et al. (2001) Local Cellular Sources of Apolipoprotein E in the Human Retina and Retinal Pigmented Epithelium: Implications for the Process of Drusen Formation, Amer. J. Ophthalm. 131(6):767-781.

Bellosta S, Mahley R, Sanan D, Murata J, Newland D, Taylor J, Pitas R. Macrophage-specific expression of human apolipoprotein E reduces atherosclerosis in hypercholesterolemic E-null mice. J Clin Invest. 1995; 96:2170-217

Browning P J, Roberts D D, Zabrenetzky V, Bryant J, Kaplan M, Washington R H, Panet A, Gallo R C, Vogel T: Apolipoprotein E (ApoE), a novel heparin-binding protein inhibits the development of Kaposi's sarcoma-like lesions in BALB/c nu/nu mice. J Exp Med. 1994; 180(5):1949-54

Curcio, C. A., K. Bradley, C. Guidry, M. Kirk, L. Wilson, S. Barnes, H. S. Kruth, C. C. Y. Chang, T. Y. Chang: A Local Source for Esterified Cholesterol (EC) in Human Bruch's Membrane (BrM), ARVO Abstracts 2002 (need ref)

Curcio, Christine A., Millican, C. Leigh, Bailey, Tammy, Kruth, Howard S. Accumulation of Cholesterol with Age in Human Bruch's Membrane. Invest. Ophthalmol. Vis. Sci. 2001 42: 265-274 de Beer, M. C., et al., Apolipoprotein A-II modulates the binding and selective lipid uptake of reconstituted high density lipoprotein by scavenger receptor BI. J Biol Chem, 2001. 276(19): p. 15832-9.

Dithmar, Stefan, Curcio, Christine A., Le, Ngoc-Anh, Brown, Stephanie, Grossniklaus, Hans E.: Ultrastructural Changes in Bruch's Membrane of Apolipoprotein E-Deficient Mice Invest. Ophthalmol. Vis. Sci. 2000 41: 2035-2042

Duncan K G, Bailey K R, Baxter J D, Schwartz D M. The human fetal retinal pigment epithelium: A target tissue for thyroid hormones. Ophthalmic Res. 1999; 31(6):399-406.

Feeney-Burns L, Hilderbrand E S, Eldridge S: Aging human RPE: morphometric analysis of macular, equatorial, and peripheral cells. Invest Ophthalmol Vis Sci 1984; 25: 195-200.

Friedman, E. (2000) The Role of the Atherosclerotic Process in the Pathogenesis of Age-related Macular Degeneration, Amer. J. Ophthalm. 130(5):658-663

Guisto N M, de Boschero M I, Sprecher H, Aveldano M I: Active labeling of phosphatidylcholines by [1-14C] docosahexaenoate in isolated photoreceptor membranes. Biochim Biophys Acta 1986; 860:137-48

Hasty, A. H., M. F. Linton, S. J. Brandt, V. R. Babaev, L. A. Gleaves, and S. Fazio. 1999. Retroviral gene therapy in ApoE-deficient mice: ApoE expression in the artery wall reduces early foam cell lesion formation. Circulation. 99: 2571-2576

Holz F G, Sheraidah G, Pauleikhoff D, Bird A C: Analysis of lipid deposits extracted from human macular and peripheral Bruch's membrane. Arch Ophthalmol 1994; 112: 402-406.

Janowski B A, Grogan M J, Jones S A, Wisely G B, Kliewer S A, COrey E J, Mangelsdorf D J: Structural requirements of ligands for the oxyserol liver X receptors LXRa and LXRb. Proc Natl Acad Sci (USA) 1999 January 96:266-271.

Johannesson et al., 1999, "Bicyclic tripeptide mimetics with reverse turn inducing properties." J. Med. Chem. 42:601-608.

Kennedy C J, Rakoczy P E, Constable I J: Lipofuscin of the retinal pigment epithelium: a review. Eye 1995; 9:262-274.

Klaver C C, Kliffen M, van Duijn C M, Hofman A, Cruts M, Grobbee D E, van Broeckhoven C, de Jong P T: Genetic association of apolipoprotein E with age-related macular degeneration. Am J Hum Genet. 1998 July; 63(1):200-6

Kliffen, Mike, Lutgens, Esther, Daemen, Mat J A P, de Muinck, Ebo D, Mooy, Cornelia M, de Jong, Paulus T V M: The APO*E3-Leiden mouse as an animal model for basal laminar deposit Br J Ophthalmol 2000 84: 1415-1419

Laffitte B A, Repa J J, Joseph S B, Wilpitz D C, Kast H R, Mangelsdorf D J, Tontonoz P: LXRs control lipid-inducible expression of the apolipoprotein E gene in macrophages and adipocytes. Proc Natl Acad Sci USA 2001 Jan. 16; 98(2):507-12

Laffitte B A, Repa J J, Joseph S B, Wilpitz D C, Kast H R, Mangelsdorf D J, Tontonoz P: The modulation of apolipoprotein E gene expression by 3,3'-5-triiodothyronine in HepG2 cells occurs at transcriptional and post-transcriptional levels. Eur J. Biochem. 1994 Sep. 1; 224(2):463-71.

Langer C, Huang Y, Cullen P, Wiesenhütter B, Mahley R W, Assmann G, von Eckardstein A. Endogenous apolipoprotein E modulates cholesterol efflux and cholesterol ester hydrolysis mediated by high-density lipoprotein-3 and lipid-free apolipoproteins in mouse peritoneal macrophages. J Mol Med. 2000; 78:217-227

Lin, C. Y., H. W. Duan, and T. Mazzone. 1999. Apolipoprotein E-dependent cholesterol efflux from macrophages: kinetic study and divergent mechanisms for endogenous versus exogenous apolipoprotein E. J. Lipid Res. 40: 1618-1626

Mak P A, Laffitte B A, Desrumaux C, Joseph S B, Curtiss L K, Mangelsdorf D J, Tontonoz P, Edwards P A: Regulated expression of the apolipoprotein E/C-I/C-IV/C-II gene cluster in murine and human macrophages. A critical role for nuclear liver X receptors alpha and beta. J Biol. Chem. 2002 Aug. 30; 277(35):31900-8

Malek G, Li C M, Guidry C, Medeiros N E, Curcio C A: Apolipoprotein B in cholesterol-containing drusen and Basal deposits of human eyes with age-related maculopathy. Am J Pathol 2003; 162(2):413-25

Matz, C. E. and A. Jonas, Micellar complexes of human apolipoprotein A-I with phosphatidylcholines and cholesterol prepared from cholate-lipid dispersions. J Biol Chem, 1982. 257(8): p. 4535-40

Mazzone T, Reardon C. Expression of heterologous human apolipoprotein E by J774 macrophages enhances cholesterol efflux to HDL3. J Lipid Res. 1994; 35:1345-1353

Mazzone, T., L. Pusteinikas, and C. Reardon. 1992. Secretion of apoE by macrophages is accompanied by enhanced cholesterol efflux. Circulation. 86 (Suppl. I): I-2

Michael E. Kelly, Moira A. Clay, Meenakshi J. Mistry, Hsiu-Mei Hsieh-Li and Judith A. K. Harmony: Apolipoprotein E Inhibition of Proliferation of Mitogen-Activated T Lymphocytes: Production of Interleukin 2 with Reduced Biological Activity, Cellular Immunology, Volume 159, Issue 2, December 1994, Pages 124-139.

Moore D J, Clover G M: The effect of age on the macromolecular permeability of human Bruch's membrane. Invest Ophthalmol Vis Sci 2001; 42: 2970-2975

Moore D J, Hussain A A, Marshall J: Age-related variation in the hydraulic conductivity of Bruch's membrane. Invest Ophthalmol Vis Sci 1995; 36: 1290-1297.

Mullins R F, Russell S R, Anderson D H, Hageman G S. Drusen associated with aging and age-related macular degeneration contain proteins common to extracellular deposits associated with atherosclerosis, elastosis, amyloidosis, and dense deposit disease. FASEB J. 2000 May; 14(7):835-46.

Navab M, Anantharamaiah G M, et al. Human apolipoprotein A1 mimetic peptides for the treatment of atherosclerosis. Curr Opin Investig Drugs 2003; 4(9):1100-4.

Pauleikhoff D, Harper C A, Marshall J, Bird A C: Aging changes in Bruch's membrane. A histochemical and morphologic study. Ophthalmology 1990; 97: 171-178.

Sergio Fazio, Vladimir R. Babaev, Alisa B. Murray, Alyssa H. Hasty, Kathy J. Carter, Linda A. Gleaves, James B. Atkinson, and MacRae F. Linton: Increased atherosclerosis in mice reconstituted with apolipoprotein E null macrophages PNAS 94: 4647-4652

Sheraidah G, Steinmetz R, Maguire J, Pauleikhoff D, Marshall J, Bird A C: Correlation between lipids extracted from Bruch's membrane and age. Ophthalmology 1993; 100: 47-51.

Shimano, H., J. Ohsuga, M. Shimada, Y. Namba, T. Gotoda, K. Harada, M. Katsuki, Y. Yazaki, and N. Yamada. 1995. Inhibition of diet-induced atheroma formation in transgenic mice expressing apolipoprotein E in the arterial wall. J. Clin. Invest. 95: 469-476

Simonelli F, Margaglione M, Testa F, Cappucci G, Manitto M P, Brancato R, Rinaldi E: Apolipoprotein E Polymorphisms in Age-Related Macular Degeneration in an Italian Population. Ophthalmic Res 2001; 33:325-328

Song M K, Lui G M: Propagation of fetal human RPE cells: preservation of original culture morphology after serial passage. J Cell Physiol 1990; 143:196-203

Souied E H, Benlian P, Amouyel P, Feingold J, Lagarde J P, Munnich A, Kaplan J, Coscas G, Soubrane G.: The epsilon4 allele of the apolipoprotein E gene as a potential protective factor for exudative age-related macular degeneration. Am J Ophthalmol. 1998; 125(3):353-9

Spaide R F, Ho-Spaide W C, Browne R W, Armstrong D: Characterization of peroxidized lipids in Bruch's membrane. Retina 1999; 19: 141-147.

Starita C, Hussain A A, Pagliarini S, Marshall J: Hydrodynamics of ageing Bruch's membrane: implications for macular disease. Exp Eye Res 1996; 62: 565-572.

Tangirala R K, Pratico D, FitzGerald G A, Chun S, Tsukamoto K, Maugeais C, Usher D C, Pure E, Rader D J: Reduction of isoprostanes and regression of advanced atherosclerosis by apolipoprotein E. J Biol. Chem. 2001 Jan. 5; 276(1):261-6

Taylor, Hugh R, Keeffe, Jill E: World blindness: a 21st century perspective. Br J Ophthalmol 2001 85: 261-266

VanNewkirk, Mylan R., Nanjan, Mukesh B., Wang, Jie Jin, Mitchell, Paul, Taylor, Hugh R., McCarty, Cathy A.: The prevalence of age-related maculopathy: The visual impairment project Ophthalmology 2000 107: 1593-1600

Vita et al., 1998, "Novel miniproteins engineered by the transfer of active sites to small natural scaffolds." Biopolymers 47:93-100.

Weisshoff et al., 1999, "Mimicry of beta II'-turns of proteins in cyclic pentapeptides with one and without D-amino acids." Eur. J. Biochem. 259:776-788.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of improving impaired dark adaptation in an individual, comprising the steps of:
identifying an individual afflicted with impaired dark adaptation; and
delivering to the individual a therapeutically effective amount of a composition comprising ApoA-I.

2. The method of claim 1, further comprising the step of detecting improvement of at least one symptom of said impaired dark adaptation in the individual.

3. A method of improving impaired dark adaptation in an individual, comprising the steps of:
identifying an individual afflicted with impaired dark adaptation; and
delivering to the individual a therapeutically effective amount of a composition comprising an ApoA-I peptide or a polynucleotide encoding an ApoA-I peptide.

4. The method of claim 3, wherein the ApoA-I peptide is a mimetic peptide.

5. The method of claim 3, wherein the ApoA-I peptide comprises SEQ ID NO:15.

6. The method of claim 3, wherein the ApoA-I peptide comprises SEQ ID NO:16.

7. The method of claim 3, wherein the ApoA-I peptide comprises D-amino acids.

8. A method of improving impaired dark adaptation in an individual, comprising the steps of:
identifying an individual afflicted with impaired dark adaptation; and
delivering to the individual a therapeutically effective amount of a composition comprising an agent that increases the level of circulating ApoA-I in the individual.

9. The method of claim 8, wherein the agent comprises 1,2 dimyristoyl-α-glycero-3-phosphocholine (DMPC).

10. The method of claim 1, wherein the composition is administered to the individual locally or systemically.

11. The method of claim 1, wherein the composition is administered orally, parenterally, topically, intradermally, subcutaneously, intramuscularly, intraperitoneally, intraocularly, or intravenously.

12. The method of claim 11, wherein said composition is administered to an individual orally, wherein said composition is further defined as comprising a liposome.

* * * * *